United States Patent
Klosin et al.

(10) Patent No.: US 10,214,622 B2
(45) Date of Patent: *Feb. 26, 2019

(54) CATALYST SYSTEMS FOR OLEFIN POLYMERIZATION

(71) Applicant: Dow Global Technologies LLC, Midland, MI (US)

(72) Inventors: Jerzy Klosin, Midland, MI (US); Ruth Figueroa, Midland, MI (US); Pulikkottil J. Thomas, Midland, MI (US); Mehmet Demirors, Pearland, TX (US); Sylvie Desjardins, Lake Jackson, TX (US); Mridula Kapur, Lake Jackson, TX (US); Philip P. Fontaine, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/652,606

(22) Filed: Jul. 18, 2017

(65) Prior Publication Data

US 2018/0009958 A1    Jan. 11, 2018

Related U.S. Application Data

(63) Continuation of application No. 14/437,543, filed as application No. PCT/US2013/073976 on Dec. 10, 2013, now Pat. No. 9,751,998.

(60) Provisional application No. 61/746,151, filed on Dec. 27, 2012.

(51) Int. Cl.
| | |
|---|---|
| C08J 5/18 | (2006.01) |
| C07F 7/18 | (2006.01) |
| B65D 51/26 | (2006.01) |
| C08F 210/16 | (2006.01) |
| C08L 23/06 | (2006.01) |
| C08L 23/08 | (2006.01) |
| C07F 5/00 | (2006.01) |
| C08F 4/64 | (2006.01) |
| C08F 4/60 | (2006.01) |
| C08L 23/02 | (2006.01) |
| C08F 210/14 | (2006.01) |

(52) U.S. Cl.
CPC ............. C08J 5/18 (2013.01); B65D 51/26 (2013.01); C07F 5/00 (2013.01); C07F 7/1804 (2013.01); C08F 4/64186 (2013.01); C08F 210/16 (2013.01); C08L 23/06 (2013.01); C08L 23/08 (2013.01); C08L 23/0815 (2013.01); C08F 4/60193 (2013.01); C08F 210/14 (2013.01); C08F 2500/03 (2013.01); C08J 2323/08 (2013.01); C08J 2423/08 (2013.01); C08L 23/02 (2013.01); C08L 2203/16 (2013.01); C08L 2205/02 (2013.01); C08L 2205/025 (2013.01); C08L 2205/03 (2013.01); Y02P 20/582 (2015.11)

(58) Field of Classification Search
CPC .................... C08F 4/60193; C08F 4/64193
See application file for complete search history.

(56) References Cited

U.S. PATENT DOCUMENTS

| | | |
|---|---|---|
| 5,064,802 A | 11/1991 | Stevens et al. |
| 5,153,157 A | 10/1992 | Hlatky et al. |
| 5,296,433 A | 3/1994 | Siedle et al. |
| 5,321,106 A | 6/1994 | LaPointe |
| 5,350,723 A | 9/1994 | Neithamer et al. |
| 5,425,872 A | 6/1995 | Devore et al. |
| 5,625,087 A | 4/1997 | Devore et al. |
| 5,721,185 A | 2/1998 | LaPointe et al. |
| 5,783,512 A | 7/1998 | Jacobsen et al. |
| 5,883,204 A | 3/1999 | Spencer et al. |
| 5,919,983 A | 7/1999 | Rosen et al. |

(Continued)

FOREIGN PATENT DOCUMENTS

| | | |
|---|---|---|
| CN | 102712795 A | 10/2012 |
| GB | 1069848 A | 5/1967 |

(Continued)

OTHER PUBLICATIONS

Bonvonsombat et al., "Regioselective Iodination of Phenol and Analogues Using N-Iodosuccinimide and p-toluenesulfonic Acid", Tetrahedrom Letters, 2009, 50: 22, 2664-2667.
Chinese Office Action dated Aug. 22, 2016 pertaining to Chinese Application No. 201380067366.4.
Chinese Office Action dated Jan. 25, 2018 pertaining to Chinese Application No. 201380065868.3.
Chinese Office Action dated May 15, 2017 pertaining to Chinese Application No. 201380067366.4.

(Continued)

Primary Examiner — Rip A Lee
(74) Attorney, Agent, or Firm — Dinsmore & Shohl LLP

(57) ABSTRACT

The instant invention provides procatalysts and catalyst systems for olefin polymerization, olefin based polymers polymerized therewith, and process for producing the same. In one embodiment, the instant invention provides a procatalyst comprising a metal-ligand complex of formula (I):

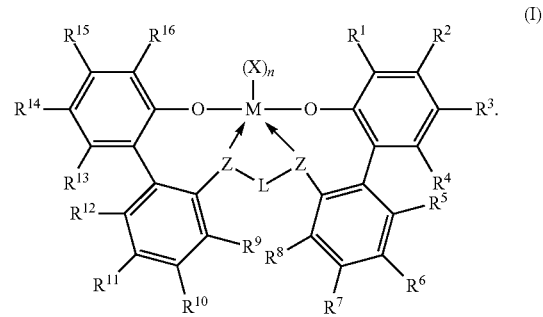

12 Claims, 5 Drawing Sheets

(56) References Cited

U.S. PATENT DOCUMENTS

| | | | |
|---|---|---|---|
| 6,103,657 | A | 8/2000 | Murray |
| 6,515,155 | B1 | 2/2003 | Klosin et al. |
| 6,696,379 | B1 | 2/2004 | Carnahan et al. |
| 6,869,904 | B2 | 3/2005 | Boussie et al. |
| 7,060,848 | B2 | 6/2006 | Boussie et al. |
| 7,163,907 | B1 | 1/2007 | Canich et al. |
| 7,951,882 | B2 | 5/2011 | Arriola et al. |
| 8,609,794 | B2 | 12/2013 | Klosin et al. |
| 8,729,201 | B2 | 5/2014 | Fontaine et al. |
| 9,029,487 | B2 | 5/2015 | Klosin et al. |
| 9,102,819 | B2 | 8/2015 | Kapur et al. |
| 9,522,855 | B2 | 12/2016 | Klosin |
| 9,527,940 | B2 | 12/2016 | Demirors et al. |
| 9,527,941 | B2 | 12/2016 | Demirors et al. |
| 9,601,230 | B2 | 3/2017 | Nair et al. |
| 9,601,231 | B2 | 3/2017 | Klosin et al. |
| 9,605,098 | B2 | 3/2017 | Klosin et al. |
| 2004/0005984 | A1* | 1/2004 | Boussie ............... B01J 31/223 502/150 |
| 2011/0039082 | A1 | 2/2011 | Yun et al. |
| 2011/0082249 | A1 | 4/2011 | Shan et al. |
| 2011/0282018 | A1 | 11/2011 | Klosin et al. |
| 2014/0330056 | A1 | 11/2014 | Klosin et al. |
| 2014/0357918 | A1* | 12/2014 | Klosin ................... C08F 10/00 585/511 |
| 2015/0337062 | A1 | 11/2015 | Demirors et al. |
| 2015/0337063 | A1 | 11/2015 | Demirors et al. |
| 2015/0344601 | A1 | 12/2015 | Demirors et al. |
| 2015/0344602 | A1 | 12/2015 | Demirors et al. |

FOREIGN PATENT DOCUMENTS

| | | | |
|---|---|---|---|
| JP | 2000159829 A | 6/2000 | |
| JP | 2001525859 A | 12/2001 | |
| JP | 2005523921 A | 8/2005 | |
| JP | 2011525212 A | 9/2011 | |
| JP | 2013521382 A | 6/2013 | |
| JP | 2013534934 A | 9/2013 | |
| JP | 2013541631 A | 11/2013 | |
| JP | 2013544940 A | 12/2013 | |
| WO | 2003091262 A2 | 11/2003 | |
| WO | 2007136494 A2 | 11/2007 | |
| WO | 2007136496 A2 | 11/2007 | |
| WO | WO 2007/136496 A2 * | 11/2007 | ............... C08F 2/04 |
| WO | 2010061630 A1 | 6/2010 | |
| WO | 2011025784 A1 | 3/2011 | |
| WO | 2011041696 A1 | 4/2011 | |
| WO | 2011109563 A2 | 9/2011 | |
| WO | 2011146044 A1 | 11/2011 | |
| WO | 2011146291 A1 | 11/2011 | |
| WO | WO 2011/146044 A1 * | 11/2011 | ............ C08F 210/16 |
| WO | 2012004683 A2 | 1/2012 | |
| WO | 2012027448 A1 | 3/2012 | |
| WO | 2012064630 A2 | 5/2012 | |
| WO | 2013101375 A1 | 7/2013 | |
| WO | 2014105411 A1 | 7/2014 | |
| WO | 2014105412 A1 | 7/2014 | |
| WO | 2014105413 A1 | 7/2014 | |
| WO | 2014209927 A1 | 12/2014 | |
| WO | 2015045928 A1 | 4/2015 | |
| WO | 2015045930 A1 | 4/2015 | |

OTHER PUBLICATIONS

Chinese Office Action dated May 3, 2017 pertaining to Chinese Application No. 201380065868.3.
Chinese Office Action dated Sep. 1, 2016 pertaining to Chinese Application No. 201380065868.3.
Chinese Office Action dated Nov. 1, 2017 pertaining to Chinese Application No. 201480033642.X.
Chinese Office Action pertaining to Chinese Patent Application No. 201380065667.3 dated Oct. 27, 2016.
Chinese Office Action pertaining to Chinese Patent Application No. 201380065848.6 dated Sep. 1, 2016.
Chinese Office Action pertaining to Chinese Patent Application No. 201380067367.9 dated May 11, 2017.
Chinese Office Action dated Aug. 19, 2016 pertaining to Chinese Patent Application No. 201380067367.9.
EP Communication Pursuant to Rules 161(1) and 162 EPC dated Aug. 4, 2015 for EPO Application No. 13811737.9.
EPO Communication pursuant to Rules 161(1) and 162 EPC dated Aug. 4, 2015 pertaining to European Patent Application No. 13811736.1.
EPO Communication pursuant to Rules 161(1) and 162 EPC dated Aug. 4, 2015 pertaining to European Patent Application No. 13812379.9.
European Search Report pertaining to European Patent Application Serial No. 14741484.1 dated Aug. 24, 2017.
Han et al., "Synthesis of diindeno-Fused 4H-Cyclopenta[def]phenanthren-4-ones and Related Compounds via Benzannulated Enediynyl Propargylic Alcohols", J. Org. Chem., 2005, 70: 6, 2406-2408.
International Preliminary Report on Patentability pertaining to PCT/US2013/0073982 dated Jun. 30, 2015.
International Preliminary Report on Patentability pertaining to PCT/US2013/073977 dated Mar. 18, 2014.
International Preliminary Report on Patentability pertaining to PCT/US2013/073979 dated Jul. 9, 2015.
International Preliminary Report on Patentability pertaining to PCT/US2013/073980 dated Jun. 30, 2015.
International Preliminary Report on Patentability pertaining to PCT/US2014/044374 dated Jan. 7, 2016.
International Preliminary Report on Patentability pertaining to PCT/US2014/044374 dated Dec. 29, 2015.
International Preliminary Report on Patentability pertaining to PCT/US2016/040568 dated Jan. 2, 2018.
International Preliminary Report on Patentability pertaining to PCT/US2016/040577 dated Jan. 2, 2018.
International Search Report and Written Opinion pertaining to PCT/US2013/073977 dated Jul. 9, 2015.
International Search Report and Written Opinion pertaining to PCT/US2013/073979 dated Mar. 18, 2014.
International Search Report and Written Opinion pertaining to PCT/US2013/073980 dated Mar. 18, 2014.
International Search Report and Written Opinion pertaining to PCT/US2013/073982 dated Mar. 18, 2014.
International Search Report and Written Opinion pertaining to PCT/US2014/044374 dated Aug. 28, 2014.
International Search Report and Written Opinion pertaining to PCT/US2016/040568 dated Sep. 26, 2016.
International Search Report and Written Opinion pertaining to PCT/US2016/040577 dated Sep. 30, 2016.
Japanese Office Action pertaining to Japan Patent Application No. 2015-550433 dated Jan. 9, 2018.
Japanese Office Action pertaining to Japan Patent Application No. 2015-550434 dated Jan. 9, 2018.
Monrabal et al., Macromol. Symp. 2007, 257, 71-79.
Yau, Wallace W., "Examples of Using 3D-GPC-TREF for Polyolefin Characterization", Macromol. Symp., 2007, 257, 29-45.
Zimm, Bruno H., Journal of Chemical Physics, vol. 16, 12, 1099-1116 (1948).
Office Action dated Apr. 16, 2018 pertaining to U.S. Appl. No. 15/357,931, 8 pages.
International Preliminary Report on Patentability pertaining to PCT/US2016/054088 dated Apr. 3, 2018.
International Preliminary Report on Patentability pertaining to PCT/US2016/054285 dated Apr. 3, 2018.
International Search Report and Written Opinion pertaining to PCT/US2016/054088 dated Dec. 19, 2016.
International Search Report and Written Opinion pertaining to PCT/US2016/054285 dated Dec. 21, 2016.
International Search Report pertaining to Application No. PCT/U2013/073976 dated Mar. 18, 2014.
International Preliminary Report on Patentability pertaining to PCT/US2013/073976 dated Jun. 30, 2015.

(56) References Cited

OTHER PUBLICATIONS

EPO Communication pursuant to Rules 161(1) and 162 EPC for counterpart EPO Application No. 13811736.1 dated Aug. 4, 2015.
B.G. Kyle, "Chemical and Process Thermodynamics", Third Edition, Prentice-Hall, 1999.
Georgio Soave, "Equilibrium constants from a modified Redlich-Kwong equation of state", Chemical Engineering Science, vol. 27, pp. 1197-1203, 1972.
Mourey et al., "Chromatography of Polymers", Chapter 12, pp. 180-198, 1992.
Blake et al., "Chromatography of Polymers", Chapter 13, pp. 199-219, 1992.
Chinese Office Action received Oct. 10, 2016 from Chinese Counterpart Application No. 201380067367.9 dated Aug. 19, 2016.
EP Response to Office Action dated Oct. 20, 2015; from EP Counterpart Application No. 13811736.1.
Chinese Office Action pertaining to Chinese Counterpart Application No. 201380067367.9 dated May 11, 2017.
Supplementary Examination Report pertaining to Singapore Counterpart Application No. 11201503581P dated Sep. 18, 2017.

* cited by examiner $$\% \text{ Crystallinity} = ((H_f)/(292 \text{ J/g})) \times 100$$

Equation 1

Fig. 1

$$g_i' = (IV_{Sample,i} / IV_{linear\ reference,j})$$

Equation 2

Fig. 2

$$\left[\frac{IV_{Sample,i}}{IV_{linear\_reference,j}}\right]^{1.33}_{M_{i=j}} = \left[\left(1+\frac{B_{n,i}}{7}\right)^{1/2} + \frac{4}{9}\frac{B_{n,i}}{\pi}\right]^{-1/2}$$

Equation 3

Fig. 3

$$LCBf = \frac{\sum_{M=3500}^{i}\left(\frac{B_{n,i}}{M_i/14000}c_i\right)}{\sum c_i}$$

Equation 4

Fig. 4

$$M_{PE} = \left(\frac{K_{PS}}{K_{PE}}\right)^{1/\alpha_{PE}+1} \cdot M_{PS}^{\alpha_{PS}+1/\alpha_{PE}+1}$$

Equation 5

Fig. 5

$$[\eta]_{PE} = K_{PS} \cdot M_{PS}^{\alpha+1} / M_{PE}$$

Equation 6

Fig. 6

$$M_W = \sum_i w_i M_i = \sum_i \left(\frac{C_i}{\sum_i C_i}\right) M_i = \frac{\sum_i C_i M_i}{\sum_i C_i} = \frac{\sum_i LS_i}{\sum_i C_i} = \frac{LS\ Area}{Conc.\ Area}$$

Equation 7

Fig. 7

$$IV = [\eta] = \sum_i w_i IV_i = \sum_i \left(\frac{C_i}{\sum_i C_i}\right) IV_i = \frac{\sum_i C_i IV_i}{\sum_i C_i} = \frac{\sum_i DP_i}{\sum_i C_i} = \frac{DP\ Area}{Conc.\ Area}$$

Equation 8

Fig. 8

$$Mw_{CC} = \sum_i \left( \frac{C_i}{\sum_i C_i} \right) M_i = \sum_i w_i M_i$$

Equation 9

Fig. 9

$$[\eta]_{CC} = \sum_i \left( \frac{C_i}{\sum_i C_i} \right) IV_i = \sum_i w_i IV_i$$

Equation 10

Fig. 10

$$gpcBR = \left[ \left( \frac{[\eta]_{CC}}{[\eta]} \right) \cdot \left( \frac{M_W}{M_{W,CC}} \right)^{\alpha_{PE}} - 1 \right]$$

Equation 11

Fig. 11

$$\text{Resolution} = \frac{\text{Peak temperature of NIST 1475a - Peak Temperature of Hexacontane}}{\text{Half-height Width of NIST 1475a + Half-height Width of Hexacontane}}$$

Equation 12

Fig. 12

$$CDC = \frac{Comonomer\ Distrubution\ Index}{Comonomer\ Distribution\ Shape\ Factor} = \frac{Comonomer\ Distribution\ Index}{Half\ Width/Stdev} * 100$$

Equation 13

Fig. 13

$$\int_{35}^{119.0} w_T(T)dT = 1$$

Equation 14

Fig. 14

$$\int_{35}^{T_{median}} w_T(T)dT = 0.5$$

Equation 15

Fig. 15

$$\ln(1 - comonomer content) = -\frac{207.26}{273.12 + T} + 0.5533$$
$$R^2 = 0.997$$

Equation 16

Fig. 16

$$Stdev = \sqrt{\sum_{35.0}^{119.0}(T-T_p)^2 * w_T(T)}$$

Equation 17

Fig. 17

$$ZSVR = \frac{\eta_{0B}}{\eta_{0L}}$$

Equation 18

Fig. 18

$$\eta_{0L} = 2.29 \times 10^{-15} M_{w-gpc}^{3.65}$$

Equation 19

Fig. 19

$$M_{polyethylene} = A(M_{polystyrene})^B$$

Equation 20

Fig. 20

CATALYST SYSTEMS FOR OLEFIN POLYMERIZATION

REFERENCE TO RELATED APPLICATIONS

The present application is a continuation of U.S. patent application Ser. No. 14/437,543, filed on Apr. 22, 2015, which is a national stage entry of PCT/US2013/073976, filed on Dec. 10, 2013, which claims the benefit of U.S. Provisional Application No. 61/746,151, filed on Dec. 27, 2012.

FIELD OF INVENTION

The instant invention relates to procatalysts and catalyst systems for olefin polymerization, olefin based polymers polymerized therewith, articles made from such polymers, and process for producing the same.

BACKGROUND OF THE INVENTION

Olefin based polymers such as polyethylene and/or polypropylene are produced via various catalyst systems. Selection of such catalyst system used in the polymerisation process of the olefin based polymers is an important factor contributing to the characteristics and properties of such olefin based polymers.

Polyethylene is known for use in the manufacture of a wide a variety of articles. The polyethylene polymerization process can be varied in a number of respects to produce a wide variety of resultant polyethylene resins having different physical properties that render the various resins suitable for use in different applications. It is generally known that polyethylene can be produced in solution phase loop reactors in which ethylene monomer, and optionally one or more alpha olefin comonomers, typically having from 3 to 10 carbon atoms, are circulated in the presence of one or more catalyst systems under pressure around a loop reactor by a circulation pump. The ethylene monomers and optional one or more comonomers are present in a liquid diluent, such as an alkane or isoalkane, for example isobutane. Hydrogen may also be added to the reactor. The catalyst systems for producing polyethylene may typically comprise a chromium-based catalyst system, a Ziegler Natta catalyst system, and/or a molecular (either metallocene or non-metallocene) catalyst system. The reactants in the diluent and the catalyst system are circulated at an elevated polymerization temperature around the loop reactor thereby producing polyethylene homopolymer and/or copolymer depending on whether or not one or more comonomers are present. Either periodically or continuously, part of the reaction mixture, including the polyethylene product dissolved n the diluent, together with unreacted ethylene and one or more optional comonomers, is removed from the loop reactor. The reaction mixture when removed from the loop reactor may be processed to remove the polyethylene product from the diluent and the unreacted reactants, with the diluent and unreacted reactants typically being recycled back into the loop reactor. Alternatively, the reaction mixture may be sent to a second reactor, e.g. loop reactor, serially connected to the first loop reactor where a second polyethylene fraction may be produced.

Despite the research efforts in developing catalyst systems suitable for polyolefin, such as polyethylene and/or polypropylene, polymerization, there is still a need for a procatalyst and a catalyst system exhibiting high selectivity toward ethylene at higher reaction temperatures; thus, facilitating the production of higher molecular weight polymers at relatively higher reaction temperatures. Additionally, despite the research efforts in developing polyolefins, such as polyethylene and/or polypropylene, with improved properties, there is still a need for a polyethylene having improved properties.

SUMMARY OF THE INVENTION

The instant invention provides procatalysts and catalyst systems for olefin polymerization, olefin based polymers polymerized therewith, and process for producing the same.

In one embodiment, the instant invention provides a procatalyst comprising a metal-ligand complex of formula (I):

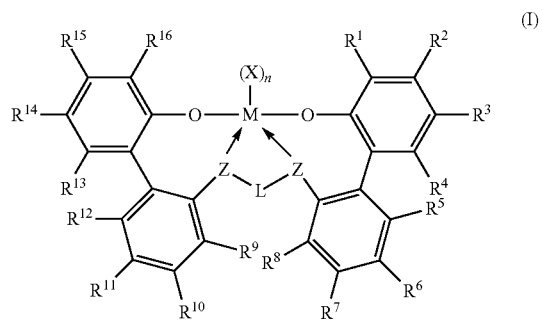

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (I) is, overall, neutral; and Each Z independently is O, S, $N(C_1\text{-}C_{40})$hydrocarbyl, or $P(C_1\text{-}C_{40})$hydrocarbyl; and L is $(C_3\text{-}C_{40})$hydrocarbylene or $(C_3\text{-}C_{40})$heterohydrocarbylene, wherein the $(C_3\text{-}C_{40})$hydrocarbylene has a portion that comprises a 3-carbon atom to 10-carbon atom linker backbone linking the Z atoms in formula (I) (to which L is bonded) and the $(C_3\text{-}C_{40})$heterohydrocarbylene has a portion that comprises a 3-atom to 10-atom linker backbone linking the Z atoms in formula (I), wherein each of the from 3 to 10 atoms of the 3-atom to 10-atom linker backbone of the $(C_3\text{-}C_{40})$heterohydrocarbylene independently is a carbon atom or heteroatom, wherein each heteroatom independently is O, S, S(O), $S(O)_2$, $Si(R^C)_2$, $Ge(R^C)_2$, $P(R^P)$, or $N(R^N)$, wherein independently each $R^C$ is $(C_1\text{-}C_{30})$hydrocarbyl, each $R^P$ is $(C_1\text{-}C_{30})$hydrocarbyl; and each $R^N$ is $(C_1\text{-}C_{30})$ hydrocarbyl or absent; and $R^{1\text{-}24}$ are selected from the group consisting of a $(C_1\text{-}C_{40})$ hydrocarbyl, $(C_1\text{-}C_{40})$heterohydrocarbyl, $Si(R^C)_3$, $Ge(R^C)_3$, $P(R^P)_2$, $N(R^N)_2$, $OR^C$, $SR^C$, $NO_2$, $CN$, $CF_3$, $R^CS(O)$—, $R^CS(O)_2$—, $(R^C)_2C$=N—, $R^CC(O)O$—, $R^COC(O)$—, $R^CC(O)N(R)$—, $(R^C)_2NC(O)$—, halogen atom, hydrogen atom, and combination thereof; and, wherein least $R^1$, $R^{16}$, or both comprise of formula (II), and preferably $R^1$ and $R^{16}$ are the same;

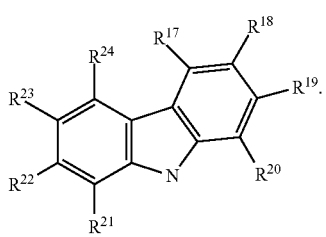

(II)

When $R^{22}$ is H, then $R^{19}$ is a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or When $R^{19}$ is H, then $R^{22}$ is a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or Preferably, $R^{22}$ and $R^{19}$ are both a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or When $R^8$ is H, then $R^9$ is a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or When $R^9$ is H, then $R^8$ is a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or Preferably, $R_8$ and $R_9$ are both a $(C_1-C_{40})$hydrocarbyl; $(C_1-C_{40})$heterohydrocarbyl; $Si(R^C)_3$, $Ge(R^C)_3$, $P(R^P)_2$, $N(R^N)_2$, $OR^C$, $SR^C$, $NO_2$, CN, $CF_3$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$ or halogen atom; and/or Optionally two or more R groups (for example, from $R^{9-15}$, $R^{9-13}$, $R^{9-12}$, $R^{2-8}$, $R^{4-8}$, $R^{5-8}$) can combine together into ring structures, with such ring structures having from 3 to 50 atoms in the ring excluding any hydrogen atoms.

Each of the the aryl, heteroaryl, hydrocarbyl, heterohydrocarbyl, $Si(R^C)_3$, $Ge(R^C)_3$, $P(R^P)_2$, $N(R^N)_2$, $OR^C$, $SR^C$, $R^CS(O)—$, $R^CS(O)_2—$, $(R^C)_2C=N—$, $R^CC(O)O—$, $R^COC(O)—$, $R^CC(O)N(R)—$, $(R^C)_2NC(O)—$, hydrocarbylene, and heterohydrocarbylene groups independently is unsubstituted or substituted with one or more $R^S$ substituents.

Each $R^S$ independently is a halogen atom, polyfluoro substitution, perfluoro substitution, unsubstituted $(C_1-C_{18})$ alkyl, $F_3C—$, $FCH_2O—$, $F_2HCO—$, $F_3CO—$, $R_3Si—$, $R_3Ge—$, $RO—$, RS—, $RS(O)—$, $RS(O)_2—$, $R_2P—$, $R_2N—$, $R_2C=N—$, NC—, RC(O)O—, ROC(O)—, RC(O)N(R)—, or $R_2NC(O)—$, or two of the $R^S$ are taken together to form an unsubstituted $(C_1-C_{18})$alkylene, wherein each R independently is an unsubstituted $(C_1-C_{18})$alkyl.

Optionally two or more R groups (for example, from $R^{17-24}$, $R^{17-20}$, $R^{20-24}$) can combine together into ring structures, with such ring structures having from 3 to 50 atoms in the ring excluding any hydrogen atoms.

In another embodiment, the instant invention provides a catalyst system comprising procatalyst comprising a metal-ligand complex of formula (I), as described above and one or more co-catalysts.

In another embodiment, the present invention provides an olefin based polymer comprising the polymerization reaction of one or more α-olefins in the presence of at least one or more inventive catalyst systems and optionally one or more other catalyst systems in one or more polymerization reactors, connected in parallel, series or combinations thereof.

In another embodiment, the present invention provides a method for producing an olefin based polymer composing the steps of: (1) providing at least one or more inventive catalyst systems and optionally one or more other catalyst systems; (2) polymerizing one or more α-olefins in the presence of the at least one or more inventive catalyst systems and optionally one or more other catalyst systems in one or more polymerization reactors, connected in parallel, series or combinations thereof; and (3) thereby producing an olefin based polymer.

In another embodiment, the present invention provides an article comprising the above-described inventive olefin based polymer.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIGS. 1-20 illustrate Formulae 1-20, respectively.

DETAILED DESCRIPTION OF THE INVENTION

The instant invention provides procatalysts and catalyst systems for olefin polymerization, olefin based polymers polymerized therewith, and process for producing the same.

The catalyst system according to the present invention comprises a procatalyst component and a cocatalyst component.

Pro-catalyst Component

The procatalyst component according the present invention comprises a metal-ligand complex of formula (I):

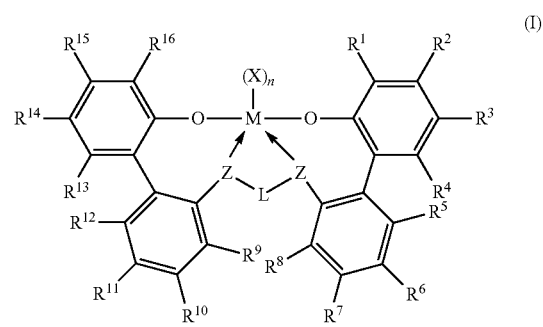

(I)

wherein:

M is titanium, zirconium, or hafnium, each independently being in a formal oxidation state of +2, +3, or +4; and n is an integer of from 0 to 3, and wherein when n is 0, X is absent; and Each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (I) is, overall, neutral; and Each Z independently is O, S, N($C_1$-$C_{40}$)hydrocarbyl, or P($C_1$-$C_{40}$)hydrocarbyl; and L is ($C_3$-$C_{40}$)hydrocarbylene or ($C_3$-$C_{40}$)heterohydrocarbylene, wherein the ($C_3$-$C_{40}$)hydrocarbylene has a portion that comprises a 3-carbon atom to 10-carbon atom linker backbone linking the Z atoms in formula (I) (to which L is bonded) and the $C_3$-$C_{40}$)heterohydrocarbylene has a portion that comprises a 3-atom to 10-atom linker backbone linking the Z atoms in formula (I), wherein each of the from 3 to 10 atoms of the 3-atom to 10-atom linker backbone of the ($C_3$-$C_{40}$)heterohydrocarbylene independently is a carbon atom or heteroatom, wherein each heteroatom independently is O, S, S(O), S(O)$_2$, Si($R^C$)$_2$, Ge($R^C$)$_2$, P($R^P$), or N($R^N$), wherein independently each $R^C$ is ($C_1$-$C_{30}$)hydrocarbyl, each $R^P$ is ($C_1$-$C_{30}$)hydrocarbyl; and each $R^N$ is ($C_1$-$C_{30}$) hydrocarbyl or absent; and $R^{1-24}$ are selected from the group consisting of a ($C_1$-$C_{40}$) hydrocarbyl, ($C_1$-$C_{40}$)heterohydrocarbyl, Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)—, halogen atom, hydrogen atom, and combination thereof.

$R^1$, $R^{16}$, or both comprise of formula (II), and preferably $R^1$ and $R^{16}$ are the same; and

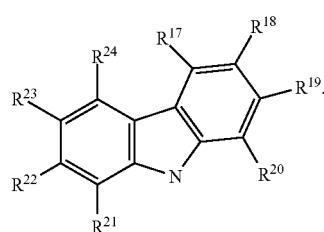

(II)

When $R^{22}$ is H, then $R^{19}$ is a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and When $R^{19}$ is H, then $R^{22}$ is a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and Preferably, $R^{22}$ and $R^{19}$ are both a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and When $R^8$ is H, then $R^9$ is a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and When $R^9$ is H, then $R^8$ is a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and Preferably, $R_8$ and $R_9$ are both a ($C_1$-$C_{40}$)hydrocarbyl; ($C_1$-$C_{40}$)heterohydrocarbyl; Si($R^C$)$_3$, Ge($R^C$)$_3$, P($R^P$)$_2$, N($R^N$)$_2$, OR$^C$, SR$^C$, NO$_2$, CN, CF$_3$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)— or halogen atom; and Optionally two or more R groups (from $R^{9-13}$ or $R^{4-8}$) can combine together into ring structures, with such ring structures having from 3 to 50 atoms in the ring excluding any hydrogen atoms.

Each of the the aryl, heteroaryl, hydrocarbyl, heterohydrocarbyl, Si($R^C$)$_3$, Ge($R^C$)$_3$, P($R^P$)$_2$, N($R^N$)$_2$, OR$^C$, SR$^C$, $R^C$S(O)—, $R^C$S(O)$_2$—, ($R^C$)$_2$C=N—, $R^C$C(O)O—, $R^C$OC(O)—, $R^C$C(O)N(R)—, ($R^C$)$_2$NC(O)—, hydrocarbylene, and heterohydrocarbylene groups independently is unsubstituted or substituted with one or more $R^S$ substituents; and Each $R^S$ independently is a halogen atom, polyfluoro substitution, perfluoro substitution, unsubstituted ($C_1$—$C_{18}$) alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the $R^S$ are taken together to form an unsubstituted ($C_1$-$C_{18}$)alkylene, wherein each R independently is an unsubstituted ($C_1$-$C_{18}$)alkyl.

Optionally two or more R groups (from $R^{20-24}$) can combine together into ring structures, with such ring structures having from 3 to 50 atoms in the ring excluding any hydrogen atoms.

As mentioned before, the present invention employs one or more metal-ligand complexes of formula (I), which is described herein using conventional chemical group terminology. When used to describe certain carbon atom-containing chemical groups (e.g., ($C_1$-$C_{40}$)alkyl), the parenthetical expression ($C_1$-$C_{40}$) can be represented by the form "($C_x$-$C_y$)," which means that the unsubstituted version of the chemical group comprises from a number x carbon atoms to a number y carbon atoms, wherein each x and y independently is an integer as described for the chemical group. The $R^S$ substituted version of the chemical group can contain more than y carbon atoms depending on nature of $R^S$. Thus, for example, an unsubstituted ($C_1$-$C_{40}$)alkyl contains from 1 to 40 carbon atoms (x=1 and y=40). When the chemical group is substituted by one or more carbon atom-containing $R^S$ substituents, the substituted ($C_x$-$C_y$) chemical group may comprise more than y total carbon atoms; i.e., the total number of carbon atoms of the carbon atom-containing substituent(s)-substituted ($C_x$-$C_y$) chemical group is equal to y plus the sum of the number of carbon atoms of each of the carbon atom-containing substituent(s). Any atom of a chemical group that is not specified herein is understood to be a hydrogen atom.

In some embodiments, each of the chemical groups (e.g., X, L, $R^{1-24}$, etc.) of the metal-ligand complex of formula (I) may be unsubstituted, that is, can be defined without use of a substituent $R^S$, provided the above-mentioned conditions are satisfied. In other embodiments, at least one of the chemical groups of the metal-ligand complex of formula (I) independently contain one or more of the substituents $R^S$. Preferably, accounting for all chemical groups, there are not more than a total of 20 $R^S$, more preferably not more than a total of 10 $R^S$, and still more preferably not more than a total of 5 $R^S$ in the metal-ligand complex of formula (I). Where the invention compound contains two or more substituents $R^S$, each $R^S$ independently is bonded to a same or different substituted chemical group. When two or more $R^S$ are bonded to a same chemical group, they independently are bonded to a same or different carbon atom or heteroatom, as the case may be, in the same chemical group up to and including persubstitution of the chemical group.

The term "persubstitution" means each hydrogen atom (H) bonded to a carbon atom or heteroatom of a corresponding unsubstituted compound or functional group, as the case may be, is replaced by a substituent (e.g., $R^S$). The term "polysubstitution" means each of at least two, but not all, hydrogen atoms (H) bonded to carbon atoms or heteroatoms of a corresponding unsubstituted compound or functional group, as the case may be, is replaced by a substituent (e.g., $R^S$). The ($C_1$-$C_{18}$)alkylene and ($C_1$-$C_8$)alkylene substituents are especially useful for forming substituted chemical groups that are bicyclic or tricyclic analogs, as the case may be, of corresponding monocyclic or bicyclic unsubstituted chemical groups.

As used herein, the term "($C_1$-$C_{40}$)hydrocarbyl" means a hydrocarbon radical of from 1 to 40 carbon atoms and the term "($C_1$-$C_{40}$)hydrocarbylene" means a hydrocarbon diradical of from 1 to 40 carbon atoms, wherein each hydrocarbon radical and diradical independently is aromatic (6 carbon atoms or more) or non-aromatic, saturated or unsaturated, straight chain or branched chain, cyclic (including mono- and poly-cyclic, fused and non-fused polycyclic, including bicyclic; 3 carbon atoms or more) or acyclic, or a combination of two or more thereof; and each hydrocarbon radical and diradical independently is the same as or different from another hydrocarbon radical and diradical, respectively, and independently is unsubstituted or substituted by one or more $R^S$.

Preferably, a ($C_1$-$C_{40}$)hydrocarbyl independently is an unsubstituted or substituted ($C_1$-$C_{40}$)alkyl, ($C_3$-$C_{40}$)cycloalkyl, ($C_3$-$C_{20}$)cycloalkyl-($C_1$-$C_{20}$)alkylene, ($C_6$-$C_{40}$)aryl, or ($C_6$-$C_{20}$)aryl-($C_1$-$C_{20}$)alkylene. More preferably, each of the aforementioned ($C_1$-$C_{40}$)hydrocarbyl groups independently has a maximum of 20 carbon atoms (i.e., ($C_1$-$C_{20}$)hydrocarbyl), and still more preferably a maximum of 12 carbon atoms.

The terms "($C_1$-$C_{40}$)alkyl" and "($C_1$-$C_{18}$)alkyl" mean a saturated straight or branched hydrocarbon radical of from 1 to 40 carbon atoms or from 1 to 18 carbon atoms, respectively, that is unsubstituted or substituted by one or more $R^S$. Examples of unsubstituted ($C_1$-$C_{40}$)alkyl are unsubstituted ($C_1$-$C_{20}$)alkyl; unsubstituted ($C_1$-$C_{10}$)alkyl; unsubstituted ($C_1$-$C_5$)alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{40}$)alkyl are substituted ($C_1$-$C_{20}$)alkyl, substituted ($C_1$-$C_{10}$)alkyl, trifluoromethyl, and ($C_{45}$)alkyl. The ($C_{45}$)alkyl is, for example, a ($C_{27}$-$C_{40}$)alkyl substituted by one $R^S$, which is a ($C_{18}$-$C_5$)alkyl, respectively. Preferably, each ($C_1$-$C_5$)alkyl independently is methyl, trifluoromethyl, ethyl, 1-propyl, 1-methylethyl, or 1,1-dimethylethyl.

The term "($C_6$-$C_{40}$)aryl" means an unsubstituted or substituted (by one or more $R^S$) mono-, bi- or tricyclic aromatic hydrocarbon radical of from 6 to 40 carbon atoms, of which at least from 6 to 14 of the carbon atoms are aromatic ring carbon atoms, and the mono-, bi- or tricyclic radical comprises 1, 2 or 3 rings, respectively; wherein the 1 ring is aromatic and the 2 or 3 rings independently are fused or non-fused and at least one of the 2 or 3 rings is aromatic. Examples of unsubstituted ($C_6$-$C_{40}$)aryl are unsubstituted ($C_6$-$C_{20}$)aryl; unsubstituted ($C_6$-$C_{18}$)aryl; 2-($C_1$-$C_5$)alkyl-phenyl; 2,4-bis($C_1$-$C_5$)alkyl-phenyl; phenyl; fluorenyl; tetrahydrofluorenyl; indacenyl; hexahydroindacenyl; indenyl; dihydroindenyl; naphthyl; tetrahydronaphthyl; and phenanthrene. Examples of substituted ($C_6$-$C_{40}$)aryl are substituted ($C_6$-$C_{20}$)aryl; substituted ($C_6$-$C_{18}$)aryl; 2,4-bis[($C_{20}$)alkyl]-phenyl; polyfluorophenyl; pentafluorophenyl; and fluoren-9-one-1-yl.

The term "($C_3$-$C_{40}$)cycloalkyl" means a saturated cyclic hydrocarbon radical of from 3 to 40 carbon atoms that is unsubstituted or substituted by one or more $R^S$. Other cycloalkyl groups (e.g., ($C_3$-$C_{12}$)alkyl)) are defined in an analogous manner. Examples of unsubstituted ($C_3$-$C_{40}$)cycloalkyl are unsubstituted ($C_3$-$C_{20}$)cycloalkyl, unsubstituted ($C_3$-$C_{10}$)cycloalkyl, cyclopropyl, cyclobutyl, cyclopentyl, cyclohexyl, cycloheptyl, cyclooctyl, cyclononyl, and cyclodecyl. Examples of substituted ($C_3$-$C_{40}$)cycloalkyl are substituted ($C_3$-$C_{20}$)cycloalkyl, substituted ($C_3$-$C_{10}$)cycloalkyl, cyclopentanon-2-yl, and 1-fluorocyclohexyl.

Examples of ($C_1$-$C_{40}$)hydrocarbylene are unsubstituted or substituted ($C_6$-$C_{40}$)arylene, ($C_3$-$C_{40}$)cycloalkylene, and ($C_1$-$C_{40}$)alkylene (e.g., ($C_1$-$C_{20}$)alkylene). In some embodiments, the diradicals are a same carbon atom (e.g., —$CH_2$—) or on adjacent carbon atoms (i.e., 1,2-diradicals), or are spaced apart by one, two, or more intervening carbon atoms (e.g., respective 1,3-diradicals, 1,4-diradicals, etc.). Preferred is a 1,2-, 1,3-, 1,4-, or an alpha,omega-diradical, and more preferably a 1,2-diradical. The alpha, omega-diradical is a diradical that has maximum carbon backbone spacing between the radical carbons. More preferred is a 1,2-diradical, 1,3-diradical, or 1,4-diradical version of ($C_6$-$C_{18}$)arylene, ($C_3$-$C_{20}$)cycloalkylene, or ($C_2$-$C_{20}$)alkylene.

The term "($C_1$-$C_{40}$)alkylene" means a saturated straight chain or branched chain diradical (i.e., the radicals are not on ring atoms) of from 1 to 40 carbon atoms that is unsubstituted or substituted by one or more $R^S$. Examples of unsubstituted ($C_1$-$C_{40}$)alkylene are unsubstituted ($C_1$-$C_{20}$)alkylene, including unsubstituted 1,2-($C_2$-$C_{10}$)alkylene; 1,3-($C_3$-$C_{10}$)alkylene; 1,4-($C_4$-$C_{10}$)alkylene;

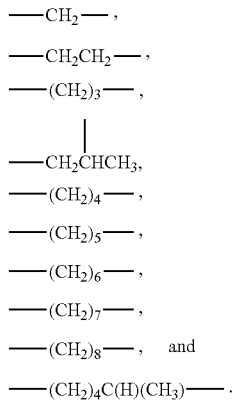

—$CH_2$—,
—$CH_2CH_2$—,
—$(CH_2)_3$—,
—$CH_2CHCH_3$,
—$(CH_2)_4$—,
—$(CH_2)_5$—,
—$(CH_2)_6$—,
—$(CH_2)_7$—,
—$(CH_2)_8$—, and
—$(CH_2)_4C(H)(CH_3)$—.

Examples of substituted ($C_1$-$C_{40}$)alkylene are substituted ($C_1$-$C_{20}$)alkylene, —$CF_2$—, —$C(O)$—, and —$(CH_2)_{14}C(CH_3)_2(CH_2)_5$— (i.e., a 6,6-dimethyl substituted normal-1,20-eicosylene). Since as mentioned previously two $R^S$ may be taken together to form a ($C_1$-$C_{18}$)alkylene, examples of substituted ($C_1$-$C_{40}$)alkylene also include 1,2-bis(methylene)cyclopentane, 1,2-bis(methylene)cyclohexane, 2,3-bis(methylene)-7,7-dimethyl-bicyclo[2.2.1]heptane, and 2,3-bis(methylene)bicyclo[2.2.2]octane.

The term "($C_3$-$C_{40}$)cycloalkylene" means a cyclic diradical (i.e., the radicals are on ring atoms) of from 3 to 40 carbon atoms that is unsubstituted or substituted by one or more $R^S$. Examples of unsubstituted ($C_3$-$C_{40}$)cycloalkylene are 1,3-cyclopropylene, 1,1-cyclopropylene, and 1,2-cyclohexylene. Examples of substituted ($C_3$-$C_{40}$)cycloalkylene are 2-oxo-1,3-cyclopropylene and 1,2-dimethyl-1,2-cyclohexylene.

The term "($C_1$-$C_{40}$)heterohydrocarbyl" means a heterohydrocarbon radical of from 1 to 40 carbon atoms and the term "$(C_1-C_{40})$heterohydrocarbylene means a heterohydrocarbon diradical of from 1 to 40 carbon atoms, and each heterohydrocarbon independently has one or more heteroatoms O; S; S(O); S(O)$_2$; Si(R$^C$)$_2$; Ge(R$^C$)$_2$; P(R$^P$); and N(R$^N$), wherein independently each R$^C$ is unsubstituted $(C_1-C_{18})$hydrocarbyl, each R$^P$ is unsubstituted $(C_1-C_{18})$hydrocarbyl; and each R$^N$ is unsubstituted $(C_1-C_{18})$hydrocarbyl or absent (e.g., absent when N comprises —N= or tri-carbon substituted N). The heterohydrocarbon radical and each of the heterohydrocarbon diradicals independently is on a carbon atom or heteroatom thereof, although preferably is on a carbon atom when bonded to a heteroatom in formula (I) or to a heteroatom of another heterohydrocarbyl or heterohydrocarbylene. Each $(C_1-C_{40})$heterohydrocarbyl and $(C_1-C_{40})$heterohydrocarbylene independently is unsubstituted or substituted (by one or more R$^S$), aromatic or non-aromatic, saturated or unsaturated, straight chain or branched chain, cyclic (including mono- and poly-cyclic, fused and non-fused polycyclic) or acyclic, or a combination of two or more thereof; and each is respectively the same as or different from another.

Preferably, the $(C_1-C_{40})$heterohydrocarbyl independently is unsubstituted or substituted $(C_1-C_{40})$heteroalkyl, $(C_1-C_{40})$hydrocarbyl-O—, $(C_1-C_{40})$hydrocarbyl-S—, $(C_1-C_{40})$hydrocarbyl-S(O)—, $(C_1-C_{40})$hydrocarbyl-S(O)$_2$—, $(C_1-C_{40})$hydrocarbyl-Si(R$^C$)$_2$—, $(C_1-C_{40})$hydrocarbyl-Ge(R$^C$)$_2$—, $(C_1-C_{40})$hydrocarbyl-N(R$^N$)—, $(C_1-C_{40})$hydrocarbyl-P(R$^P$)—, $(C_2-C_{40})$heterocycloalkyl, $(C_2-C_{19})$heterocycloalkyl-$(C_1-C_{20})$alkylene, $(C_3-C_{20})$cycloalkyl-$(C_1-C_{19})$heteroalkylene, $(C_2-C_{19})$heterocycloalkyl-$(C_1-C_{20})$heteroalkylene, $(C_1-C_{40})$heteroaryl, $(C_1-C_{19})$heteroaryl-$(C_1-C_{20})$alkylene, $(C_6-C_{20})$aryl-$(C_1-C_{19})$heteroalkylene, or $(C_1-C_{19})$heteroaryl-$(C_1-C_{20})$heteroalkylene. The term "$(C_4-C_{40})$heteroaryl" means an unsubstituted or substituted (by one or more R$^S$) mono-, bi- or tricyclic heteroaromatic hydrocarbon radical of from 1 to 40 total carbon atoms and from 1 to 4 heteroatoms, and the mono-, bi- or tricyclic radical comprises 1, 2 or 3 rings, respectively, wherein the 2 or 3 rings independently are fused or non-fused and at least one of the 2 or 3 rings is heteroaromatic. Other heteroaryl groups (e.g., $(C_4-C_{12})$heteroaryl)) are defined in an analogous manner. The monocyclic heteroaromatic hydrocarbon radical is a 5-membered or 6-membered ring. The 5-membered ring has from 1 to 4 carbon atoms and from 4 to 1 heteroatoms, respectively, each heteroatom being O, S, N, or P, and preferably O, S, or N. Examples of 5-membered ring heteroaromatic hydrocarbon radical are pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; and tetrazol-5-yl. The 6-membered ring has 4 or 5 carbon atoms and 2 or 1 heteroatoms, the heteroatoms being N or P, and preferably N. Examples of 6-membered ring heteroaromatic hydrocarbon radical are pyridine-2-yl; pyrimidin-2-yl; and pyrazin-2-yl. The bicyclic heteroaromatic hydrocarbon radical preferably is a fused 5,6- or 6,6-ring system. Examples of the fused 5,6-ring system bicyclic heteroaromatic hydrocarbon radical are indol-1-yl; and benzimidazole-1-yl. Examples of the fused 6,6-ring system bicyclic heteroaromatic hydrocarbon radical are quinolin-2-yl; and isoquinolin-1-yl. The tricyclic heteroaromatic hydrocarbon radical preferably is a fused 5,6,5-; 5,6,6-; 6,5,6-; or 6,6,6-ring system. An example of the fused 5,6,5-ring system is 1,7-dihydropyrrolo[3,2-f]indol-1-yl. An example of the fused 5,6,6-ring system is 1H-benzo[f]indol-1-yl. An example of the fused 6,5,6-ring system is 9H-carbazol-9-yl. An example of the fused 6,6,6-ring system is acrydin-9-yl.

In some embodiments the $(C_4-C_{40})$heteroaryl is 2,7-disubstituted carbazolyl or 3,6-disubstituted carbazolyl, more preferably wherein each R$^S$ independently is phenyl, methyl, ethyl, isopropyl, or tertiary-butyl, still more preferably 2,7-di(tertiary-butyl)-carbazolyl, 3,6-di(tertiary-butyl)-carbazolyl, 2,7-di(tertiary-octyl)-carbazolyl, 3,6-di(tertiary-octyl)-carbazolyl, 2,7-diphenylcarbazolyl, 3,6-diphenylcarbazolyl, 2,7-bis(2,4,6-trimethylphenyl)-carbazolyl or 3,6-bis(2,4,6-trimethylphenyl)-carbazolyl.

The aforementioned heteroalkyl and heteroalkylene groups are saturated straight or branched chain radicals or diradicals, respectively, containing $(C_1-C_{40})$ carbon atoms, or fewer carbon atoms as the case may be, and one or more of the heteroatoms Si(R$^C$)$_2$, Ge(R$^C$)$_2$, P(R$^P$), N(R$^N$), N, O, S, S(O), and S(O)$_2$ as defined above, wherein each of the heteroalkyl and heteroalkylene groups independently are unsubstituted or substituted by one or more R$^S$.

Examples of unsubstituted $(C_2-C_{40})$heterocycloalkyl are unsubstituted $(C_2-C_{20})$heterocycloalkyl, unsubstituted $(C_2-C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thio-cyclononyl, and 2-aza-cyclodecyl.

The term "halogen atom" means fluorine atom (F), chlorine atom (Cl), bromine atom (Br), or iodine atom (I) radical. Preferably each halogen atom independently is the Br, F, or Cl radical, and more preferably the F or Cl radical. The term "halide" means fluoride (F$^-$), chloride (Cl$^-$), bromide (Br$^-$), or iodide (I$^-$) anion.

Unless otherwise indicated herein the term "heteroatom" means O, S, S(O), S(O)$_2$, Si(R$^C$)$_2$, Ge(R$^C$)$_2$, P(R$^P$), or N(R$^N$), wherein independently each R$^C$ is unsubstituted $(C_1-C_{18})$hydrocarbyl, each R$^P$ is unsubstituted $(C_1-C_{18})$hydrocarbyl; and each R$^N$ is unsubstituted $(C_1-C_{18})$hydrocarbyl or absent (absent when N comprises —N=). Preferably there is no germanium (Ge) atom in the invention compound or complex.

Preferably, there are no O—O, S—S, or O—S bonds, other than O—S bonds in an S(O) or S(O)$_2$ diradical functional group, in the metal-ligand complex of formula (I). More preferably, there are no O—O, N—N, P—P, N—P, S—S, or O—S bonds, other than O—S bonds in an S(O) or S(O)$_2$ diradical functional group, in the metal-ligand complex of formula (I).

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents R$^S$, one or more double and/or triple bonds optionally may or may not be present in substituents R$^S$. The term "unsaturated" means containing one or more carbon-carbon double bonds, carbon-carbon triple bonds, and (in heteroatom-containing groups) carbon-nitrogen, carbon-phosphorous, and carbon-silicon double bonds, not including any such double bonds that may be present in substituents R$^S$, if any, or in (hetero)aromatic rings, if any.

M is titanium, zirconium, or hafnium. In one embodiment, M is zirconium or hafnium, and in another embodiment M is hafnium. In some embodiments, M is in a formal oxidation state of +2, +3, or +4. In some embodiments, n is 0, 1, 2, or 3. Each X independently is a monodentate ligand that is neutral, monoanionic, or dianionic; or two Xs are taken together to form a bidentate ligand that is neutral, monoanionic, or dianionic. X and n are chosen in such a way that the metal-ligand complex of formula (I) is, overall, neutral. In some embodiments each X independently is the monodentate ligand. In one embodiment when there are two or more X monodentate ligands, each X is the same. In some embodiments the monodentate ligand is the monoanionic ligand. The monoanionic ligand has a net formal oxidation state of −1. Each monoanionic ligand may independently be hydride, $(C_1-C_{40})$hydrocarbyl carbanion, $(C_1-C_{40})$heterohydrocarbyl carbanion, halide, nitrate, carbonate, phosphate, sulfate, $HC(O)O^-$, $(C_1-C_{40})$hydrocarbylC(O)O$^-$, $HC(O)N(H)^-$, $(C_1-C_{40})$hydrocarbylC(O)N(H)$^-$, $(C_1-C_{40})$hydrocarbylC(O)N((C_1-C_{20})$hydrocarbyl)$^-$, $R^KR^LB^-$, $R^KR^LN^-$, $R^KO^-$, $R^KS^-$, $R^KR^LP^-$, or $R^MR^KR^LSi^-$, wherein each $R^K$, $R^L$, and $R^M$ independently is hydrogen, $(C_1-C_{40})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene and $R^M$ is as defined above.

In some embodiments at least one monodentate ligand of X independently is the neutral ligand. In one embodiment, the neutral ligand is a neutral Lewis base group that is $R^XNR^KR^L$, $R^KOR^L$, $R^KSR^L$, or $R^XPR^KR^L$, wherein each $R^X$ independently is hydrogen, $(C_1-C_{40})$hydrocarbyl, [$(C_1-C_{10})$hydrocarbyl]$_3$Si, [$(C_1-C_{10})$hydrocarbyl]$_3$Si$(C_1-C_{10})$hydrocarbyl, or $(C_1-C_{40})$heterohydrocarbyl and each $R^K$ and $R^L$ independently is as defined above.

In some embodiments, each X is a monodentate ligand that independently is a halogen atom, unsubstituted $(C_1-C_{20})$hydrocarbyl, unsubstituted $(C_1-C_{20})$hydrocarbylC(O)O—, or $R^KR^LN$— wherein each of $R^K$ and $R^L$ independently is an unsubstituted $(C_1-C_{20})$hydrocarbyl. In some embodiments each monodentate ligand X is a chlorine atom, $(C_1-C_{10})$hydrocarbyl (e.g., $(C_1-C_6)$alkyl or benzyl), unsubstituted $(C_1-C_{10})$hydrocarbylC(O)O—, or $R^KR^LN$— wherein each of $R^K$ and $R^L$ independently is an unsubstituted $(C_1-C_{10})$hydrocarbyl.

In some embodiments there are at least two X and the two X are taken together to form the bidentate ligand. In some embodiments the bidentate ligand is a neutral bidentate ligand. In one embodiment, the neutral bidentate ligand is a diene of formula $(R^D)_2C=C(R^D)-C(R^D)=C(R^D)_2$, wherein each $R^D$ independently is H, unsubstituted $(C_1-C_6)$alkyl, phenyl, or naphthyl. In some embodiments the bidentate ligand is a monoanionic-mono(Lewis base) ligand. The monoanionic-mono(Lewis base) ligand may be a 1,3-dionate of formula (D): $R^E-C(O^-)=CH-C(=O)-R^E$ (D), wherein each $R^D$ independently is H, unsubstituted $(C_1-C_6)$alkyl, phenyl, or naphthyl. In some embodiments the bidentate ligand is a dianionic ligand. The dianionic ligand has a net formal oxidation state of −2. In one embodiment, each dianionic ligand independently is carbonate, oxalate (i.e., $^-O_2CC(O)O^-$), $(C_2-C_{40})$hydrocarbylene dicarbanion, $(C_1-C_{40})$heterohydrocarbylene dicarbanion, phosphate, or sulfate.

As previously mentioned, number and charge (neutral, monoanionic, dianionic) of X are selected depending on the formal oxidation state of M such that the metal-ligand complex of formula (I) is, overall, neutral.

In some embodiments each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments n is 2 and each X is the same.

In some embodiments at least two X are different. In some embodiments n is 2 and each X is a different one of methyl; ethyl; 1-propyl; 2-propyl; 1-butyl; 2,2,-dimethylpropyl; trimethylsilylmethyl; phenyl; benzyl; and chloro.

The integer n indicates number of X. In one embodiment, n is 2 or 3 and at least two X independently are monoanionic monodentate ligands and a third X, if present, is a neutral monodentate ligand. In some embodiments n is 2 and two X are taken together to form a bidentate ligand. In some embodiments, the bidentate ligand is 2,2-dimethyl-2-silapropane-1,3-diyl or 1,3-butadiene.

Each Z independently is O, S, $N(C_1-C_{40})$hydrocarbyl, or $P(C_1-C_{40})$hydrocarbyl. In some embodiments each Z is different. In some embodiments one Z is O and one Z is $NCH_3$. In some embodiments one Z is O and one Z is S. In some embodiments one Z is S and one Z is $N(C_1-C_{40})$hydrocarbyl (e.g., $NCH_3$). In some embodiments each Z is the same. In some embodiments each Z is O. In some embodiments each Z is S. In some embodiments each Z is $N(C_1-C_{40})$hydrocarbyl (e.g., $NCH_3$). In some embodiments at least one, and in some embodiments each Z is $P(C_1-C_{40})$hydrocarbyl (e.g., $PCH_3$).

L is $(C_3-C_{40})$hydrocarbylene or (3 to 40 atom, wherein such atom is not H)heterohydrocarbylene, wherein the $(C_3-C_{40})$hydrocarbylene has a portion that comprises a 3-carbon atom to 10-carbon atom linker backbone linking the Z atoms in formula (I) (to which L is bonded) and the (3 to 40 atom, wherein such atom is not H)heterohydrocarbylene has a portion that comprises a 3-atom to 10-atom linker backbone linking the Z atoms in formula (I), wherein each of the from 3 to 10 atoms of the 3-atom to 10-atom linker backbone of the (3 to 40 atom, wherein such atom is not H)heterohydrocarbylene independently is a carbon atom or heteroatom, wherein each heteroatom independently is $C(R^C)_2$, O, S, S(O), $S(O)_2$, $Si(R^C)_2$, $Ge(R^C)_2$, $P(R^P)$, or $N(R^N)$, wherein independently each $R^C$ is $(C_1-C_{30})$hydrocarbyl, each $R^P$ is $(C_1-C_{30})$hydrocarbyl; and each $R^N$ is $(C_1-C_{30})$hydrocarbyl or absent. In some embodiments L is the $(C_3-C_{40})$hydrocarbylene. Preferably the aforementioned portion that comprises a 3-carbon atom to 10-carbon atom linker backbone of the $(C_3-C_{40})$hydrocarbylene of L comprises a 3-carbon atom to 10-carbon atom, and more preferably a 3-carbon atom or 4-carbon atom linker backbone linking the Z atoms in formula (I) to which L is bonded. In some embodiments L comprises the 3-carbon atom linker backbone (e.g., L is —CH$_2$CH$_2$CH$_2$—; —CH(CH$_3$)CH$_2$CH(CH$_3$)—; —CH(CH$_3$)CH(CH$_3$)CH(CH$_3$)—; —CH$_2$C(CH$_3$)$_2$CH$_2$—); 1,3-cyclopentane-diyl; or 1,3-cyclohexane-diyl. In some embodiments L comprises the 4-carbon atom linker backbone (e.g., L is —CH$_2$CH$_2$CH$_2$CH$_2$—; —CH$_2$C(CH$_3$)$_2$C(CH$_3$)$_2$CH$_2$—; 1,2-bis(methylene)cyclohexane; or 2,3-bis(methylene)-bicyclco[2.2.2]octane). In some embodiments L comprises the 5-carbon atom linker backbone (e.g., L is —CH$_2$CH$_2$CH$_2$CH$_2$CH$_2$— or 1,3-bis(methylene)cyclohexane). In some embodiments L comprises the 6-carbon atom linker backbone (e.g., L is —CH$_2$CH$_2$CH$_2$CH$_2$CH$_2$CH$_2$— or 1,2-bis(ethylene)cyclohexane).

In some embodiments, L is the $(C_3-C_{40})$hydrocarbylene and the $(C_3-C_{40})$hydrocarbylene of L is a $(C_3-C_{12})$hydrocarbylene, and more preferably $(C_3-C_8)$hydrocarbylene. In some embodiments the $(C_3-C_{40})$hydrocarbylene is an unsubstituted $(C_3-C_{40})$alkylene. In some embodiments the $(C_3-C_{40})$hydrocarbylene is a substituted $(C_3-C_{40})$alkylene. In some embodiments the $(C_3-C_{40})$hydrocarbylene is an unsubstituted $(C_3-C_{40})$cycloalkylene or substituted $(C_3-C_{40})$cycloalkylene, wherein each substituent independently is $R^S$, wherein preferably the $R^S$ independently is $(C_1-C_4)$alkyl.

In some embodiments L is the unsubstituted $(C_3-C_{40})$alkylene, and in some other embodiments, L is an acyclic unsubstituted $(C_3-C_{40})$alkylene, and still more preferably the acyclic unsubstituted (C$_2$-C$_{40}$)alkylene is, —CH$_2$CH$_2$CH$_2$—, cis —CH(CH$_3$)CH$_2$CH(CH$_3$)—, trans —CH(CH$_3$)CH$_2$CH(CH$_3$)—, —CH(CH$_3$)CH$_2$CH(CH$_3$)$_2$—, —CH(CH$_3$)CH(CH$_3$)CH(CH$_3$)—, —CH$_2$C(CH$_3$)$_2$CH$_2$—, —CH$_2$CH$_2$CH$_2$CH$_2$—, or —CH$_2$C(CH$_3$)$_2$C(CH$_3$)$_2$CH$_2$—. In some embodiments L is trans-1,2-bis(methylene)cyclopentane, cis-1,2-bis(methylene)cyclopentane, trans-1,2-bis(methylene)cyclohexane, or cis-1,2-bis(methylene)cyclohexane. In some embodiments the (C$_1$-C$_{40}$)alkylene-substituted (C$_1$-C$_{40}$)alkylene is exo-2,3-bis(methylene)bicyclo[2.2.2]octane or exo-2,3-bis(methylene)-7,7-dimethyl-bicyclo[2.2.1]heptane. In some embodiments L is the unsubstituted (C$_3$-C$_{40}$)cycloalkylene, and in some other embodiments, L is cis-1,3-cyclopentane-diyl or cis-1,3-cyclohexane-diyl. In some embodiments L is the substituted (C$_3$-C$_{40}$)cycloalkylene, and more preferably L is a (C$_1$-C$_{40}$) alkylene-substituted (C$_3$-C$_{40}$)cycloalkylene, and in some other embodiments, L is the (C$_1$-C$_{40}$)alkylene-substituted (C$_3$-C$_{40}$)cycloalkylene that is exo-bicyclo[2.2.2]octan-2,3-diyl.

In some embodiments L is the (3 to 40 atoms)heterohydrocarbylene. In some embodiments, the aforementioned portion that comprises a 3-atom to 6-atom linker backbone of the (3 to 40 atoms)heterohydrocarbylene of L comprises a from 3-atom to 5-atom, and in some other embodiments a 3-atom or 4-atom linker backbone linking the Z atoms in formula (I) to which L is bonded. In some embodiments L comprises the 3-atom linker backbone (e.g., L is —CH$_2$CH$_2$CH(OCH$_3$)—, —CH$_2$Si(CH$_3$)$_2$CH$_2$—, or —CH$_2$Ge(CH$_3$)$_2$CH$_2$—). The "—CH$_2$Si(CH$_3$)$_2$CH$_2$—" may be referred to herein as a 1,3-diradical of 2,2-dimethyl-2-silapropane. In some embodiments L comprises the 4-atom linker backbone (e.g., L is —CH$_2$CH$_2$OCH$_2$— or —CH$_2$P(CH$_3$)CH$_2$CH$_2$—). In some embodiments L comprises the 5-atom linker backbone (e.g., L is —CH$_2$CH$_2$OCH$_2$CH$_2$— or —CH$_2$CH$_2$N(CH$_3$)CH$_2$CH$_2$—). In some embodiments L comprises the 6-atom linker backbone (e.g., L is —CH$_2$CH$_2$C(OCH$_3$)$_2$CH$_2$CH$_2$CH$_2$—, —CH$_2$CH$_2$CH$_2$S(O)$_2$CH$_2$CH$_2$—, or —CH$_2$CH$_2$S(O)CH$_2$CH$_2$CH$_2$—). In some embodiments each of the from 3 to 6 atoms of the 3-atom to 6-atom linker backbone is a carbon atom. In some embodiments at least one heteroatom is the C(R$^C$)$_2$. In some embodiments at least one heteroatom is the Si(R$^C$)$_2$. In some embodiments at least one heteroatom is the O. In some embodiments at least one heteroatom is the N(R$^N$). In some embodiments, there are no O—O, S—S, or O—S bonds, other than O—S bonds in the S(O) or S(O)$_2$ diradical functional group, in -Z-L-Z-. In some other embodiments, there are no O—O, N—N, P—P, N—P, S—S, or O—S bonds, other than O—S bonds in an S(O) or S(O)$_2$ diradical functional group, in -Z-L-Z-. In some embodiments, the (3 to 40 atoms)heterohydrocarbylene is (3 to 11 atoms, excluding H)heterohydrocarbylene, and in some other embodiments (3 to 7 atoms)heterohydrocarbylene. In some embodiments the (3 to 7 atoms)heterohydrocarbylene of L is —CH$_2$Si(CH$_3$)$_2$CH$_2$—; —CH$_2$CH$_2$Si(CH$_3$)$_2$CH$_2$—; or CH$_2$Si(CH$_3$)$_2$CH$_2$CH$_2$—. In some embodiments, the (C$_1$-C$_7$)heterohydrocarbylene of L is —CH$_2$Si(CH$_3$)$_2$CH$_2$—, —CH$_2$Si(CH$_2$CH$_3$)$_2$CH$_2$—, —CH$_2$Si(isopropyl)$_2$CH$_2$—, —CH$_2$Si(tetramethylene)CH$_2$—, or —CH$_2$Si(pentamethylene)CH$_2$—. The —CH$_2$Si(tetramethylene)CH$_2$— is named 1-silacyclopentan-1,1-dimethylene. The —CH$_2$Si(pentamethylene)CH$_2$— is named 1-silacyclohexan-1,1-dimethylene.

In some embodiments the metal-ligand complex of formula (I) is a metal-ligand complex of any one of the following formulas:

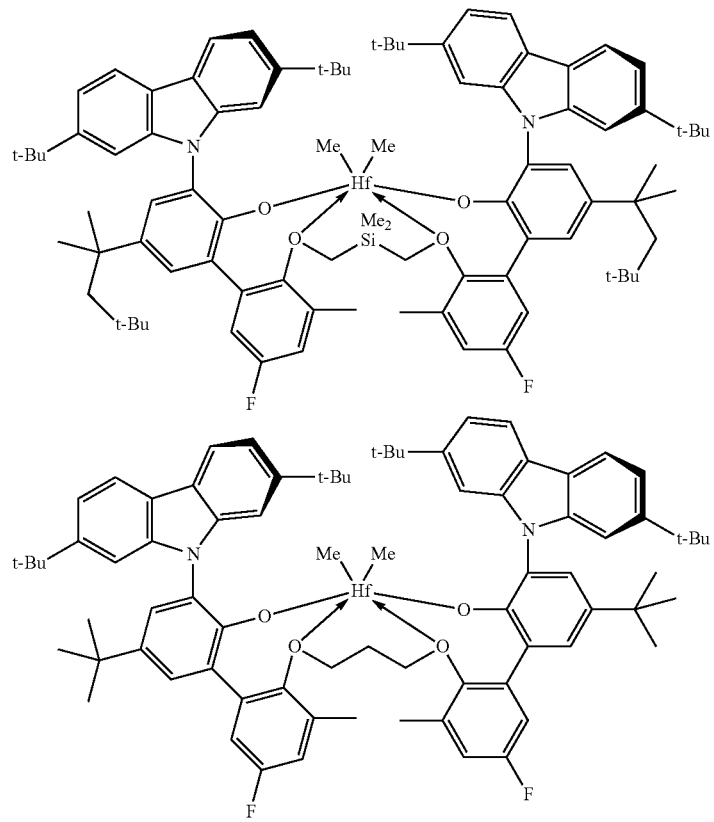

-continued
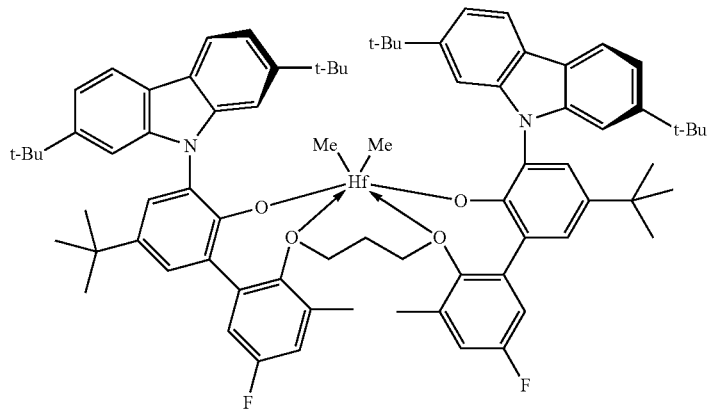
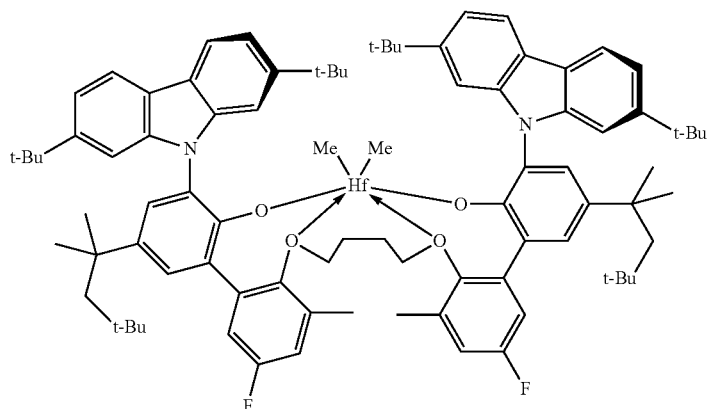
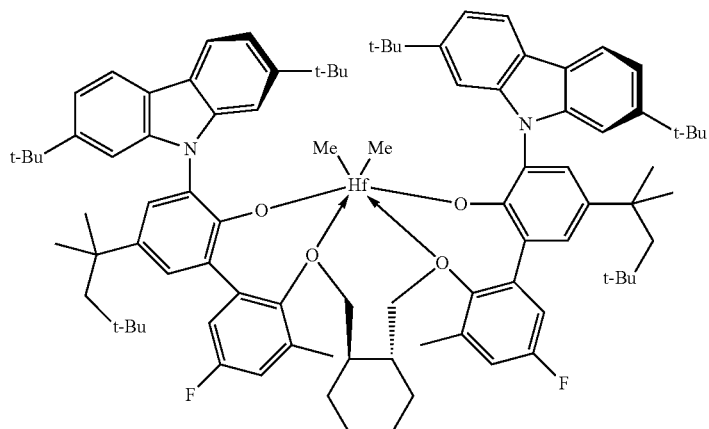
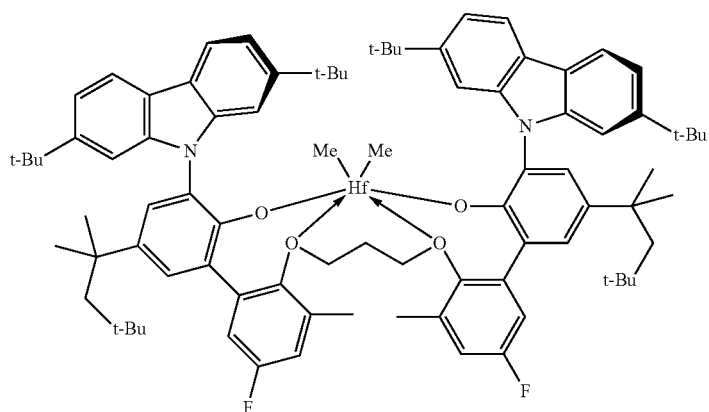

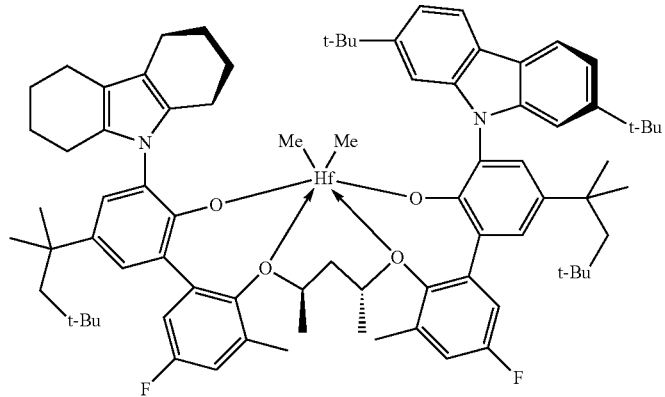
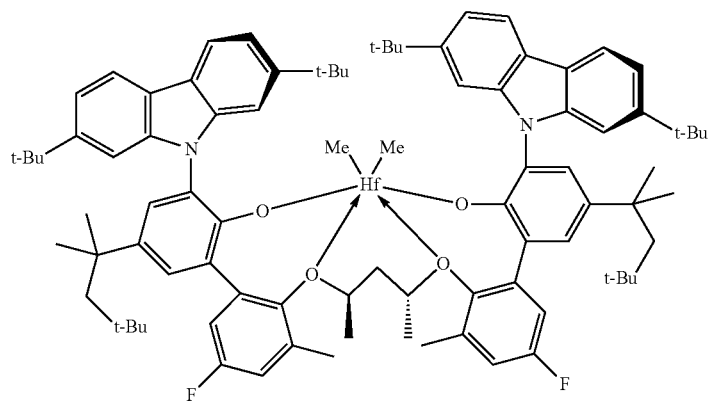
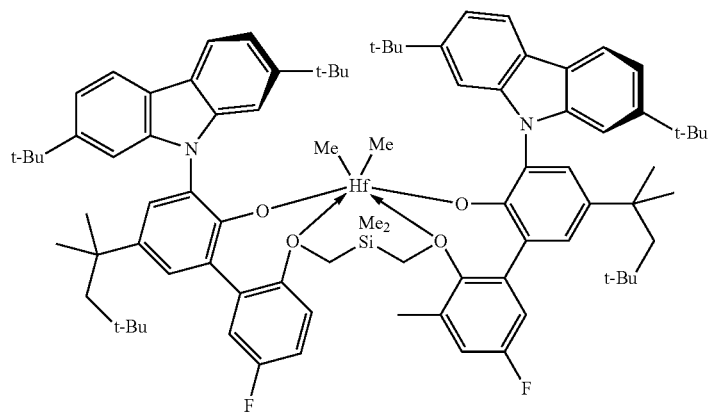
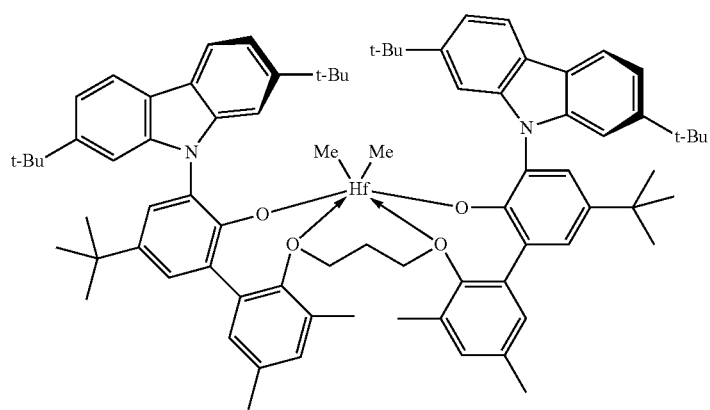

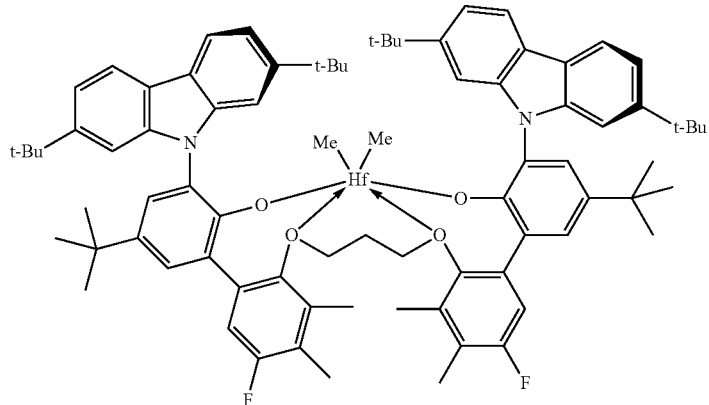
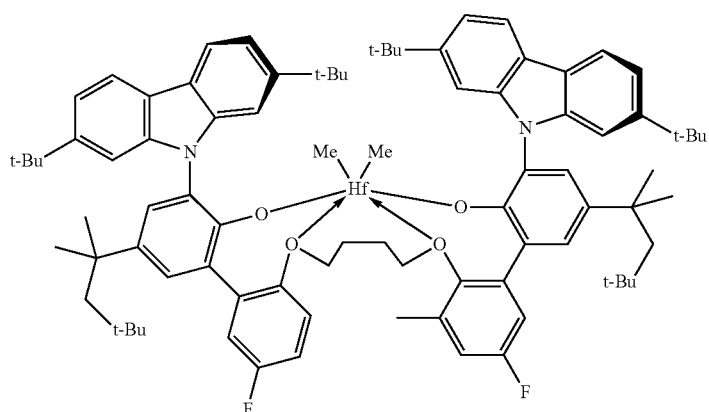
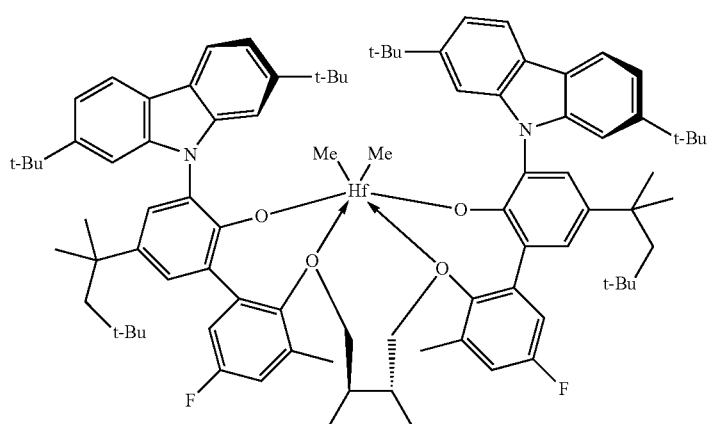
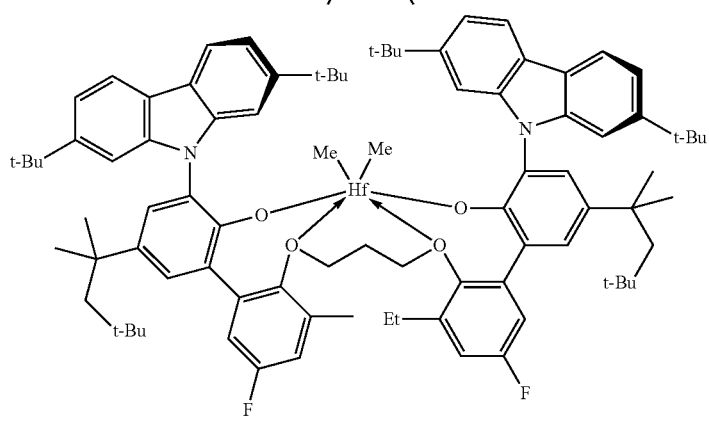

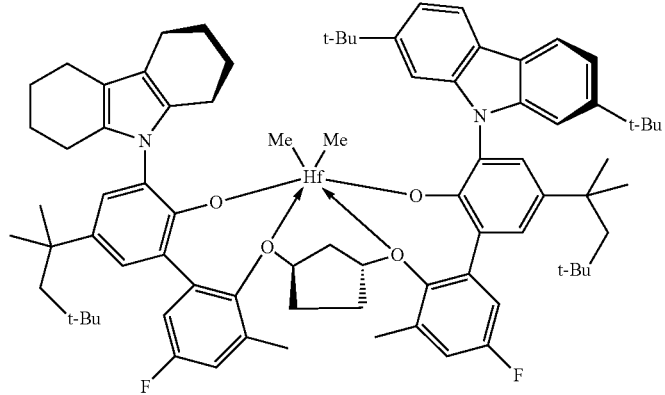
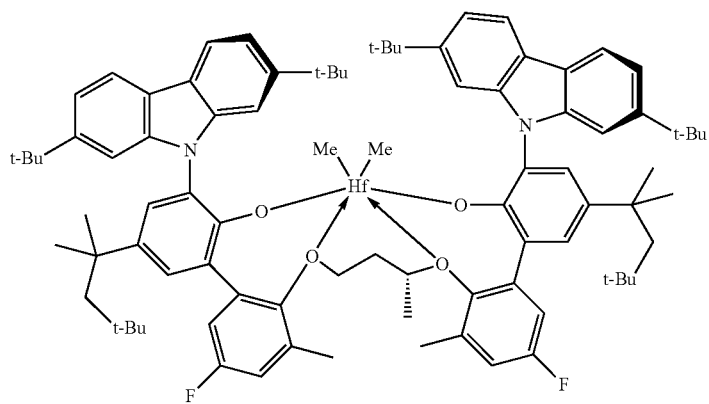
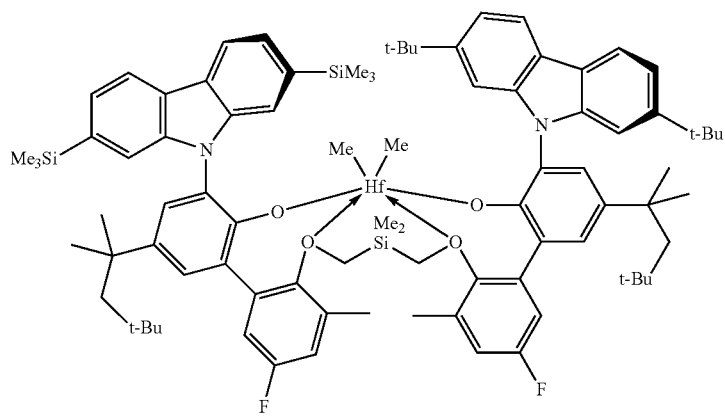
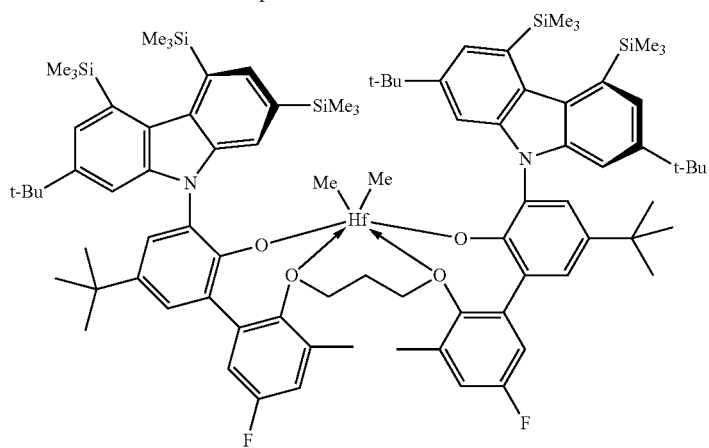

-continued
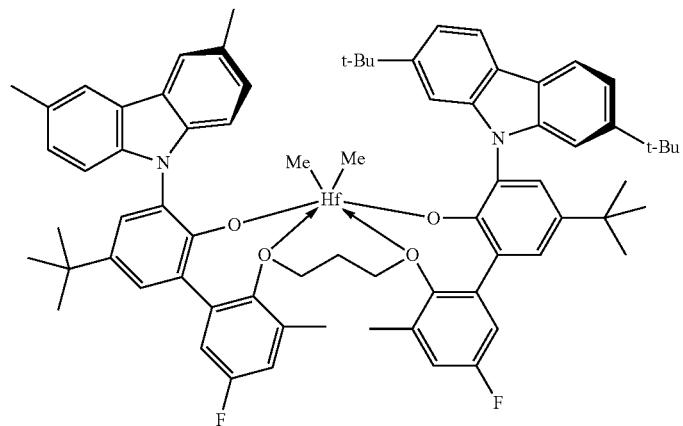
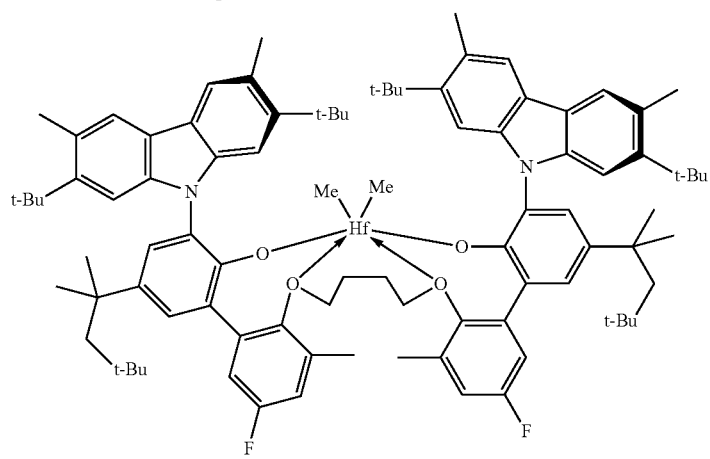
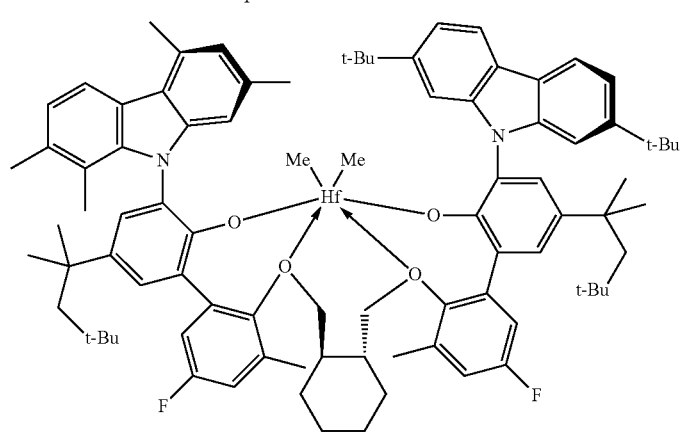
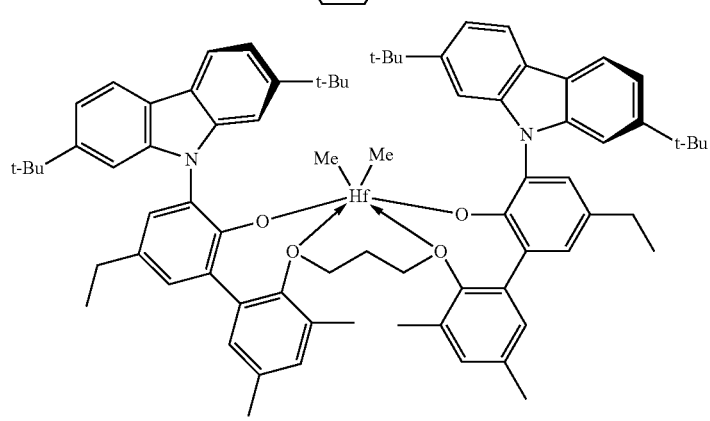

-continued
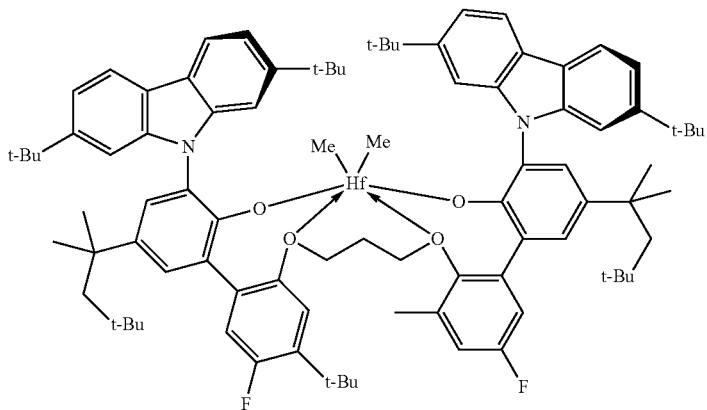
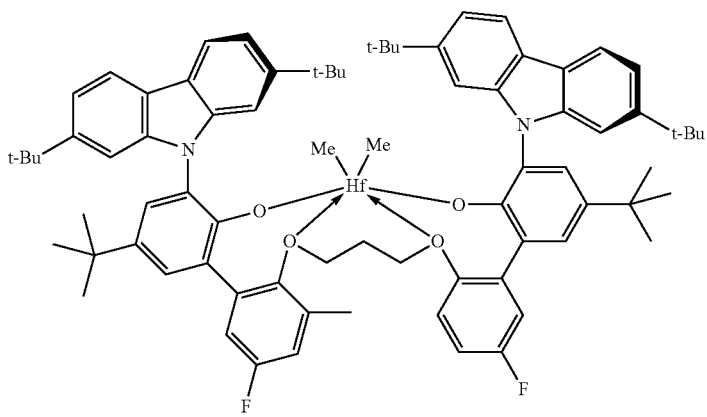
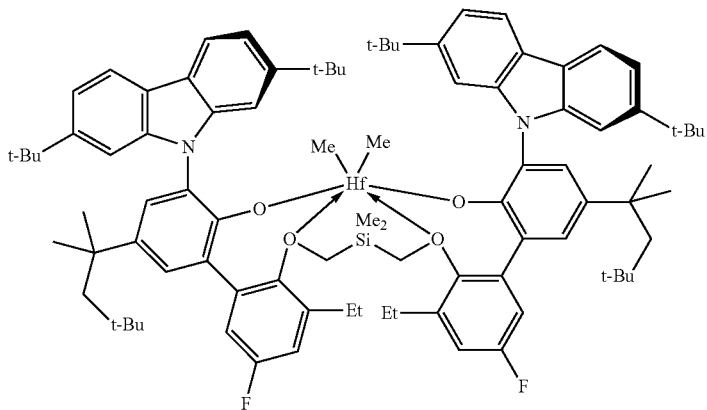
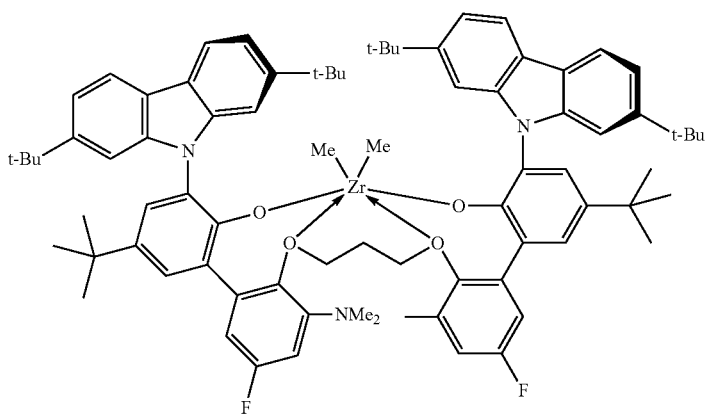

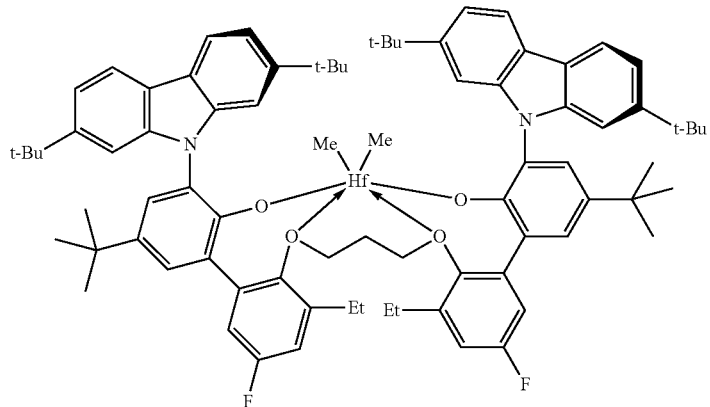
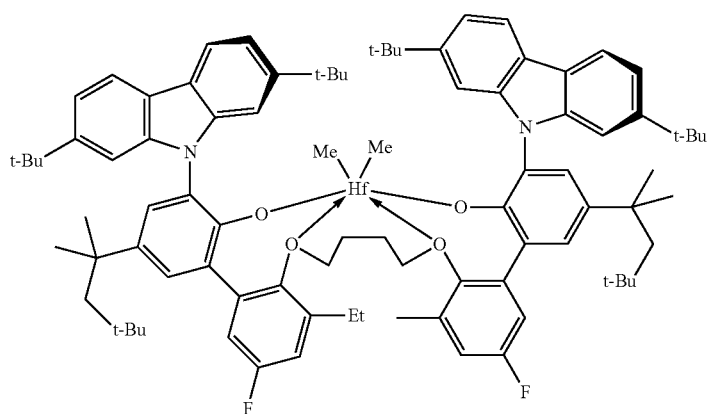
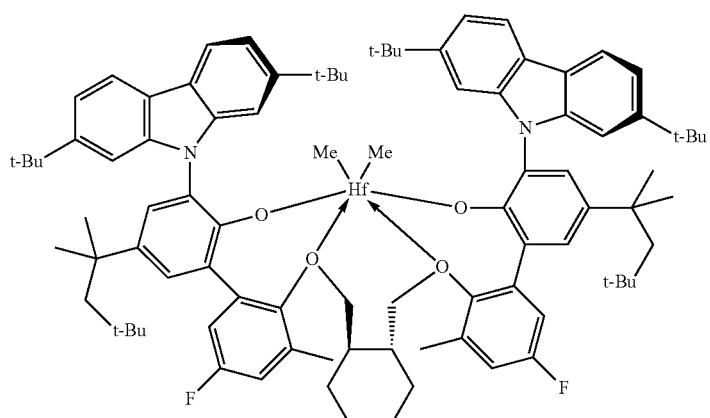
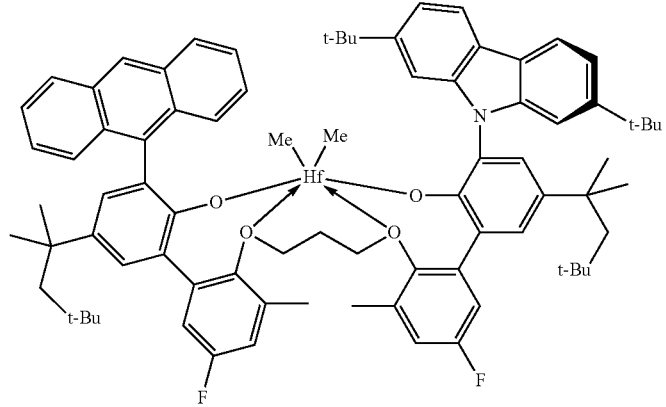

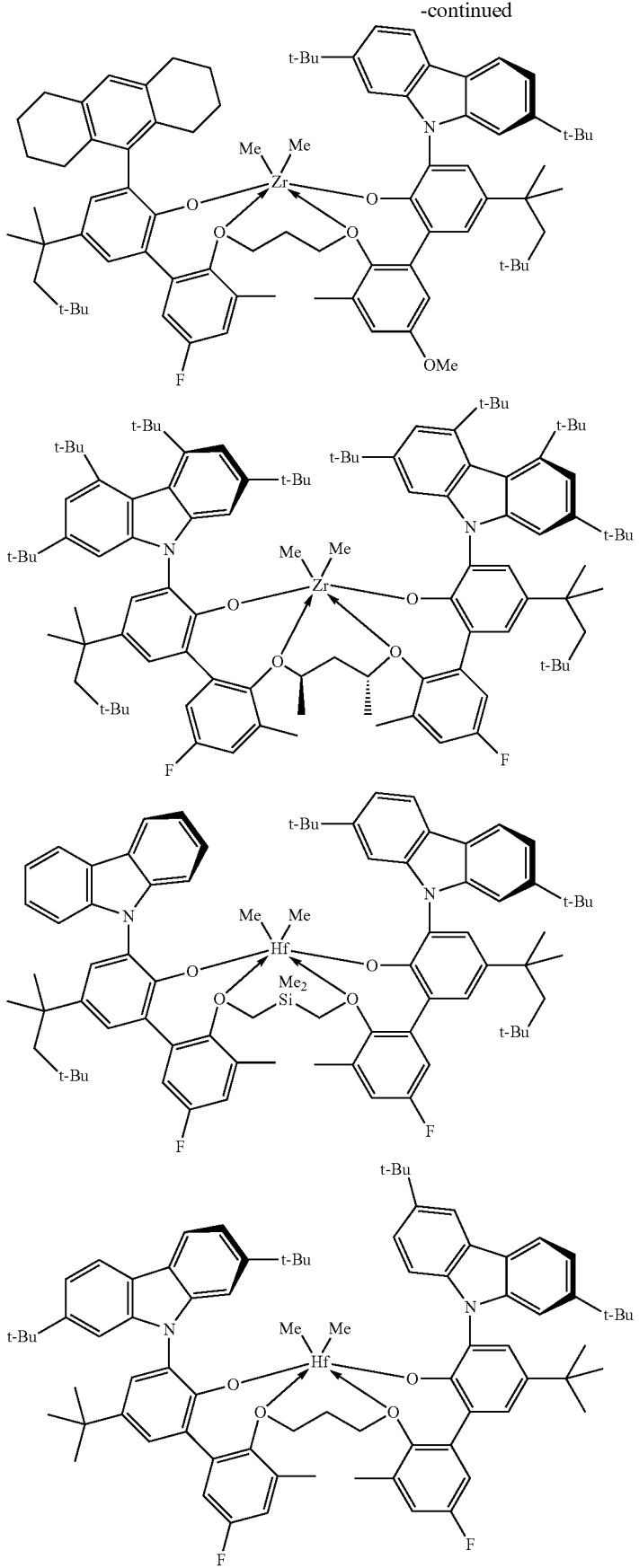

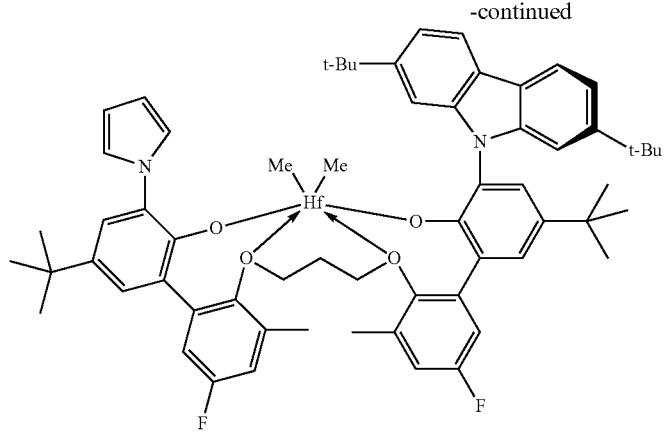
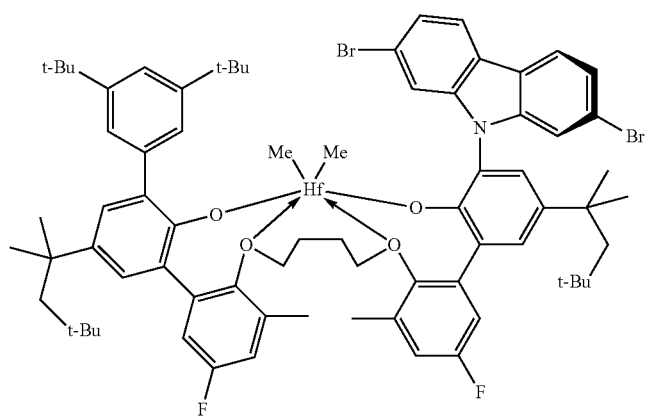
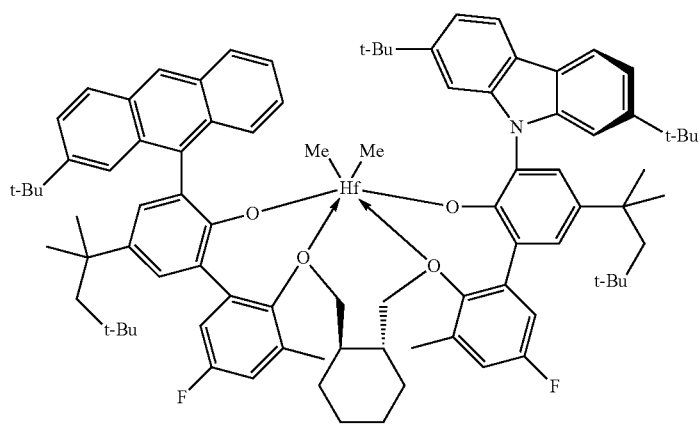
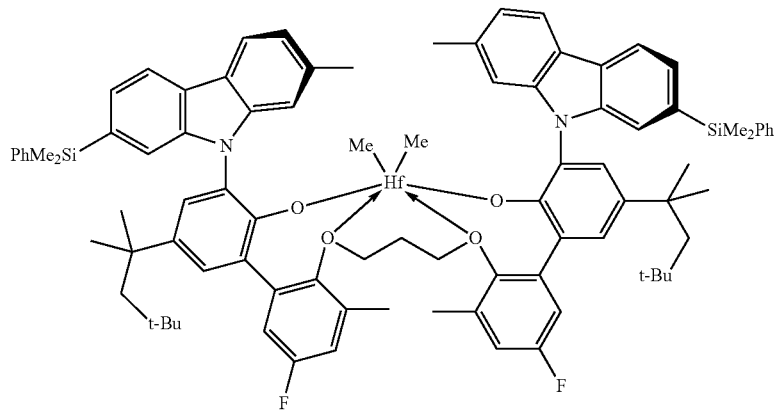

-continued
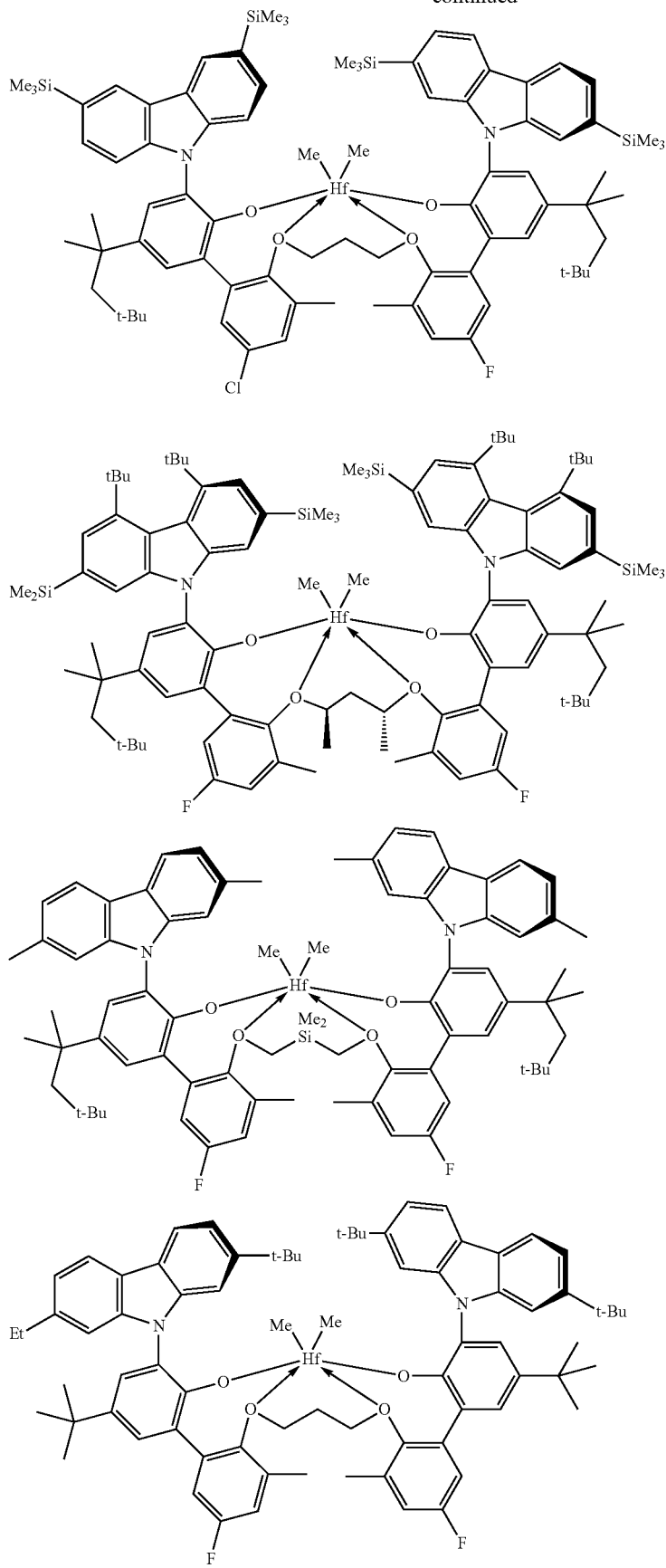

-continued
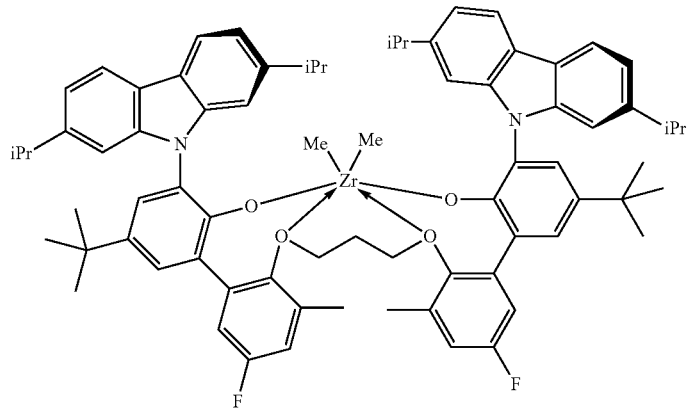
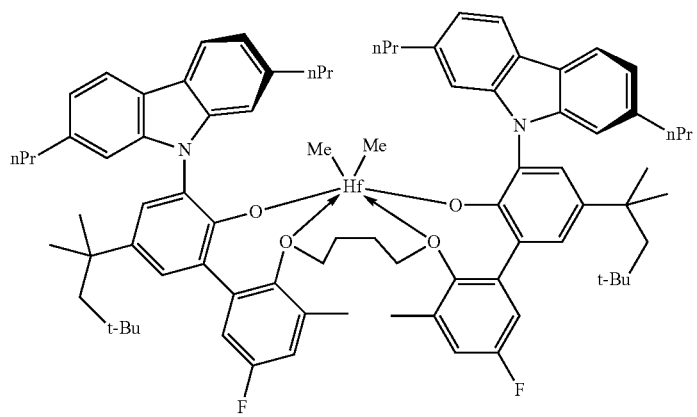
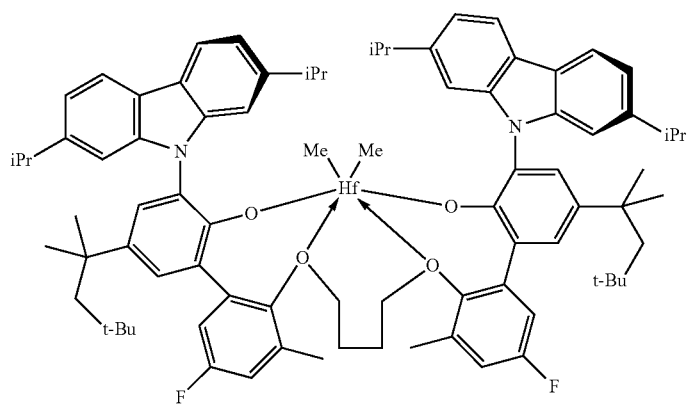
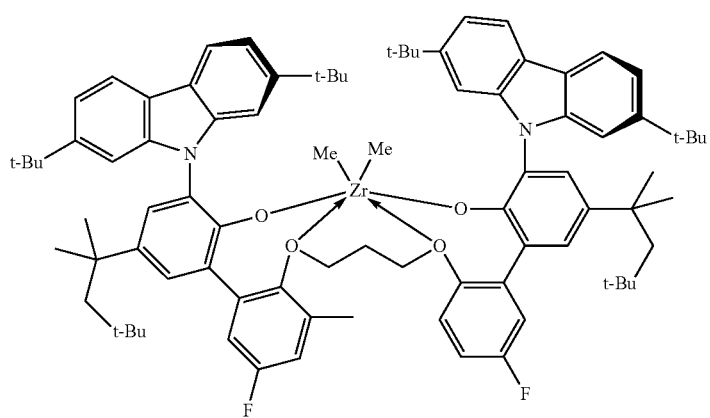

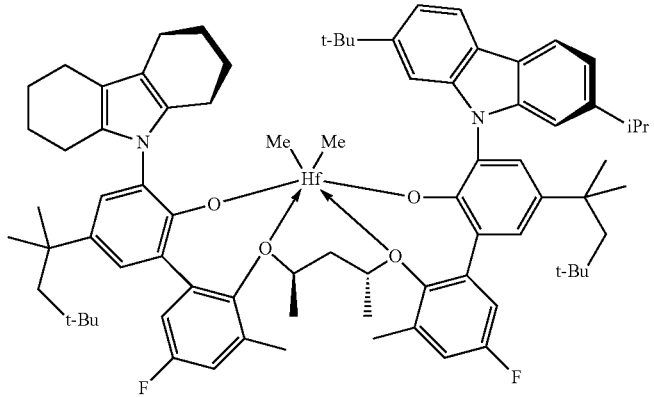
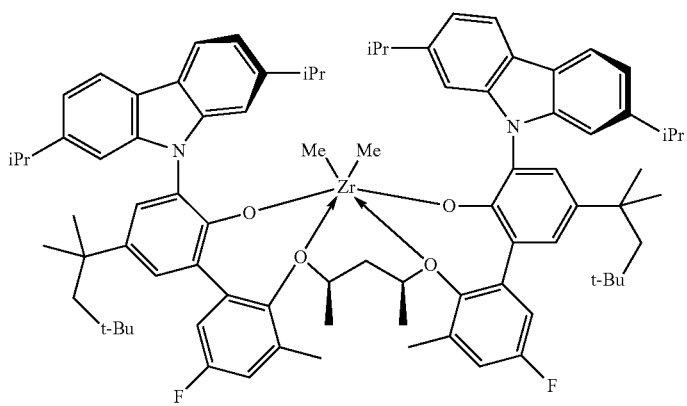
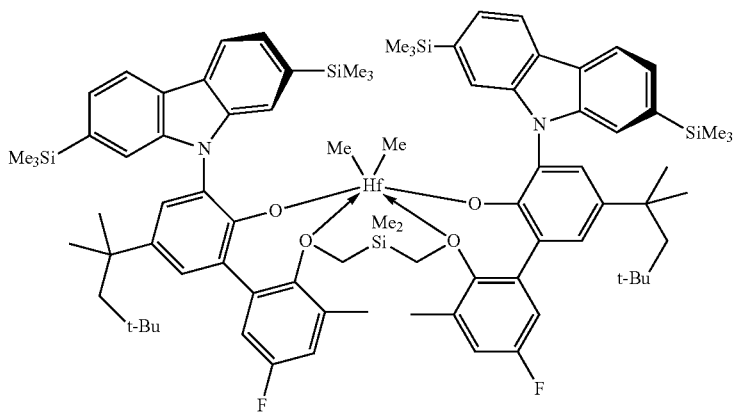
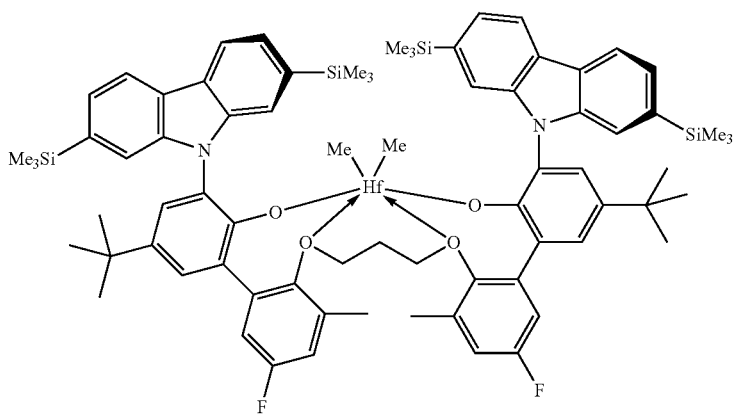

-continued
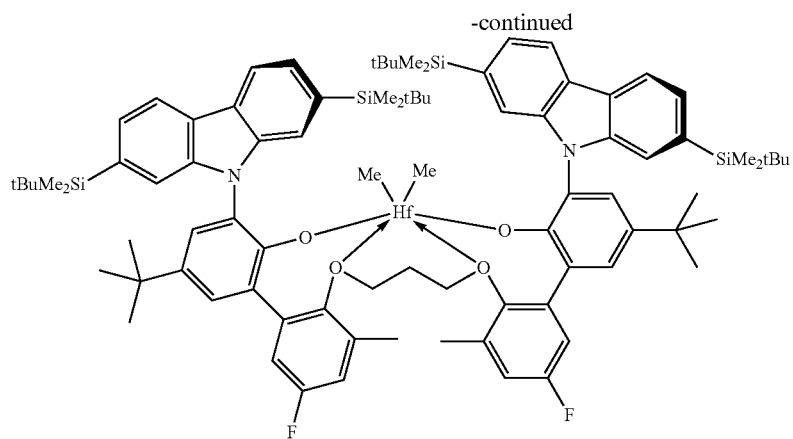
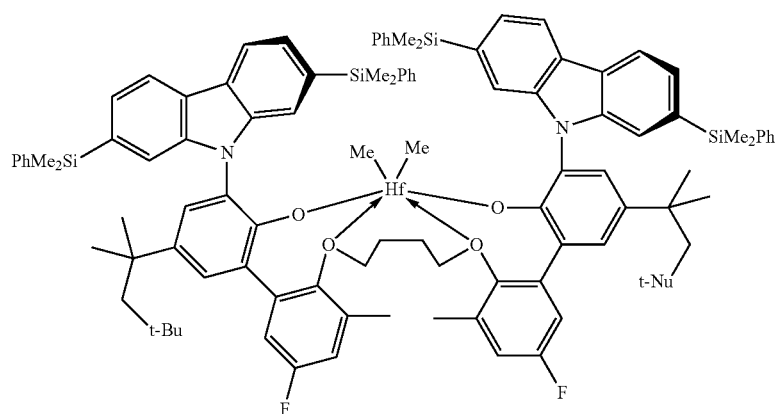
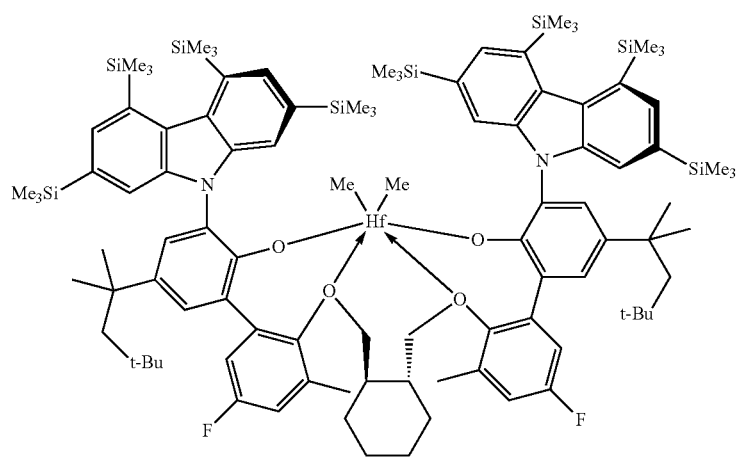

-continued
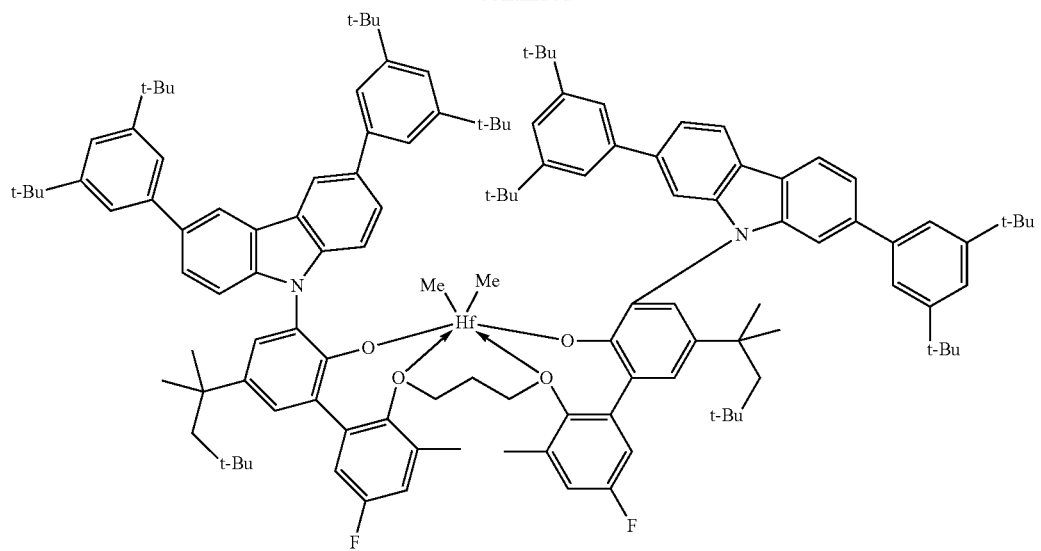
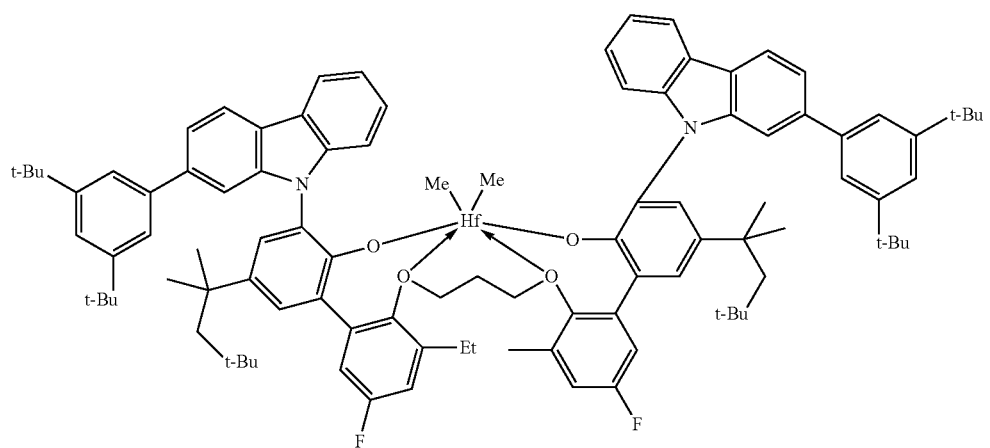
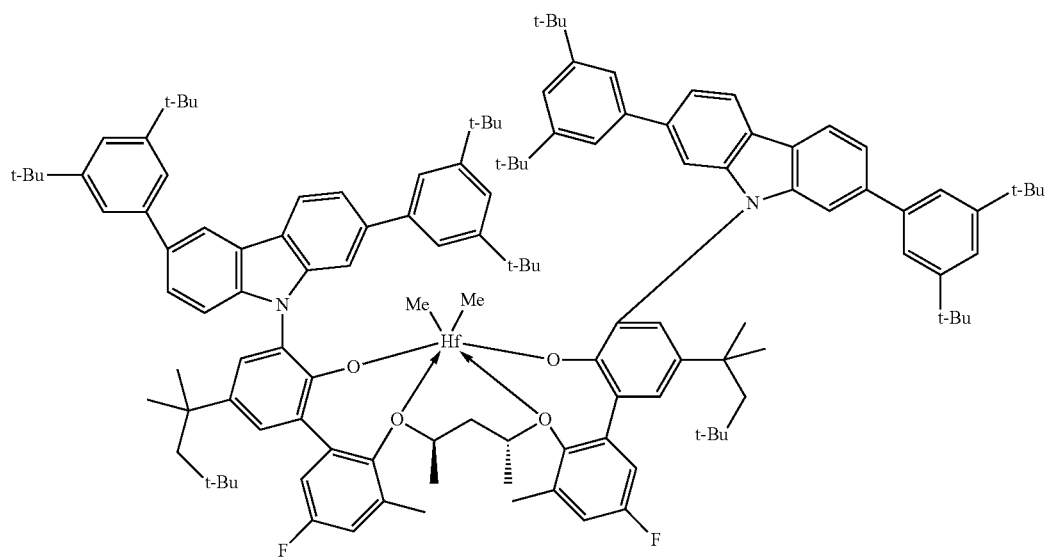

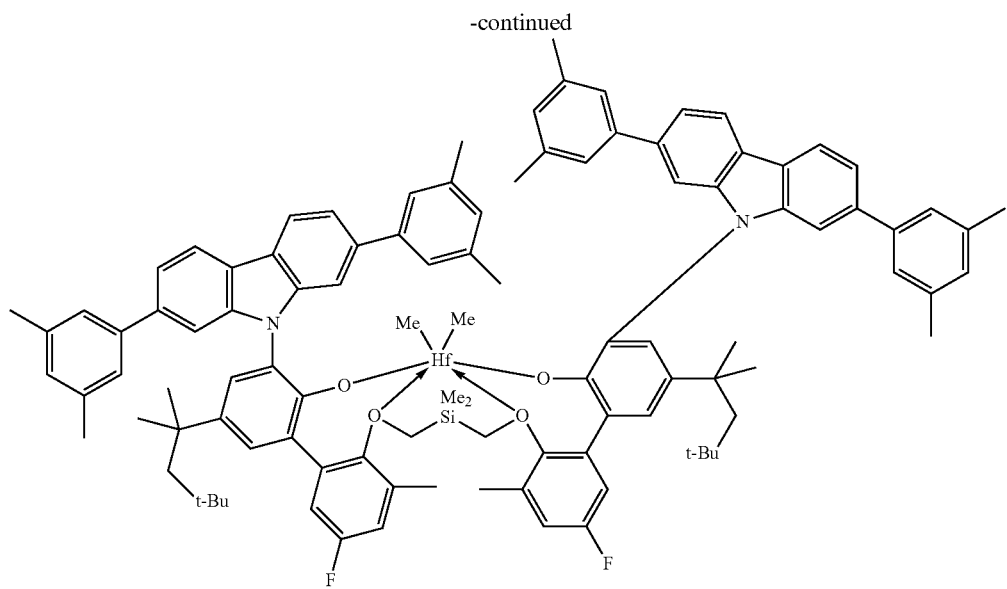
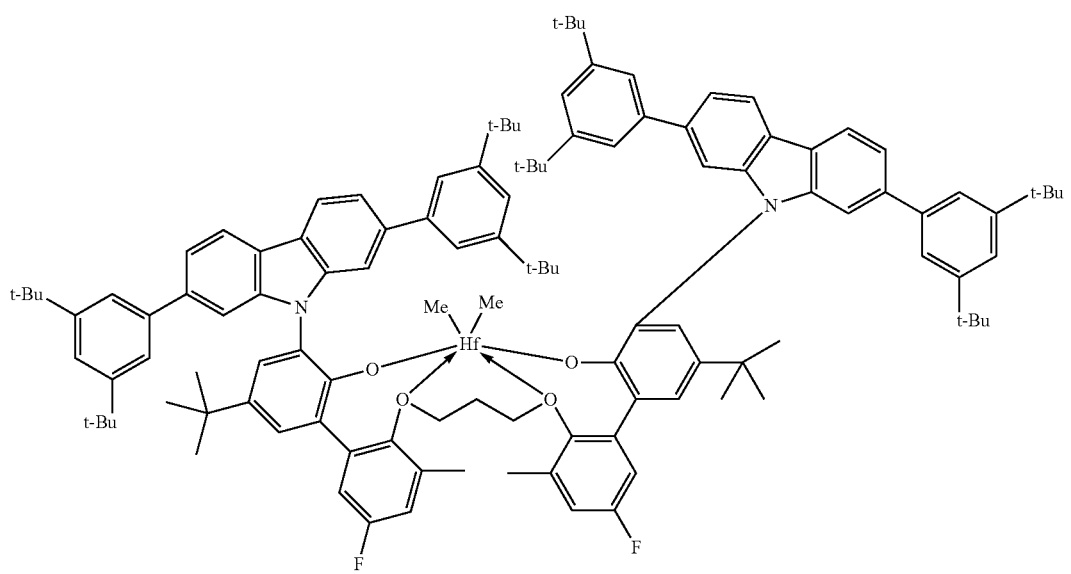
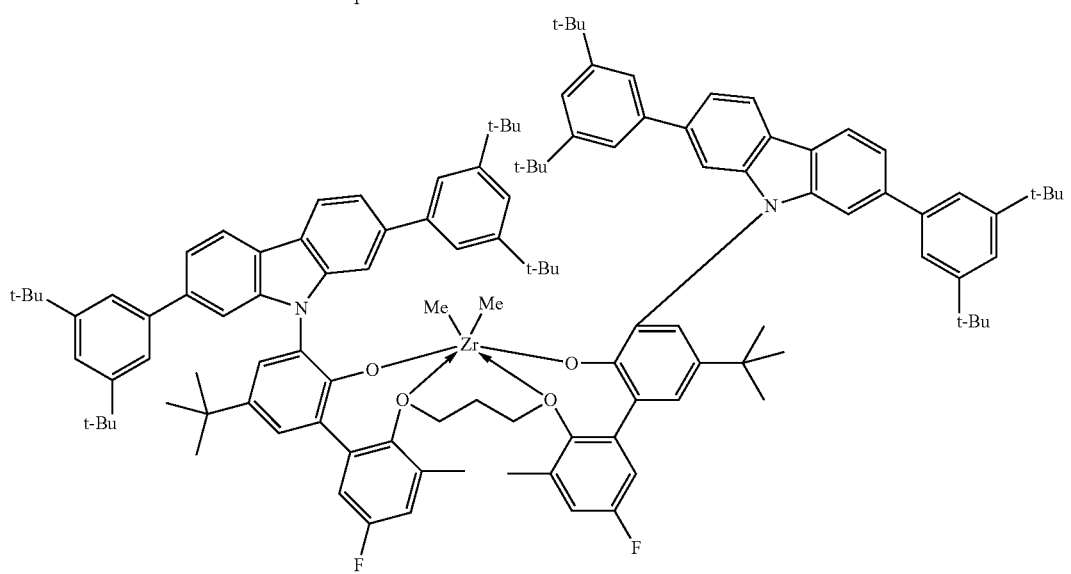

-continued
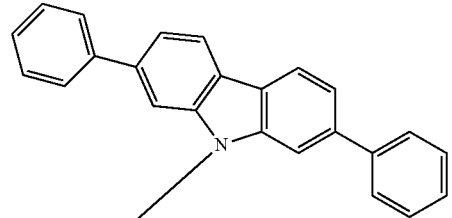
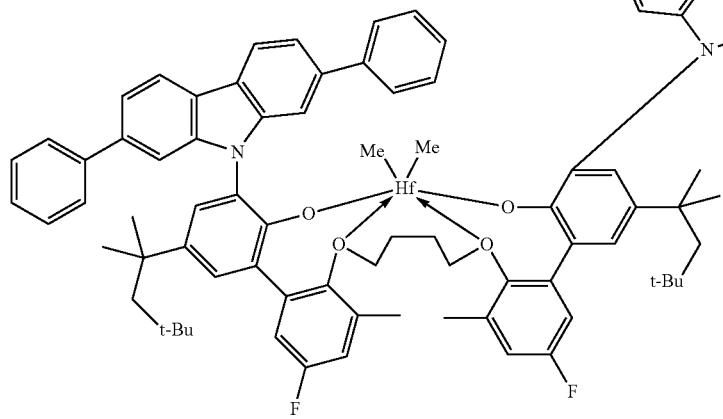
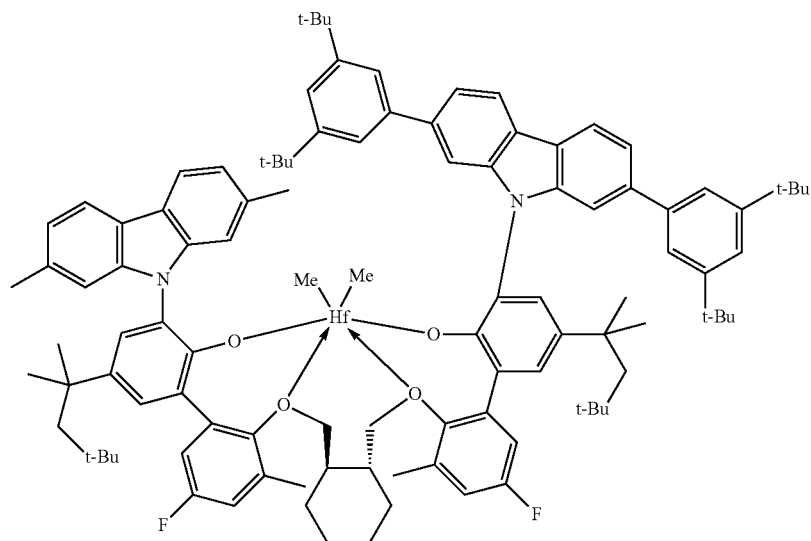
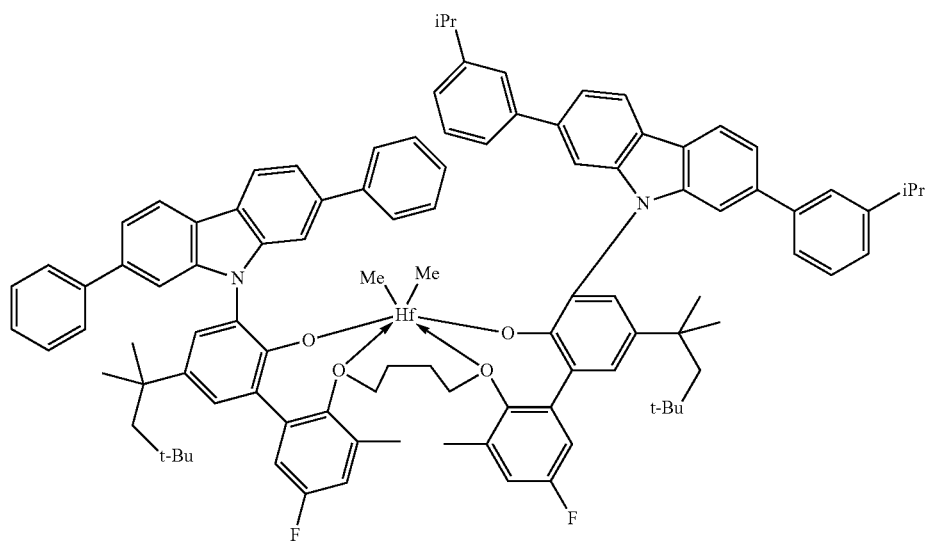

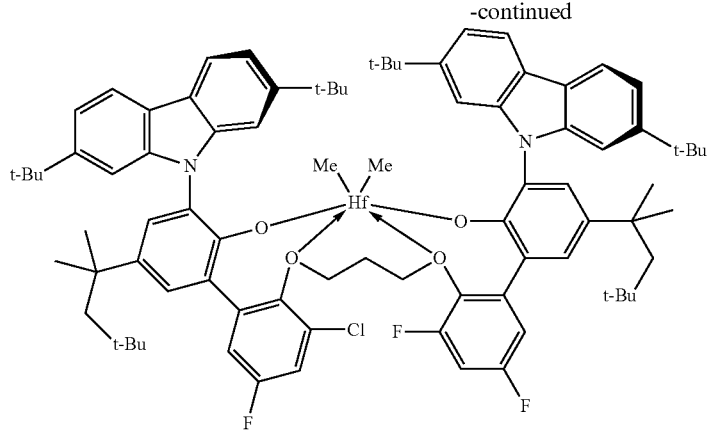
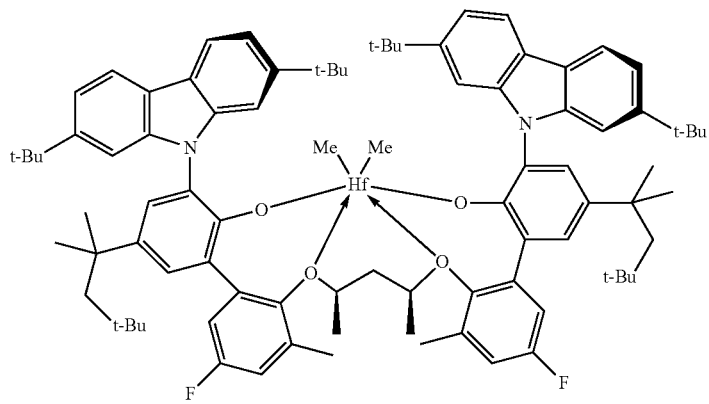
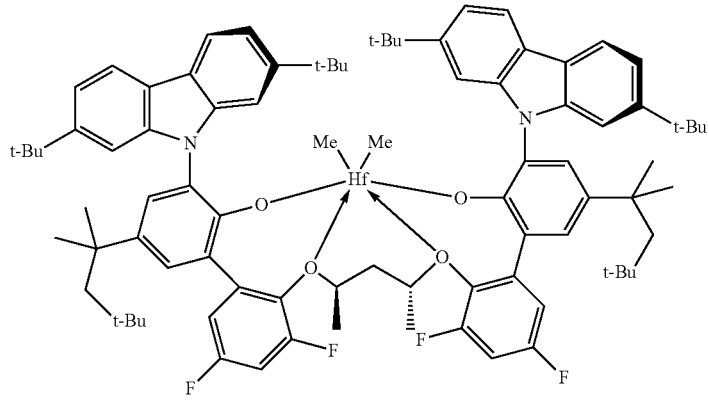
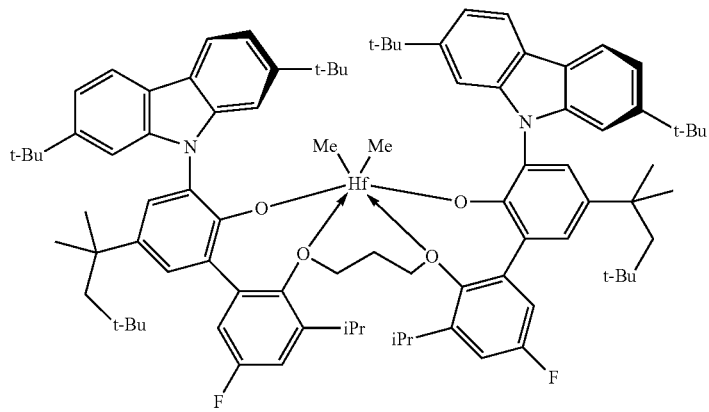

-continued
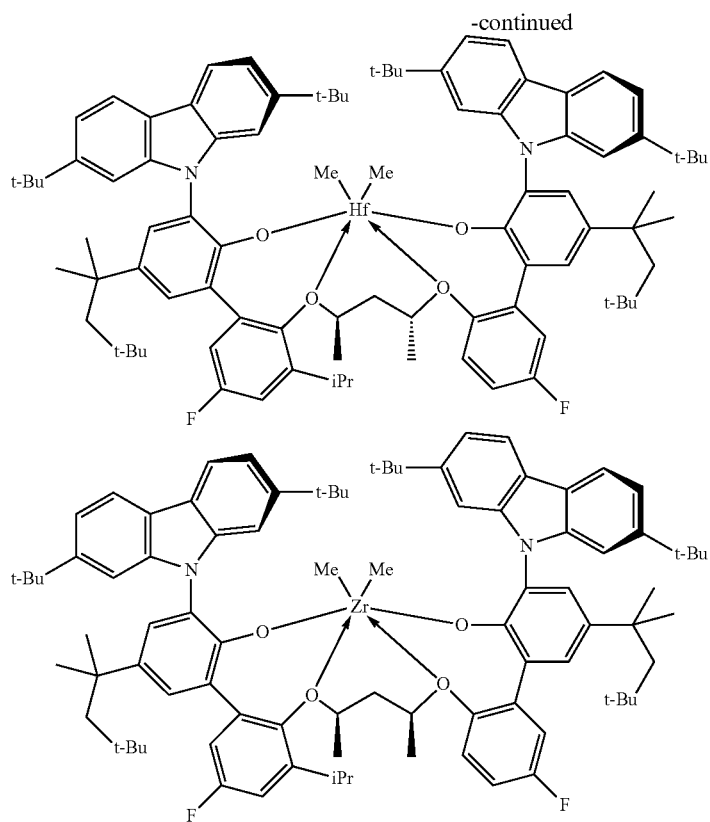
In one embodiment, the metal-ligand complex of formula (I) is a metal-ligand complex of any one of the metal-ligand complexes as described above with the provision that such metal-ligand complex of formula (I) excludes one or more metal-ligand complexes containing any one the following ligand structures:
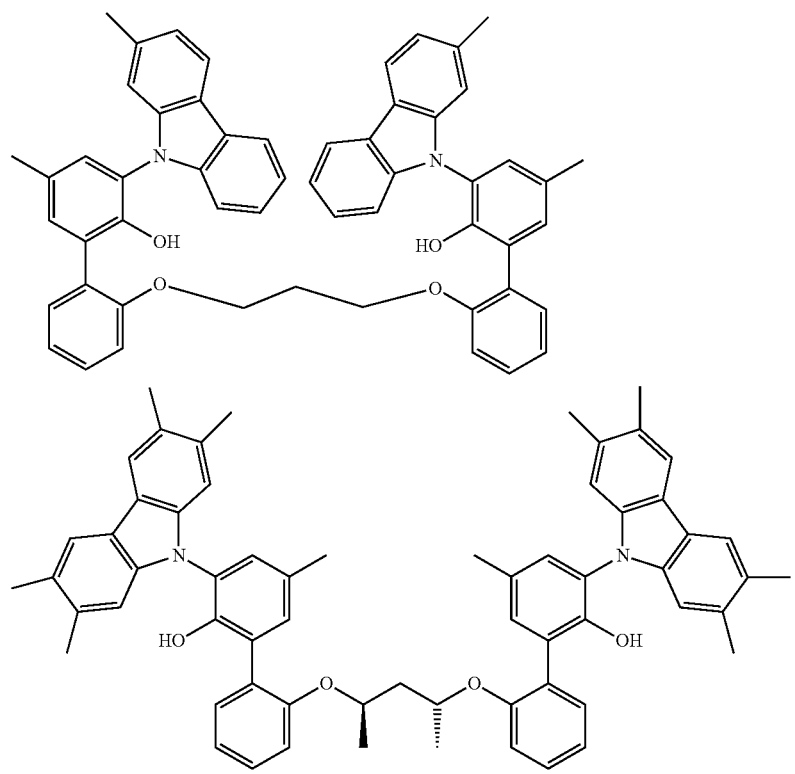

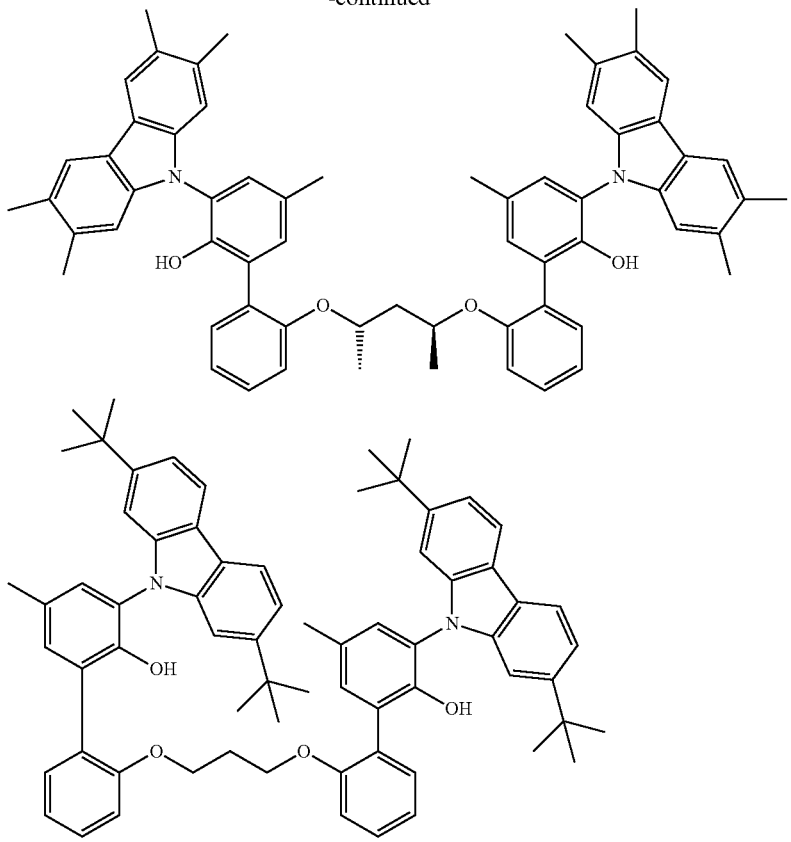

Co-catalyst Component

The procatalyst comprising the metal-ligand complex of formula (I) is rendered catalytically active by contacting it to, or combining it with, the activating co-catalyst or by using an activating technique such as those that are known in the art for use with metal-based olefin polymerization reactions. Suitable activating co-catalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 metal compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri(($C_1$-$C_{10}$) alkyl)aluminum or tri(($C_6$-$C_{18}$)aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris(($C_1$-$C_{20}$) hydrocarbyl) borate (e.g., trityl tetrafluoroborate) or a tri (($C_1$-$C_{20}$)hydrocarbyl)ammonium tetra(($C_1$-$C_{20}$)hydrocarbyl)borane (e.g., bis(octadecyl)methylammonium tetrakis (pentafluorophenyl)borane). As used herein, the term "ammonium" means a nitrogen cation that is a (($C_1$-$C_{20}$) hydrocarbyl)$_4$N$^+$, a (($C_1$-$C_{20}$)hydrocarbyl)$_3$N(H)$^+$, a (($C_1$-$C_{20}$)hydrocarbyl)$_2$N(H)$_2^+$, ($C_1$-$C_{20}$)hydrocarbylN(H)$_3^+$, or N(H)$_4^+$, wherein each ($C_1$-$C_{20}$)hydrocarbyl may be the same or different.

Exemplary combinations of neutral Lewis acid activating co-catalysts include mixtures comprising a combination of a tri(($C_1$-$C_4$)alkyl)aluminum and a halogenated tri(($C_6$-$C_{18}$) aryl)boron compound, especially a tris(pentafluorophenyl) borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex): (tris(pentafluoro-phenylborane): (alumoxane) [e.g., (Group 4 metal-ligand complex):(tris(pentafluoro-phenylborane): (alumoxane)] are from 1:1:1 to 1:10:30, other exemplary embodiments are from 1:1:1.5 to 1:5:10.

Many activating co-catalysts and activating techniques have been previously taught with respect to different metal-ligand complexes in the following U.S. Pat. Nos.: 5,064,802; 5,153,157; 5,296,433; 5,321,106 5,350,723; 5,425,872; 5,625,087; 5,721,185 5,783,512; 5,883,204; 5,919,983;

6,696,379; and 7,163,907. Examples of suitable hydrocarbyloxides are disclosed in U.S. Pat. No. 5,296,433. Examples of suitable Bronsted acid salts for addition polymerization catalysts are disclosed in U.S. Pat. Nos. 5,064,802; 5,919,983; 5,783,512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, the procatalyst comprising the metal-ligand complex of formula (I) may be activated to form an active catalyst composition by combination with one or more cocatalyst such as a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to modified methyl aluminoxane (MMAO), bis(hydrogenated tallow alkyl)methyl, tetrakis(pentafluorophenyl)borate(1-) amine (RIB S-2), triethyl aluminum (TEA), and any combinations thereof.

In some embodiments, one or more of the foregoing activating co-catalysts are used in combination with each other. An especially preferred combination is a mixture of a tri(($C_1$-$C_4$)hydrocarbyl)aluminum, tri(($C_1$-$C_4$)hydrocarbyl)borane, or an ammonium borate with an oligomeric or polymeric alumoxane compound.

The ratio of total number of moles of one or more metal-ligand complexes of formula (I) to total number of moles of one or more of the activating co-catalysts is from 1:10,000 to 100:1. In some embodiments, the ratio is at least 1:5000, in some other embodiments, at least 1:1000; and 10:1 or less, and in some other embodiments, 1:1 or less. When an alumoxane alone is used as the activating co-catalyst, preferably the number of moles of the alumoxane that are employed is at least 100 times the number of moles of the metal-ligand complex of formula (I). When tris(pentafluorophenyl)borane alone is used as the activating co-catalyst, in some other embodiments, the number of moles of the tris(pentafluorophenyl)borane that are employed to the total number of moles of one or more metal-ligand complexes of formula (I) form 0.5:1 to 10:1, in some other embodiments, from 1:1 to 6:1, in some other embodiments, from 1:1 to 5:1. The remaining activating co-catalysts are generally employed in approximately mole quantities equal to the total mole quantities of one or more metal-ligand complexes of formula (I).

Catalyst System Properties

The inventive catalyst composition comprising the procatalyst comprising the metal-ligand complex of formula (I) and one or more cocatalyst, as described herein, has a reactivity ratio $r_1$, as further defined hereinbelow, in the range of greater than 100; for example, greater than 150, or greater than 200.

It is believed that steric interactions for the inventive catalysts result in polymerization of ethylene more selectively than sterically larger alpha-olefin (or other larger olefin comonomer) during the invention process (i.e., the invention catalyst preferentially polymerizes ethylene in the presence of the alpha-olefin). Again without being bound by theory, it is believed that such steric interactions cause the invention catalyst prepared with or from the metal-ligand complex of formula (I) to adopt a conformation that allows ethylene to access the M substantially more easily, or adopt a reactive conformation more readily, or both than the invention catalyst allows the alpha-olefin to do so. The resulting difference in polymerization rates (i.e., selectivity) between ethylene and the alpha-olefin with the invention catalyst in the invention process can be characterized by the reactivity ratio $r_1$.

For random copolymers in which the identity of the last monomer inserted dictates the rate at which subsequent monomers insert, the terminal copolymerization model is employed. In this model insertion reactions of the type

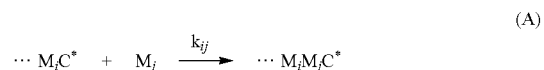
(A)

where $C^*$ represents the catalyst, $M_i$ represents monomer i , and $k_{ij}$ is the rate constant having the rate equation $$R_{p_{ij}} = k_{ij}[\ldots M_iC^*][M_j] \quad (B)$$

The comonomer mole fraction (i=2) in the reaction media is defined by the equation:

$$f_2 = \frac{[M_2]}{[M_1]+[M_2]} \quad (C)$$

A simplified equation for comonomer composition can be derived as disclosed in George Odian, *Principles of Polymerization*, Second Edition, John Wiley and Sons, 1970, as follows:

$$F_2 = \frac{r_1(1-f_2)^2 + (1-f_2)f_2}{r_1(1-f_2)^2 + 2(1-f_2)f_2 + r_2f_2^2} \quad (D)$$

From this equation the mole fraction of comonomer in the polymer is solely dependent on the mole fraction of comonomer in the reaction media and two temperature dependent reactivity ratios defined in terms of the insertion rate constants as:

$$r_1 = \frac{k_{11}}{k_{12}} \quad r_2 = \frac{k_{22}}{k_{21}} \quad (E)$$

Alternatively, in the penultimate copolymerization model, the identities of the last two monomers inserted in the growing polymer chain dictate the rate of subsequent monomer insertion. The polymerization reactions are of the form

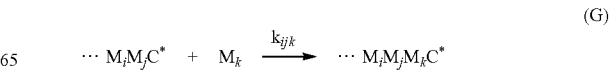
(G)

and the individual rate equations are:

$$R_{P_{ijk}} = k_{ijk}[\ldots M_i M_j = C^*][M_k] \quad (H)$$

The comonomer content can be calculated (again as disclosed in George Odian, Supra.) as:

$$\frac{(1-F_2)}{F_2} = \frac{1 + \frac{r'_1 X(r_1 X + 1)}{(r'_1 X + 1)}}{1 + \frac{r'_2(r_2 + X)}{X(r'_2 + X)}} \quad (I)$$

where X is defined as:

$$X = \frac{(1-f_2)}{f_2} \quad (J)$$

and the reactivity ratios are defined as:

$$r_1 = \frac{k_{111}}{k_{112}} \quad r'_1 = \frac{k_{211}}{k_{212}} \quad (K)$$
$$r_2 = \frac{k_{222}}{k_{221}} \quad r'_2 = \frac{k_{122}}{k_{121}}$$

For this model as well the polymer composition is a function only of temperature dependent reactivity ratios and comonomer mole fraction in the reactor. The same is also true when reverse comonomer or monomer insertion may occur or in the case of the interpolymerization of more than two monomers.

Reactivity ratios for use in the foregoing models may be predicted using well known theoretical techniques or empirically derived from actual polymerization data. Suitable theoretical techniques are disclosed, for example, in B. G. Kyle, *Chemical and Process Thermodynamics,* Third Addition, Prentice-Hall, 1999 and in Redlich-Kwong-Soave (RKS) Equation of State, *Chemical Engineering Science,* 1972, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201 USA.

Accordingly, the process for producing ethylene based polymers according to the present invention selectively gives the rich polyethylene (e.g., a high density polyethylene) or rich polyethylene segment of the poly(ethylene alpha-olefin) copolymer in the presence of alpha-olefin, which is substantially unpolymerized thereby. The process for producing ethylene based polymers employs olefin polymerizing conditions. In some embodiments, the olefin polymerizing conditions independently produce a catalyst in situ that is formed by reaction of the procatalyst comprising metal-ligand complex of formula (I), and one or more cocatalysts in the presence of one or more other ingredients. Such other ingredients include, but are not limited to, (i) olefin monomers; (ii) another metal-ligand complex of formula (I); (iii) one or more of catalyst systems; (iv) one or more chain shuttling agents; (v) one or more catalyst stabilizers; (vi) one or more solvents; and (vii) a mixture of any two or more thereof.

A particularly preferred inventive catalyst is one that can achieve a high selectivity for polymerizing ethylene in the presence of the ($C_3$-$C_{40}$) alpha-olefin in the process for producing an ethylene based polymer, wherein the high selectivity is characterized by the reactivity ratio $r_1$ described previously. Preferably for the inventive process, the reactivity ratio $r_1$ is greater than 50, more preferably greater than 100, still more preferably greater than 150, still more preferably greater than 200. When the reactivity ratio $r_1$ for the invention process approaches infinity, incorporation of the alpha-olefin into (or onto) the rich polyethylene produced thereby approaches 0 mole percent (mol %).

The inventive catalyst composition comprising the procatalyst and one or more cocatalyst, as described herein, has catalytic efficiency in the rage of from greater than 1000,000 g of polymer per gram of active metal center; for example, from greater than 2000,000 g of polymer per gram of active metal center. The ecatalytic efficiency is measured in terms of amount of polymer produced relative to the amount catalyst used in solution polymerisation process, wherein theploymersation temperature is at least 130° C., for example in the range of from 170 to 195° C., and ethylene concentration is greater than 5 g/L, for example, greater than 6 g/L, and wherein the ethylene conversion is greater than 70 percent, for example, greater than 80 percent, or in the alternative, greater than 90 percent.

Process for Producing Procatalyst

In some embodiments, the ligands of the invention may be prepared using known procedures. Specifically, the ligands of the invention maybe prepared using a variety of synthetic routes, depending on the variation desired in the ligand. In general, building blocks are prepared that are then linked together with a bridging group. Variations in the R group substituents can be introduced in the synthesis of the building blocks.

Variations in the bridge can be introduced with the synthesis of the bridging group. Specific ligands within the scope of this invention may be prepared according to the general schemes shown below, where building blocks are first prepared and then coupled together. There are several different ways to use these building blocks. In one embodiment, generally, each of the optionally substituted phenyl rings is prepared as a separate building block. The desired optionally substituted phenyls are then combined into bi-phenyl building blocks, which are then bridged together. In another embodiment, the optionally substituted phenyl building blocks are bridged together and then additional optionally substituted phenyl building blocks are added to form the bridged bi-aryl structures. The starting materials or reagents used are generally commercially available, or are prepared via routine synthetic means.

In the schemes below, the term ligand refers to the organic precursor to the pro-catalyst. The pro-catalyst is derived from a reaction of the ligand with a suitable metallic (titanium, zirconium, or hafnium) precursor.

Common organic substituents have been abbreviated as in the following key system:
Me=methyl
Et=ethyl
Ph=phenyl
t-Bu=tertiary butyl
i-Pr=isopropyl
n-Bu=butyl
$Me_2Si$=dimethylsilyl
$Me_3Si$=trimethylsilyl
$Me_2PhSi$=dimethylphenylsilyl
DME=dimethoxyethane
THF=tetrahydrofuran

1. Preparation of Substituted nitro-1,1'-biphenyl

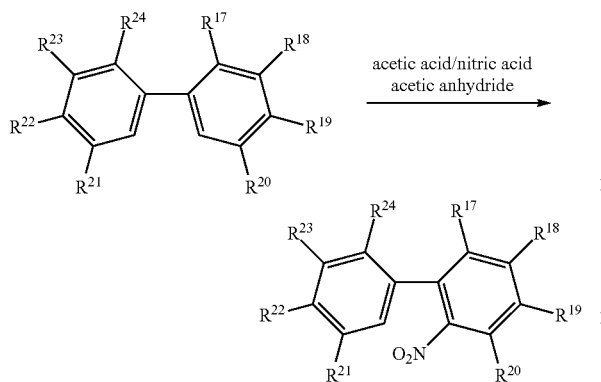

To the desired substituted 1,1'-biphenyl, (approximately 56 mmol) is added acetic anhydride (approximately 300 mL) in a flask that is immersed in a room temperature water bath. To the suspension is added slowly dropwise a mixture of acetic acid (approximately 15 mL, 262 mmol) and fuming nitric acid (approximately 9.0 mL, 191 mmol) over the period of approximately 10 minutes via a pressure equalizer addition funnel. The mixture is then allowed to stir until the reaction was complete, as indicated by gas chromatography/mass spectroscopy (GC/MS) monitoring. The mixture is then added to approximately 2.5L of ice-water and stirred for approximately 1-2 hours. The precipitate is collected by vacuum filtration and washed with two approximately 100-mL portions of ice-water. This crude material is dissolved in approximately 250 mL of methylene chloride, and washed with water (approximately 250 mL), and then 1M aqueous NaOH (approximately 250 mL). The organic phase is dried over anhydrous magnesium sulfate, filtered and concentrated under high vacuum. The crude material is then purified by flash chromatography.

2. Preparation of Substituted-9H-carbazole

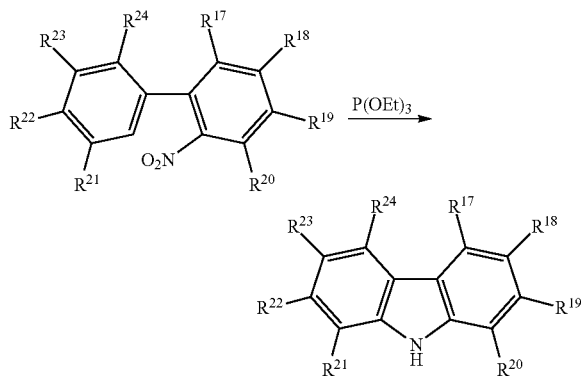

To the desired substituted 2-nitro-1,1'-biphenyl (approximately 25 mmol) in a glove box is added triethylphosphite (approximately 31.0 mL, 180 mmol). The mixture is removed from the glove box and taken to the hood, and placed under a nitrogen atmosphere and heated under gentle reflux (approximately 175° C. mantle temperature) while monitoring the reaction progress by GC/MS. Once the reaction is determined to be complete it is cooled and the condenser is removed from the reaction and the triethylphosphite was distilled off under vacuum with a short path column at approximately 75° C. (mantle temperature) until a few mL of liquid remain. The flask is then heated further to approximately 125° C. until no additional distillation occurs. The residue is then allowed to cool to room temperature, then diluted and washed with approximately 100 mL of 1:1 methanol:ice-water and filtered. The precipitate is isolated by vacuum filtration and the residue remaining in the reaction flask is dissolved in approximately 300 mL of methylene chloride, dried with anhydrous magnesium sulfate, filtered and concentrated to give the crude material. This crude is then purified by flash chromatography.

3. Preparation of Substituted-9-(2-((tetrahydro-2H-pyran-2-yl)oxy)-5-(2,4,4-trimethylpentan-2-yl)phenyl)-9H-carbazole:

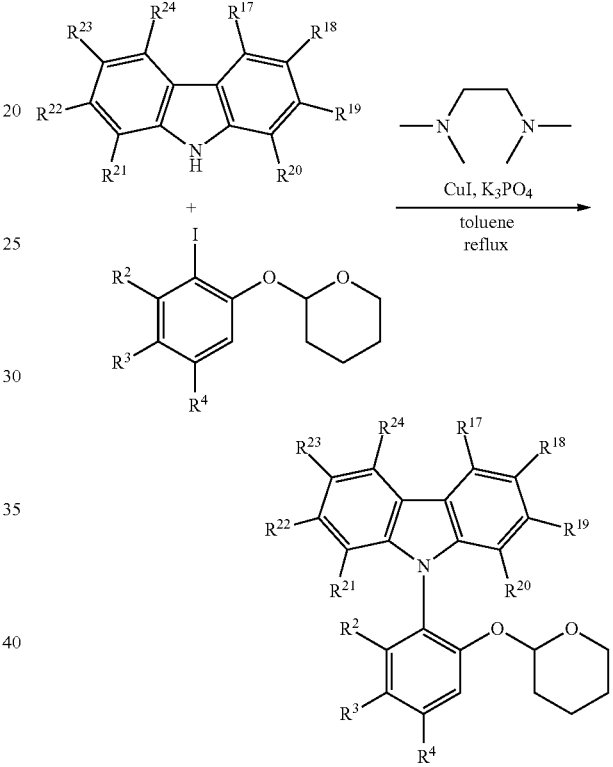

To a 250-mL three-necked round-bottomed flask in a glove box is added the desired substituted 2-(2-iodophenoxy)tetrahydro-2H-pyran (approximately 52 mmol), the desired substituedcarbazole (approximately 29 mmol), $K_3PO_4$ (approximately 23.40 g, 110.24 mmol), anhydrous CuI (approximately 0.22 g, 1.16 mmol), dried toluene (approximately 85 mL) and N,N'-dimethylethylenediamine (approximately 0.45 mL, 4.18 mmol). The flask is taken out of the glove box to the hood and heated under reflux. The reaction progress is monitored by GC/MS analysis, and in some cases additional anhydrous CuI (approximately 0.2 g, 1.05 mmol) slurried in dry toluene (approximately 0.9 mL) and N,N'-dimethylethylenediamine (approximately 0.45 mL, 4.18 mmol) is added to the mixture, and heating under reflux continued until such a time when the conversion is observed to be complete. The reaction is then allowed to cool to room temperature and filtered through a small silica plug, washed with tetrahydrofuran and concentrated to give the crude product. This crude material can be purified by either recrystallization or flash chromatography.

4. Preparation of Substituted-2-((tetrahydro-2H-pyran-2-yl)oxy)-3-(4,4,5,5-tetramethyl-1,3,2-dioxaborolan-2-yl:

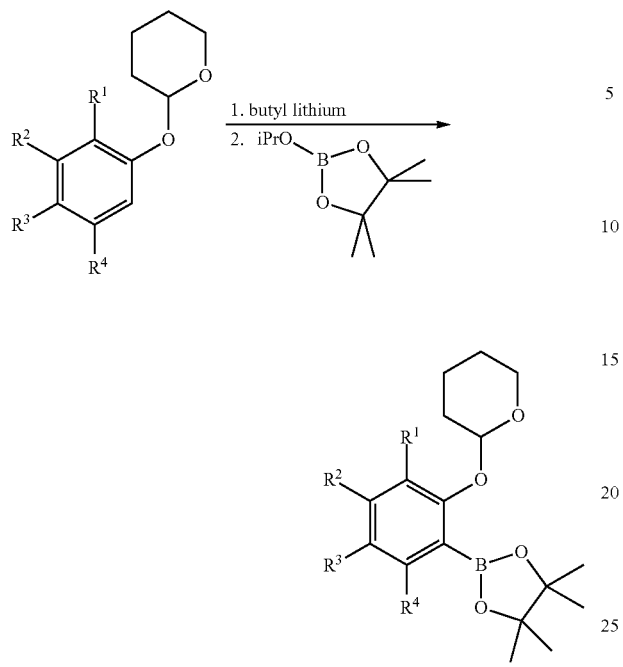

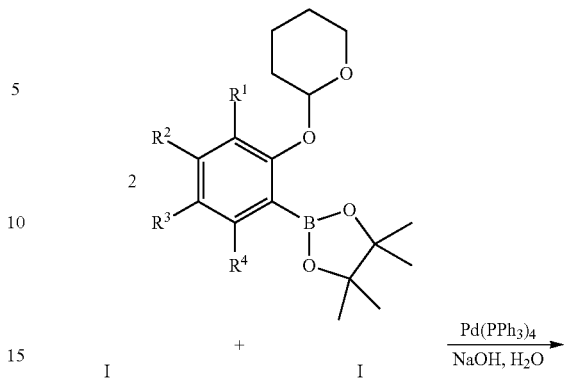

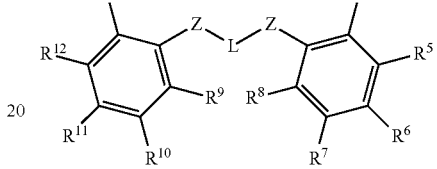

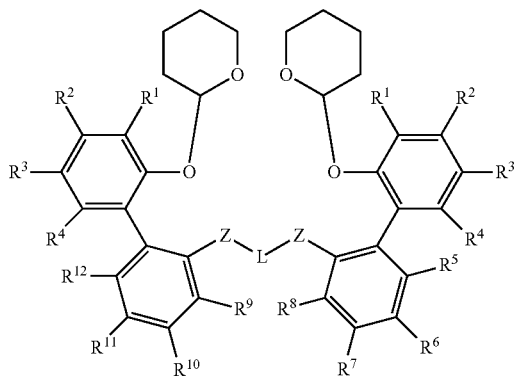

To an oven dried three-necked round-bottomed flask at approximately 0-10° C. under N₂ atmosphere is added the desired 2-((tetrahydro-2H-pyran-2-yl)oxy)-5-(2,4,4-trimethylpentan-2-yl)phenyl) (approximately 14 mmol) and dry tetrahydrofuran (approximately 90 mL). This solution was cooled to approximately 0-10° C. (ice-water bath) for approximately 15 minutes and 2.5 M n-butyllithium in hexanes (approximately 14 mL, 35.00 mmol) is added slowly. After stirring for approximately 4 hours, 2-isopropoxy-4,4,5,5-tetramethyl-1,3,2-dioxaborolane (approximately 7.0 mL, 34 mmol) is added slowly. The mixture is stirred for one hour at approximately 0-10° C. before allowing the reaction to warm to room temperature and then stirred for an additional approximately 18 hours. To the reaction mixture is added cold saturated aqueous sodium bicarbonate (approximately 75 mL). The mixture is extracted with approximately four 50-mL portions of methylene chloride. The organic phases are combined and washed with cold saturated aqueous sodium bicarbonate (approximately 200 mL), brine (approximately 200 mL), then dried over anhydrous magnesium sulfate, filtered and concentrated to give the crude product, which is slurried in acetonitrile (approximately 75 mL) and allowed to sit for an hour at room temperature before isolating the solid by vacuum filtration. The solids are washed with a small portion of cold acetonitrile and dried under high vacuum to afford the product.

5a. Preparation of Protected Ligand (Method 1, Simultaneous Double Suzuki Reaction).

To a round bottom flask under N₂ atmosphere is added the desired substituted-2-((tetrahydro-2H-pyran-2-yl)oxy)-3-(4,4,5,5-tetramethyl-1,3,2-dioxaborolan-2-yl(approximately 9.9 mmol), dimethoxyethane (approximately 120 mL), a solution of NaOH (approximately 1.30 g, 32.5 mmol) in water (approximately 35 mL), tetrahydrofuran (approximately 60 mL), and the desired linked bis-2-iodoaryl species (approximately 4.7 mmol). The system is then purged with N₂ for approximately 15 minutes and Pd(PPh₃)₄ (approximately 303 mg, 0.26 mmol) is added. The mixture is heated under reflux at approximately 85° C. for approximately 48 hours then allowed to cool to room temperature. Once cooled a precipitate was formed in the reaction flask which is isolated by vacuum filtration and dried under high vacuum for one hour to afford the crude protected ligand. This protected ligand can be used as such in the next step.

5b. Preparation of Protected Ligand (Method 2, Sequential Suzuki Reactions).

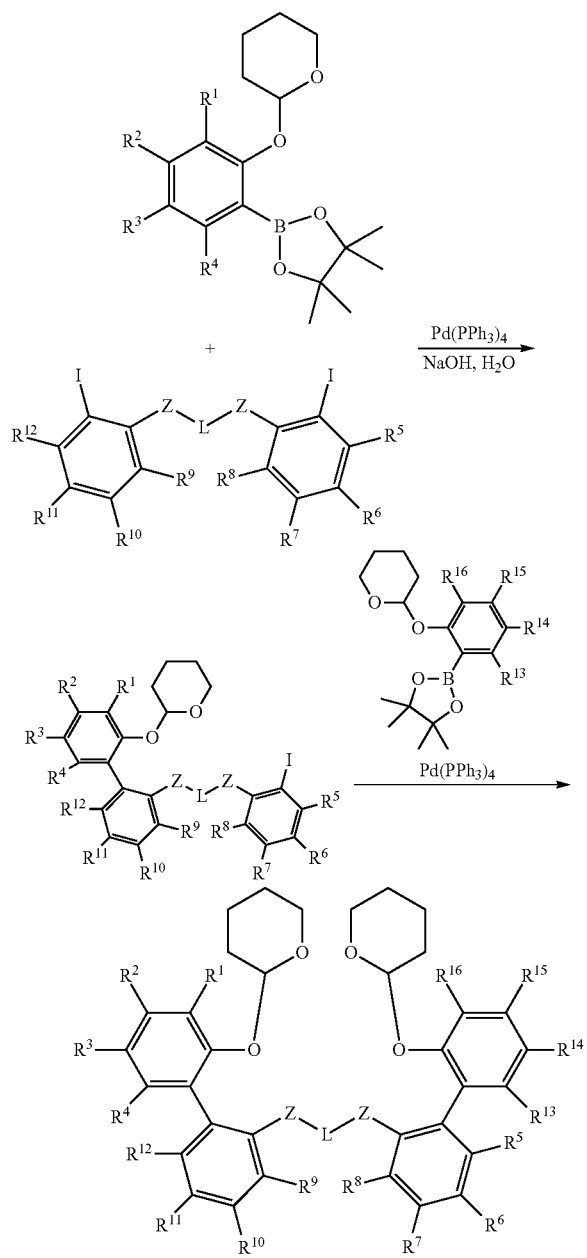

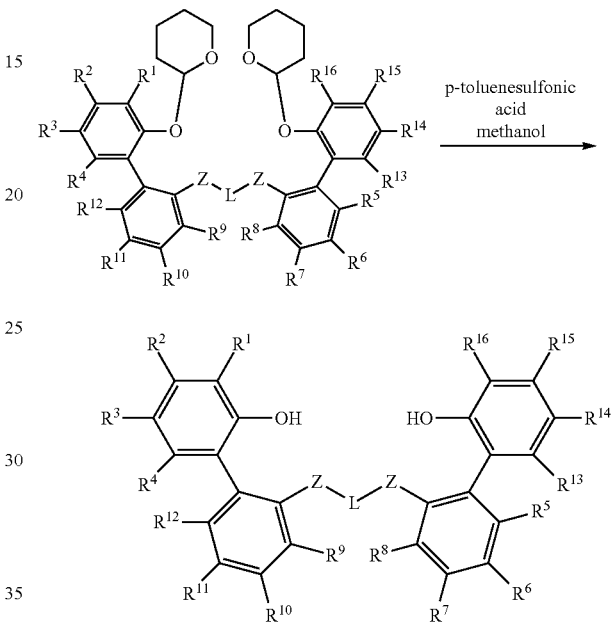

again heated under reflux at approximately 85° C. for approximately 48 hours, and then is allowed to cool to room temperature. Once cooled a precipitate is formed in the reaction flask which is isolated by vacuum filtration and dried under high vacuum for one hour to afford the crude protected ligand. This protected ligand can be used as such in the next step.

6. Preparation of Ligand

To the crude protected ligand is added a mixture of 1:1 methanol/tetrahydrofuran (approximately 200 mL) and approximately 100 mg of p-toluenesulfonic acid monohydrate. The solution is heated at approximately 60° C. for approximately 8 hours then allowed to cool and concentrated. The residue is dissolved in methylene chloride (approximately 250 mL), washed with brine (approximately 250 mL), dried over anhydrous magnesium sulfate, filtered through a pad of silica gel then concentrated. This crude material is purified by flash chromatography.

7. Example of Pro-Catalyst Preparation.

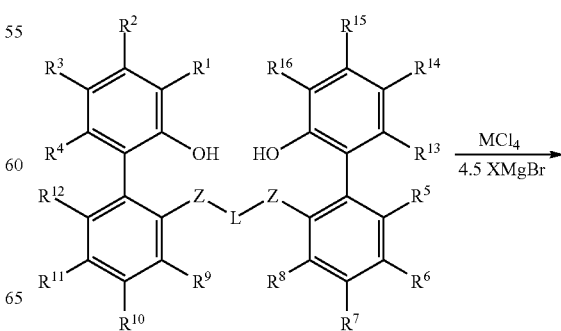

To a round bottom flask under $N_2$ atmosphere is added the desired substituted-2-((tetrahydro-2H-pyran-2-yl)oxy)-3-(4,4,5,5-tetramethyl-1,3,2-dioxaborolan-2-yl (4.7 mmol), dimethoxyethane (approximately 120 mL), a solution of NaOH (approximately 1.30 g, 32.5 mmol) in water (approximately 35 mL), tetrahydrofuran (approximately 60 mL), and the desired linked bis-2-iodoaryl species (approximately 4.7 mmol). The system is purged with $N_2$ for approximately 15 minutes and Pd(PPh$_3$)$_4$ (approximately 303 mg, 0.26 mmol) is added. The mixture is heated under reflux at approximately 85° C. for approximately 48 hours, at which point the second substituted-2-((tetrahydro-2H-pyran-2-yl)oxy)-3-(4,4,5,5-tetramethyl-1,3,2-dioxaborolan-2-yl (approximately 4.7 mmol) is added, along with additional Pd(PPh$_3$)$_4$ (approximately 303 mg, 0.26 mmol). The resulting mixture is -continued

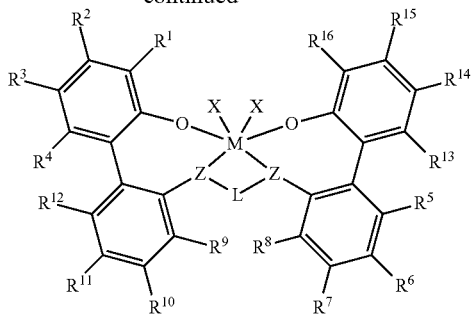

The ligand (approximately 0.38 mmol) and $MCl_4$ (approximately 0.38 mmol) are suspended in approximately 35 mL of cold (approximately −30° C.) toluene. To this mixture is added approximately 0.56 mL of 3M diethyl ether solution of XMgBr. After approximately 1-24 hr of stirring, depending on the particular ligand, the solvent is removed under reduced pressure. To the residue is added approximately 20 mL of toluene followed by approximately 25 mL of hexane. The suspension is then filtered, and the solvent was removed under reduced pressure giving the desired procatalyst.

Olefin Based Polymers

The inventive catalyst compositions comprising one or more procatalyst comprising the metal-ligand complex of formula (I) and one or more cocatalysts may be employed to prepare a variety of olefin based polymers including, but not limited to, ethylene based polymers, for example homopolymers and/or interpolymers (including copolymers) of ethylene and optionally one or more comonomers such as α-olefins, and propylene based polymers, for example homopolymers and/or interpolymers (including copolymers) of propylene and optionally one or more comonomers such as α-olefins.

Ethylene Based Polymers

The inventive ethylene based polymers, for example homopolymers and/or interpolymers (including copolymers) of ethylene and optionally one or more comonomers such as α-olefins, according to instant invention have a density in the range of 0.860 to 0.973 g/cm³. All individual values and subranges from 0.860 to 0.973 g/cm³ are included herein and disclosed herein; for example, the density can be from a lower limit of 0.860, 0.880, 0.885, 0.900, 0.905, 0.910, 0.915, or 0.920 g/cm³ to an upper limit of 0.973, 0.963, 0.960, 0.955, 0.950, 0.925, 0.920, 0.915, 0.910, or 0.905 g/cm³.

The inventive ethylene based polymers, for example homopolymers and/or interpolymers (including copolymers) of ethylene and optionally one or more comonomers such as α-olefins have a long chain branching frequency in the range of from 0.0 to 3 long chain branches (LCB) per 1000C.

The inventive ethylene based polymers, for example homopolymers and/or interpolymers (including copolymers) of ethylene and optionally one or more comonomers such as α-olefins according to the instant invention have a molecular weight distribution ($M_w/M_n$) (measured according to the conventional GPC method) in the range of from greater than or equal to 2.0. All individual values and subranges from greater than or equal to 2 are included herein and disclosed herein; for example, the ethylene/α-olefin interpolymer may have a molecular weight distribution ($M_w/M_n$) in the range of from 2 to 10; or in the alternative, the ethylene/α-olefin interpolymer may have a molecular weight distribution ($M_w/M_n$) in the range of from 2 to 5.

The inventive ethylene based polymers, for example homopolymers and/or interpolymers (including copolymers) of ethylene and optionally one or more comonomers such as α-olefins have a molecular weight ($M_w$) in the range of from equal to or greater than 20,000 g/mole, for example, in the range of from 20,000 to 350,000 g/moles.

The inventive ethylene based polymers, for example homopolymers and/or interpolymers (including copolymers) of ethylene and optionally one or more comonomers such as α-olefins have a melt index ($I_2$) in the range of 0.1 to 200 g/10 minutes. All individual values and subranges from 0.1 to 200 g/10 minutes are included herein and disclosed herein; for example, the melt index ($I_2$) can be from a lower limit of 0.1, 0.2, 0.5, 0.6, 0.8, 1, 1.5, 2.0, 2.5, 3.0, 3.5, 4.0, 4.5, 5.0, 10, 15, 20, 30, 40, 50, 60, 80, 90, 100, or 150 g/10 minutes, to an upper limit of 0.9, 1, 1.5, 2.0, 2.5, 3.0, 3.5, 4.0, 4.5, 5.0, 10, 15, 20, 30, 40, 50, 60, 80, 90, 100, 150, or 200 g/10 minutes.

In one embodiment, the inventive ethylene based polymers, for example homopolymers and/or interpolymers (including copolymers) of ethylene and optionally one or more comonomers such as α-olefins have a melt flow ratio ($I_{10}/I_2$) in the range of from 5 to 30. All individual values and subranges from 5 to 30 are included herein and disclosed herein; for example, the melt flow ratio ($I_{10}/I_2$) can be from a lower limit of 5, 5.5, 6, 6.5, 8, 10, 12, 15, 20, or 25 to an upper limit of 5.5, 6, 6.5, 8, 10, 12, 15, 20, 25, or 30.

The inventive ethylene based polymers, for example homopolymers and/or interpolymers (including copolymers) of ethylene and optionally one or more comonomers such as α-olefins have a zero shear viscosity ratio (ZSVR) in the range of from equal to or greater than 1.0; for example from 1.0 to 10.0; or in the alternative, from 1.0 to 8.0; or in the alternative, from 1.0 to 7.0; or in the alternative, from 1.0 to 5.0; or in the alternative, from 1.0 to 4.0; or in the alternative, from 1.0 to 3.0; or in the alternative, from 1.0 to 2.0.

In one embodiment, the inventive ethylene based polymers, for example homopolymers and/or interpolymers (including copolymers) of ethylene and optionally one or more comonomers such as α-olefins may further comprise at least 0.01 parts by weight of metal residues and/or metal oxide residues remaining from the inventive catalyst system per one million parts of the inventive ethylene based polymers, for example homopolymers and/or interpolymers (including copolymers) of ethylene and optionally one or more comonomers such as α-olefins. The metal residues and/or metal oxide residues remaining from the catalyst system in the inventive ethylene based polymers, for example homopolymers and/or interpolymers (including copolymers) of ethylene and optionally one or more comonomers such as α-olefins may be measured by x-ray fluorescence (XRF), which is calibrated to reference standards.

The inventive ethylene based polymers such interpolymers (including copolymers) of ethylene and optionally one or more comonomers such as α-olefins may comprise less than 20 percent by weight of units derived from one or more α-olefin comonomers. All individual values and subranges from less than 18 weight percent are included herein and disclosed herein; for example, the inventive ethylene based polymers such as interpolymers (including copolymers) of ethylene and optionally one or more comonomers such as α-olefins have may comprise from less than 15 percent by weight of units derived from one or more α-olefin comonomers; or in the alternative, less than 10 percent by weight of units derived from one or more α-olefin comonomers; or in the alternative, from 1 to 20 percent by weight of units derived from one or more α-olefin comonomers; or in the alternative, from 1 to 10 percent by weight of units derived from one or more α-olefin comonomers.

The inventive ethylene based polymers such as interpolymers (including copolymers) of ethylene and optionally one or more comonomers such as α-olefins have may comprise less than 10 percent by moles of units derived from one or more α-olefin comonomers. All individual values and subranges from less than 10 mole percent are included herein and disclosed herein; for example, the inventive ethylene based polymers such as interpolymers (including copolymers) of ethylene and optionally one or more comonomers such as α-olefins have may comprise from less than 7 percent by moles of units derived from one or more α-olefin comonomers; or in the alternative, from less than 4 percent by moles of units derived from one or more α-olefin comonomers; or in the alternative, from less than 3 percent by moles of units derived from one or more α-olefin comonomers; or in the alternative, from 0.5 to 10 percent by moles of units derived from one or more α-olefin comonomers; or in the alternative, from 0.5 to 3 percent by moles of units derived from one or more α-olefin comonomers.

The α-olefin comonomers typically have no more than 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-hexene and 1-octene.

The inventive ethylene based polymers, for example homopolymers and/or interpolymers (including copolymers) of ethylene and optionally one or more comonomers such as α-olefins may comprise at least 80 percent by weight of units derived from ethylene. All individual values and subranges from at least 80 weight percent are included herein and disclosed herein; for example, the inventive ethylene based polymers, for example homopolymers and/or interpolymers (including copolymers) of ethylene and optionally one or more comonomers such as α-olefins may comprise at least 82 percent by weight of units derived from ethylene; or in the alternative, at least 85 percent by weight of units derived from ethylene; or in the alternative, at least 90 percent by weight of units derived from ethylene; or in the alternative, from 80 to 100 percent by weight of units derived from ethylene; or in the alternative, from 90 to 100 percent by weight of units derived from ethylene.

The inventive ethylene based polymers, for example homopolymers and/or interpolymers (including copolymers) of ethylene and optionally one or more comonomers such as α-olefins may comprise at least 90 percent by moles of units derived from ethylene. All individual values and subranges from at least 90 mole percent are included herein and disclosed herein; for example, the inventive ethylene based polymers, for example homopolymers and/or interpolymers (including copolymers) of ethylene and optionally one or more comonomers such as α-olefins may comprise at least 93 percent by moles of units derived from ethylene; or in the alternative, at least 96 percent by moles of units derived from ethylene; or in the alternative, at least 97 percent by moles of units derived from ethylene; or in the alternative, from 90 to 100 percent by moles of units derived from ethylene; or in the alternative, from 90 to 99.5; or in the alternative, from 97 to 99.5 percent by moles of units derived from ethylene.

Any conventional polymerization processes may be employed to produce the inventive ethylene based polymers, for example homopolymers and/or interpolymers (including copolymers) of ethylene and optionally one or more comonomers such as α-olefins. Such conventional polymerization processes include, but are not limited to, solution polymerization process, gas phase polymerization process, slurry phase polymerization process, and combinations thereof using one or more conventional reactors e.g. loop reactors, isothermal reactors, fluidized bed gas phase reactors, stirred tank reactors, batch reactors in parallel, series, and/or any combinations thereof.

The inventive ethylene based polymers, for example homopolymers and/or interpolymers (including copolymers) of ethylene and optionally one or more comonomers such asα-olefins may, for example, be produced via solution-phase polymerization process using one or more loop reactors, isothermal reactors, and combinations thereof.

In general, the solution phase polymerization process occurs in one or more well-stirred reactors such as one or more loop reactors or one or more spherical isothermal reactors at a temperature in the range of from 120 to 300° C.; for example, from 160 to 190° C., and at pressures in the range of from 300 to 1500 psi; for example, from 400 to 750 psi. The residence time in solution phase polymerization process is typically in the range of from 2 to 30 minutes; for example, from 10 to 20 minutes. Ethylene, one or more solvents, one or more catalyst systems, e.g. a inventive catalyst system, optionally one or more cocatalysts, and optionally one or more comonomers are fed continuously to the one or more reactors. Exemplary solvents include, but are not limited to, isoparaffins. For example, such solvents are commercially available under the name ISOPAR E from ExxonMobil Chemical Co., Houston, Tex. The resultant mixture of the ethylene based polymer and solvent is then removed from the reactor and the ethylene based polymer is isolated. Solvent is typically recovered via a solvent recovery unit, i.e. heat exchangers and vapor liquid separator drum, and is then recycled back into the polymerization system.

In one embodiment, the ethylene based polymer may be produced via solution polymerization in a dual reactor system, for example a dual loop reactor system, wherein ethylene and optionally one or more α-olefins are polymerized in the presence of the inventive catalyst system, as described herein, and optionally one or more cocatalysts. In one embodiment, the ethylene based polymer may be produced via solution polymerization in a dual reactor system, for example a dual loop reactor system, wherein ethylene and optionally one or more α-olefins are polymerized in the presence of the inventive catalyst system, as described herein, and optionally one or more other catalysts. The inventive catalyst system, as described herein, can be used in the first reactor, or second reactor, optionally in combination with one or more other catalysts. In one embodiment, the ethylene based polymer may be produced via solution polymerization in a dual reactor system, for example a dual loop reactor system, wherein ethylene and optionally one or more α-olefins are polymerized in the presence of the inventive catalyst system, as described herein, in both reactors.

In another embodiment, the ethylene based polymer may be produced via solution polymerization in a single reactor system, for example a single loop reactor system, wherein ethylene and optionally one or more α-olefins are polymerized in the presence of the inventive catalyst system, as described herein, and optionally one or more cocatalysts.

In another embodiment, the ethylene based polymer may be produced via solution polymerization in a single reactor system, for example a single loop reactor system, wherein ethylene and optionally one or more α-olefins are polymerized in the presence of the inventive catalyst system, as described herein, optionally one or more other catalysts, and optionally one or more cocatalysts.

The procatalyst comprising the metal-ligand complex of formula (I) may be activated to form an active catalyst composition by combination with one or more cocatalysts, as described above, for example, a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to modified methyl aluminoxane (MMAO), bis(hydrogenated tallow alkyl)methyl, tetrakis(pentafluorophenyl)borate(1-) amine (RIBS-2), triethyl aluminum (TEA), and combinations thereof.

In another embodiment, the inventive ethylene based polymers, for example homopolymers and/or interpolymers (including copolymers) of ethylene and optionally one or more comonomers such as α-olefins may be produced via solution polymerization in a dual reactor system, for example a dual loop reactor system, wherein ethylene and optionally one or more α-olefins are polymerized in the presence of one or more catalyst systems.

In another embodiment, the inventive ethylene based polymers, for example homopolymers and/or interpolymers (including copolymers) of ethylene and optionally one or more comonomers such as α-olefins may be produced via solution polymerization in a single reactor system, for example a single loop reactor system, wherein ethylene and optionally one or more α-olefins are polymerized in the presence of one or more catalyst systems.

The inventive ethylene based polymers, for example homopolymers and/or interpolymers (including copolymers) of ethylene and optionally one or more comonomers such as α-olefins may further comprise one or more additives. Such additives include, but are not limited to, antistatic agents, color enhancers, dyes, lubricants, pigments, primary antioxidants, secondary antioxidants, processing aids, UV stabilizers, and combinations thereof. The inventive ethylene based polymers may contain any amounts of additives. The inventive ethylene based polymers may compromise from about 0 to about 10 percent by the combined weight of such additives, based on the weight of the inventive ethylene based polymers and the one or more additives. The inventive ethylene based polymers may further compromise fillers, which may include, but are not limited to, organic or inorganic fillers. Such fillers, e.g. calcium carbonate, talc, $Mg(OH)_2$, can be present in levels from about 0 to about 20, based on the weight of the inventive ethylene based polymers and the one or more additives and/or fillers. The inventive ethylene based polymers may further be blended with one or more polymers to form a blend.

EXAMPLES

The following examples illustrate the present invention but are not intended to limit the scope of the invention. Preparation of comparative procatalysts 2 and 3 are described in WO 2007136496 and US 2011/0282018, respectively, incorporated herein by reference to the extent that comparative procatalysts 2 and 3 are taught.

Specific Embodiment for Actual Synthesis of Catalyst

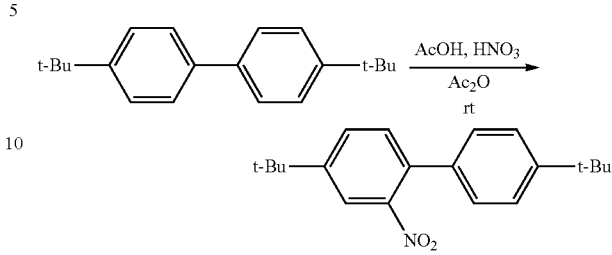

Preparation of 4,4'-di-tert-butyl-2-nitro-1,1'-biphenyl

To 4,4'-di-tert-butylbiphenyl (15.00 g, 56.30 mmol) was added acetic anhydride (300 mL) in a flask that was immersed in a room temperature water bath. To the suspension was added slowly dropwise a mixture of acetic acid (15 mL, 261.81 mmol) and fuming nitric acid (9.0 mL, 191.43 mmol) over the period of 10 minutes via a pressure equalizer addition funnel. The solid went into solution and turned yellow. The mixture was allowed to stir for 30 minutes and checked by GC/MS which showed reaction completion. The mixture was added to 2.5L of ice-water and stirred for 1 hour 15 minutes. The yellow precipitate was collected by vacuum filtration and washed with two 100-mL portions of ice-water. This crude solid was dissolved in 250 mL of methylene chloride. The solution was washed with water (250 mL) and 1M aqueous NaOH (250 mL). The organic phase was dried over anhydrous magnesium sulfate, filtered and concentrated under high vacuum to give the crude as a yellow solid. The crude solid was dissolved in minimum amount of chloroform for loading in the column cartridge. The crude was purified by flash chromatography using a Grace Reveleris 330 g column P/N 5146135 in an ISCO instrument and eluting with a gradient of 10-20% chloroform in hexanes to afford 11.04 g (63.0%) of the product as a light yellow solid.

$^1$H NMR (500 MHz, $CDCl_3$+TMS) δ 7.80 (d, J=2.0 Hz, 1H), 7.60 (dd, J=8.1, 2.0 Hz, 1H), 7.42 (d, J=8.4 Hz, 2H), 7.36 (d, J=8.1 Hz, 1H), 7.24 (d, J=8.3 Hz, 2H), 1.38 (s, 9H), 1.35 (s, 9H). $^{13}$C{$^1$H} NMR (126 MHz, $CDCl_3$+TMS) δ 151.72, 150.93, 149.22, 134.24, 133.20, 131.55, 129.26, 127.55, 125.58, 120.85, 34.86, 34.59, 31.29, 31.05.

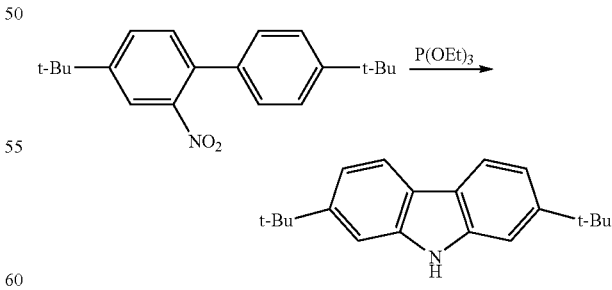

Preparation of 2,7-di-tent-butyl-9H-carbazole

To 4,4'-di-tert-butyl-2-nitro-1,1'-biphenyl (8.00 g, 25.69 mmol) in a glove box was added triethylphosphite (31.0 mL, 179.82 mmol). The mixture was removed from the glove box and taken to the hood. The mixture was placed under a nitrogen atmosphere and heated under gentle reflux (175° C. mantle temperature) while monitoring the reaction progress by GC/MS. Once the reaction was determined complete (4 hours) it was cooled and the condenser was removed from the reaction and the triethylphosphite was distilled off under vacuum with a short path column at 75° C. (mantle temperature) until a few mL of liquid remained. The flask was heated further to 125° C. and no additional distillation occurred (remaining liquid may be triethylphosphate which boils very high, expected by-product). The residue was allowed to cool to room temperature then diluted and washed with approximately 100 mL of 1:1 methanol:ice-water and filtered. The precipitate isolated by vacuum filtration and sticky residue remaining in the reaction flask were dissolved in approximately 300 mL of methylene chloride, dried with anhydrous magnesium sulfate, filtered and concentrated to give 9.41 g of crude as a yellow oil (approximately 80% carbazole product). This crude was taken up in 25% methylene chloride in hexanes and purified by flash chromatography using the same concentration of eluent and a Grace Reveleris 330g column to afford 4.70 g (66%) of pure compound as white powder.

$^1$H NMR (400 MHz, CDCl$_3$) δ 7.92 (d, J=8.2 Hz, 2H), 7.76 (s, 1H), 7.37 (d, J=1.3 Hz, 2H), 7.26 (dd, J=8.3, 1.6 Hz, 2H), 1.40 (s, 18H). $^{13}$C{$^1$H} NMR (126 MHz, C$_6$D$_6$) δ 148.93, 140.04, 120.97, 119.48, 117.29, 107.01, 77.25, 77.00, 76.75, 35.05, 31.79.

mL, 4.18 mmol). The flask was taken out of the glove box to the hood and heated under N$_2$ at 125° C. (heating mantle temperature). After 24 hours GC analysis shows about 76% conversion therefore additional anhydrous CuI (0.2 g, 1.05 mmol) slurried in dry toluene (0.9 mL) and N,N'-dimethylethylenediamine (0.45 mL, 4.18 mmol) was added and continued stirring at 125° C. for an additional 72 hours. GC analysis after 96 hours total shows trace amounts of carbazole remaining. The reaction was allowed to cool to room temperature and filtered through a small silica plug, washed with tetrahydrofuran and concentrated to give 24.47 g of crude product as a dark brown oil. This crude was recrystallized from hot hexanes (50 mL) to afford 13.48 g (90.9%) of the product as an off-white powder 98.12% pure by GC.

$^1$H NMR (500 MHz, CDCl$_3$) δ 8.00 (dd, J=8.2, 0.5 Hz, 2H), 7.44-7.49 (m, 2H), 7.45 (d, J=2.5 Hz, 1H), 7.38 (d, J=8.6 Hz, 1H), 7.30 (dt, J=8.2, 1.7 Hz, 2H), 7.19 (dd, J=1.7, 0.5 Hz, 1H), 7.10 (dd, J=1.7, 0.5 Hz, 1H), 5.25 (t, J=2.7 Hz, 1H), 3.71 (td, J=10.9, 2.9 Hz, 1H), 3.47 (dt, J=11.2, 4.0 Hz, 1H), 1.76 (ABq, J=14.6 Hz, 2H), 1.42 (s, 6H), 1.36 (s, 9H), 1.35 (s, 9H), 1.12-1.32 (m, 6H), 0.83 (s, 9H). $^{13}$C{$^1$H} NMR (101 MHz, CDCl$_3$) δ 151.18, 148.58, 148.51, 144.34, 142.00, 141.98, 127.78, 126.72, 126.44, 120.82, 120.73, 119.12, 119.08, 117.16, 117.10, 116.60, 106.88, 106.55, 97.19, 61.64, 57.13, 38.27, 35.10, 35.08, 32.48, 31.86, 31.81, 31.74, 31.43, 30.10, 25.01, 17.86.

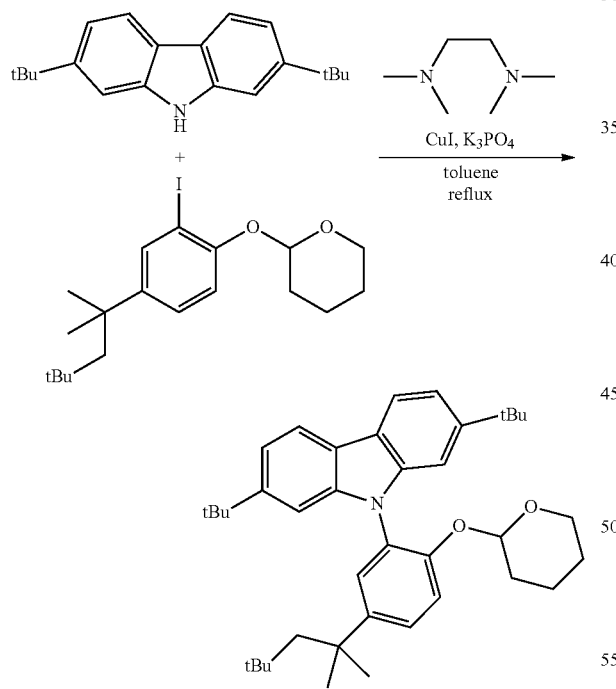

Preparation of 2,7-di-tert-butyl-9-(2-((tetrahydro-2H-pyran-2-yl)oxy)-5-(2,4,4-trimethylpentan-2-yl)phenyl)-9H-carbazole To a 250-mL three-necked round-bottomed flask in a glove box was added 2-(2-iodo-4-(2,4,4-trimethylpentan-2-yl)phenoxy)tetrahydro-2H-pyran (21.74 g, 52.22 mmol), 2,7-di-t-butylcarbazole (8.03 g, 28.73 mmol), K$_3$PO$_4$ (23.40 g, 110.24 mmol), anhydrous CuI (0.22 g, 1.16 mmol), dried toluene (85 mL) and N,N'-dimethylethylenediamine (0.45

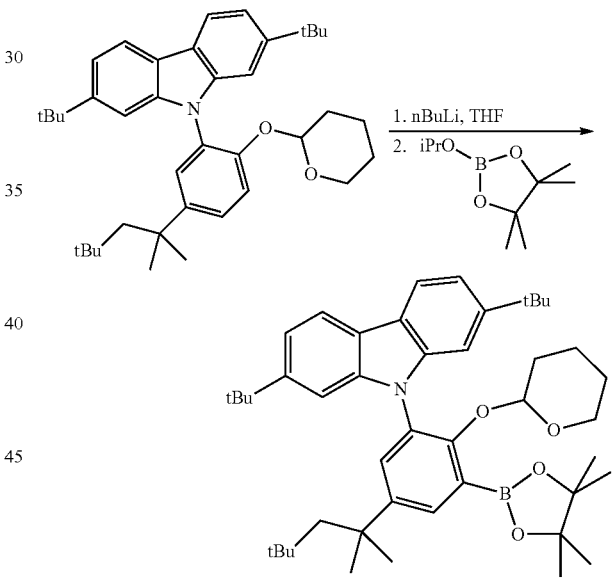

Preparation of 2,7-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole To an oven dried three-necked round-bottomed flask at 0-10° C. under N$_2$ atmosphere was added 2,7-di-tert-butyl-9-(2-((tetrahydro-2H-pyran-2-yl)oxy)-5-(2,4,4-trimethylpentan-2-yl)phenyl)-9H-carbazole (7.70 g, 13.56 mmol) and dry tetrahydrofuran (90 mL). This solution was cooled to 0-10° C. (ice-water bath) for about 15 minutes and 2.5 M n-butyllithium in hexanes (14 mL, 35.00 mmol) was added slowly. After stirring for 4 hours, 2-iso-propoxy-4,4,5,5-tetramethyl-1,3,2-dioxaborolane (7.0 mL, 34.31 mmol) was added slowly. The mixture was stirred for one hour at 0-10° C. before allowing the reaction to warm to room temperature and stirred for an additional 18 hours. To the reaction mixture was added cold saturated aqueous sodium bicarbonate (75 mL). The mixture was extracted with four 50-mL portions of methylene chloride. The organic phases were combined and washed with cold saturated aqueous sodium bicarbonate (200 mL), brine (200 mL), then dried over anhydrous magnesium sulfate, filtered and concentrated to give 9.43 g of crude as a golden foam. This crude was slurried in acetonitrile (75 mL) and allowed to sit for an hour at room temperature before isolating the solid by vacuum filtration. The solids were washed with a small portion of cold acetonitrile and dried under high vacuum to afford 8.12 g (86.3%) of the product as a white powder.

$^1$H NMR (400 MHz, CDCl$_3$) δ 7.97 (dd, J=8.2, 1.2 Hz, 2H), 7.81 (d, J=2.6 Hz, 1H), 7.50 (d, J=2.6 Hz, 1H), 7.29 (ddd, J=8.2, 4.5, 1.7 Hz, 2H), 7.20 (dd, J=12.9, 1.2 Hz, 2H), 5.02 (t, J=2.8 Hz, 1H), 2.81 (td, J=10.8, 2.8 Hz, 1H), 2.69 (dt, J=10.2, 2.9 Hz, 1H), 1.75 (ABq, J=14.6 Hz, 2H), 1.41 (s, 6H), 1.40 (s, 12H), 1.36 (s, 9H), 1.35 (s, 9H), 1.31 -0.94 (m, 6H), 0.82 (s, 9H). $^{13}$C NMR (101 MHz, cdcl$_3$) δ 156.00, 148.68, 148.53, 145.66, 141.80, 141.74, 133.45, 130.47, 129.15, 120.86, 120.61, 118.93, 118.88, 117.04, 107.51, 107.14, 100.80, 83.59, 61.08, 57.08, 38.40, 35.09, 32.49, 31.93, 31.80, 31.53, 31.16, 29.95, 25.06, 25.03, 24.89, 17.99.

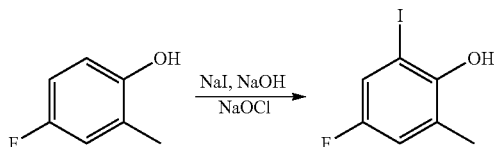

Preparation of 4-fluoro-2-iodo-6-methylphenol

To a round bottom flask equipped with an addition funnel under N$_2$ atmosphere at 0-10° C. was added methanol (150 mL), 4-fluoro-2-methylphenol (10.00 g, 79.28 mmol), NaI (14.29 g, 95.34 mmol) and NaOH (3.92 g, 98.00 mmol). This solution was allowed to stir for ~15 minutes at 0-10° C. before adding dropwise NaOCl (155 mL from 5% v/v in commercial bleach, 104.11 mmol) over the period of 2 hours. After bleach addition was complete, the reaction was allowed to stir for an additional hour at 0-10° C. GC Analysis showed ~50% conversion therefore additional NaI (7.16 g, 47.77 mmol) and bleach (75 mL, 50.38 mmol) was added (all at once) and stirred for another hour at 0-10° C. This time GC analysis showed full conversion therefore 50 mL of 10% wt. aqueous sodium thiosulfate was added to the reaction mixture. The reaction mixture was then acidified with 5% HCl, extracted into methylene chloride (500 mL), washed with 500 mL each of 10% wt. aqueous sodium thiosulfate, water, then brine, dried over anhydrous magnesium sulfate, filtered through a pad of silica gel then concentrated to give a dark red oil. This crude was purified by flash chromatography using a Grace Reveleris 330 g column P/N 5146135 in a Grace instrument eluting with 2% ethyl acetate in hexanes to afford 13.69 g (68.5%) of the pure product as off-white solid.

$^1$H NMR (400 MHz, CDCl$_3$) δ 7.19 (ddd, J=7.5, 3.0, 0.6 Hz, 1H), 6.88-6.82 (m, 1H), 5.09 (d, J=0.5 Hz, 1H), 2.28 (s, 4H). $^{13}$C{$^1$H} NMR (101 MHz, CDCl$_3$) δ 156.12 (d, J=242.5 Hz), 149.49 (d, J=2.7 Hz), 125.59 (d, J=7.8 Hz), 121.50 (d, J=25.2 Hz), 118.08 (d, J=22.4 Hz), 84.09 (d, J=9.6 Hz), 17.38 (d, J=1.2 Hz). $^{19}$F-NMR (CDCl$_3$) δ −123.15 (t, J=8.2 Hz).

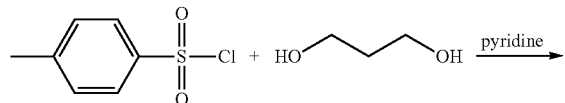

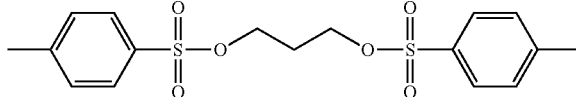

Preparation of Propane-1,3-diyl bis(4-methylbenzenesulfonate)

To a round bottom flask under N$_2$ atmosphere a solution of 1,3-propanediol (19.25 g, 252.96 mmol) in anhydrous pyridine (50 mL) was added dropwise over the period of 2 hours to a solution of 4-methylbenzene-1-sulfonyl chloride (115.74 g, 607.10 mmol) in anhydrous pyridine (200 mL) that was chilled at 0-10° C. The reaction mixture was allowed to stir for an additional 4 hours at 0-10° C. then poured into ice water (500 mL) at which time an off-white solid had precipitated. This precipitate was collected by vacuum filtration, washed with cold water (200 mL), dilute sulfuric acid (10 wt. %, 200 mL), 1M aqueous sodium carbonate (200 mL) and again with water (200 mL). This wet product was recrystallized from acetone to afford 82.35 g (84.7%) of product as white crystals.

$^1$H NMR (400 MHz, CDCl$_3$) δ 7.72 (d, J=8.3 Hz, 4H), 7.33 (d, J=8.5 Hz, 4H), 4.05 (t, J=6.0 Hz, 4H), 2.43 (s, 6H), 1.98 (p, J=6.0 Hz, 2H). $^{13}$C{$^1$H} NMR (101 MHz, CDCl$_3$) δ 144.99, 132.59, 129.90, 127.79, 65.82, 28.62, 21.57.

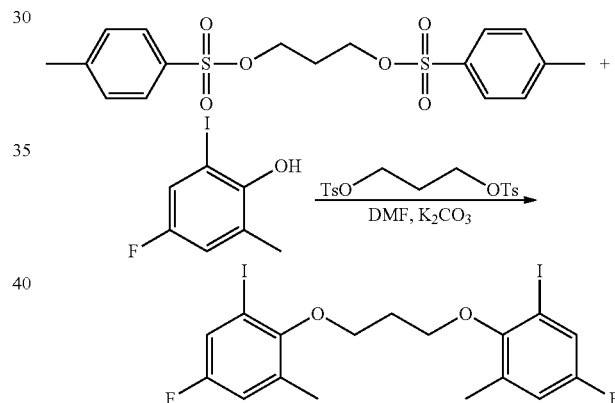

Preparation of 1,3-bis(4-fluoro-2-iodo-6-methylphenoxy)propane

To N,N-dimethylformamide (250 mL) was added 2-iodo-4-fluoro-6-methylphenol (13.09 g, 51.94 mmol), propane-1,3-diyl bis(4-methylbenzenesulfonate) (9.99 g, 25.98 mmol) and K$_2$CO$_3$ (15.08 g, 109.11 mmol). This mixture was heated at 100° C. for 30 minutes and then concentrated to dryness. The residue was taken up in a mixture of 50/50 methylene chloride/water (200 mL) and extracted with methylene chloride (3×100 mL). The organic phase was washed with 500 mL each of 2N aqueous NaOH, water then brine, dried over anhydrous magnesium sulfate, filtered through a pad of silica gel and concentrated to give 9.80 g (69.4%) of product as white powder.

$^1$H NMR (400 MHz, CDCl$_3$) δ 7.31 (m, 2H), 6.88 (m, 2H), 4.08 (t, J=6.5 Hz, 4H), 2.44 (p, J=6.5 Hz, 2H), 2.34 (s, 6H). $^{13}$C NMR (101 MHz, cdcl$_3$) δ 158.44 (d, J=247.1 Hz), 153.56 (d, J=3.0 Hz), 133.09 (d, J=8.3 Hz), 123.39 (d, J=24.8 Hz), 117.92 (d, J=22.3 Hz), 91.35 (d, J=9.5 Hz), 70.13 (d, J=1.0 Hz), 31.04, 17.43 (d, J=1.2 Hz). $^{19}$F NMR (376 MHz, CDCl$_3$) δ −118.17 (t, J=8.1 Hz).

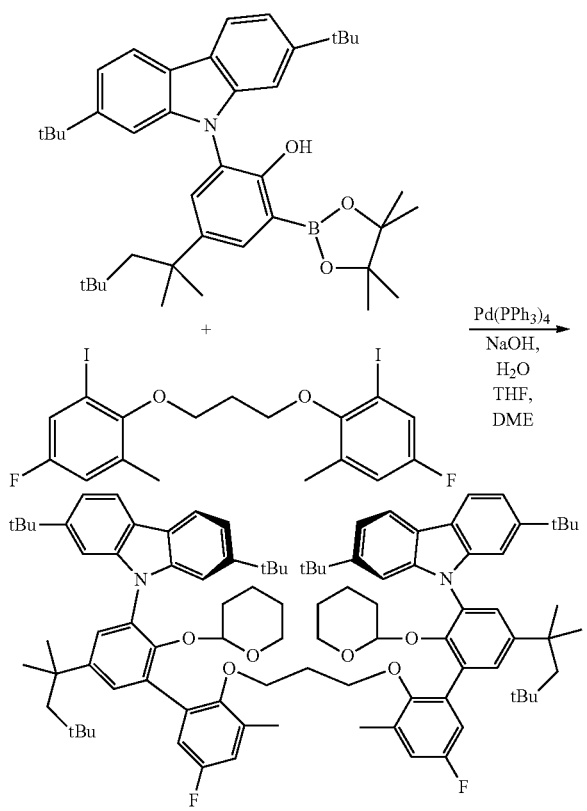

Preparation of 1,3-bis((3'-(2,7-di-tert-butyl-9H-carbazol-9-yl)-5-fluoro-3-methyl-2'-((tetrahydro-2H-pyran-2-yl)oxy)-5'-(2,4,4-trimethylpentan-2-yl)-[1,1'-biphenyl]-2-yl)oxy)propane To a round bottom flask under N₂ atmosphere was added 2,7-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (7.52 g, 9.89 mmol) (mmol adjusted based on a purity of 91.2% by HPLC), dimethoxyethane (120 mL), a solution of NaOH (1.30 g, 32.50 mmol) in water (35 mL), tetrahydrofuran (60 mL), and 1,3-bis(4-fluoro-2-iodo-6-methylphenoxy)propane (2.56 g, 4.70 mmol). The system was purged with N₂ for approximately 15 minutes and Pd(PPh₃)₄ (303 mg, 0.26 mmol) was added. The mixture was heated to reflux at 85° C. for 48 hours then allowed to cool to room temperature. Once cooled a precipitate was formed in the reaction flask which was isolated by vacuum filtration and dried under high vacuum for one hour to afford 6.10 g of crude protected ligand. This protected ligand was used as such in the next step.

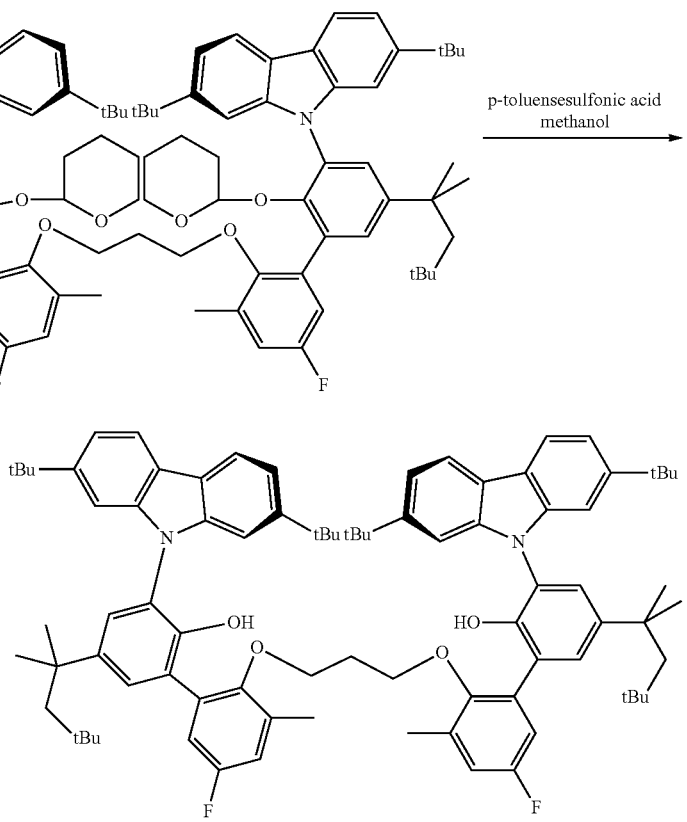

Preparation of 2',2'''-(propane-1,3-diylbis(oxy))bis (3-(2,7-di-tert-butyl-9H-carbazol-9-yl)-5'-fluoro-3'-methyl-5-(2,4,4-trimethylpentan-2-yl)-[1,1'-biphenyl]-2-ol) (DOC-6156 Ligand)

To the crude protected ligand was added a mixture of 1:1 methanol/tetrahydrofuran (200 mL) and approximately 100 mg of p-toluenesulfonic acid monohydrate. The solution was heated at 60° C. for 8 hours then allowed to cool and concentrated. The residue was dissolved in methylene chloride (250 mL), washed with brine (250 mL), dried over anhydrous magnesium sulfate, filtered through a pad of silica gel then concentrated to afford 4.92 g of crude ligand. This crude was purified by flash chromatography using a Grace Reveleris 330 g column P/N 5146135 in an ISCO instrument eluting with 2% ethyl acetate in hexanes to afford 4.23 g (71.7%) of the pure product as white powder.

$^1$H NMR (400 MHz, CDCl$_3$) δ 8.03 (dd, J=8.2, 0.5 Hz, 4H), 7.44 (dd, J=5.1, 2.4 Hz, 4H), 7.33 (dd, J=8.3, 1.7 Hz, 4H), 7.00 (dd, J=8.8, 3.0 Hz, 1H), 6.84 (ddd, J=8.7, 3.1, 0.6 Hz, 1H), 6.18 (s, 2H), 3.66 (t, J=6.4 Hz, 4H), 1.97 (s, 6H), 1.76 (s, 3H), 1.74 (pent, J=6.4 Hz, 2H), 1.40 (s, 12H), 1.30 (s, 36H), 0.83 (s, 18H). $^{13}$C NMR (101 MHz, CDCl$_3$) δ 158.82 (d, J=243.2 Hz), 150.16 (d, J=2.5 Hz), 149.09, 147.76, 142.87, 141.68, 133.48 (d, J=8.6 Hz), 132.89 (d, J=8.7 Hz), 129.12, 127.50, 126.28 (d, J=1.5 Hz), 124.99, 121.07, 119.51, 117.74, 117.18 (d, J=22.5 Hz), 116.07 (d, J=23.1 Hz), 106.20, 70.87, 57.17, 38.25, 35.06, 32.51, 31.91, 31.75, 31.66, 30.73, 16.44, 16.43. $^{19}$F-NMR (376 MHz, CDCl$_3$) δ −118.80 (t, J=8.5 Hz). HRMS (ESI, M+NH$_4^+$): (m/z) calcd for C$_{85}$H$_{108}$F$_2$N$_3$O$_4$ 1272.830, found 1272.830.

Preparation of Procatalyst 1

Ligand (0.4778 g, 0.38 mmol) and HfCl$_4$ (0.122 g, 0.38 mmol) were suspended in 35 mL of cold (−30° C.) toluene. To this mixture was added 0.56 mL of 3M diethyl ether solution of MeMgBr. The reaction mixture stayed pale yellow for about 20 min and then started to darken. After 1.5 hr of stirring, solvent was removed under reduced pressure. To the residue was added 20 mL of toluene followed by 25 mL of hexane. Suspension was filtered giving colorless solution. Solvent was removed under reduced pressure giving 0.367 g of white solid. Yield 66.0%. Crystals for X-ray analysis were grown from C$_6$D$_6$ in the NMR tube.

$^1$H NMR (400 MHz, toluene) δ 8.14 (d, J=8.2 Hz, 2H), 7.98 (d, J=8.2 Hz, 2H), 7.85 (d, J=1.6 Hz, 2H), 7.79 (d, J=2.5 Hz, 2H), 7.61 (d, J=1.6 Hz, 2H), 7.46 (dd, J=8.2, 1.6 Hz, 2H), 7.32 (d, J=2.5 Hz, 2H), 7.30 (dd, J=8.2, 1.6 Hz, 2H), 6.86 (dd, J=8.9, 3.2 Hz, 2H), 6.12 (d, J=5.1 Hz, 2H), 3.49 (dt, J=9.9, 4.9 Hz, 2H), 3.27 (dt, J=10.5, 5.5 Hz, 2H), 1.72 (d, J=14.4 Hz, 1H), 1.59 (d, J=14.4 Hz, 11H), 1.57 (s, 18H), 1.36-1.31 (m, 2H), 1.27 (s, 6H), 1.26 (s, 6H), 1.25 (s, 18H), 1.12 (s, 6H), 0.87 (s, 18H), −0.93 (s, 6H). $^{13}$C{$^1$H} NMR (101 MHz, toluene) δ 160.47 (d, J=246.3 Hz), 153.83, 149.41 (d, J=2.7 Hz), 149.38, 147.86, 142.19, 141.51, 140.54, 135.89 (d, J=8.6 Hz), 135.11 (d, J=8.9 Hz), 130.45 (d, J=1.4 Hz), 128.34, 127.81, 126.82, 123.46, 120.93, 120.27, 118.93, 117.48, 117.34 (d, J=23.5 Hz), 117.21 (d, J=22.5 Hz), 109.65, 107.68, 76.14, 57.86, 50.94, 38.28, 35.48, 35.24, 33.08, 32.76, 32.40, 32.02, 31.68, 30.32, 29.96, 16.45. $^{19}$F NMR (376 MHz, Benzene-d6) δ −115.22 (t, J=8.6 Hz).

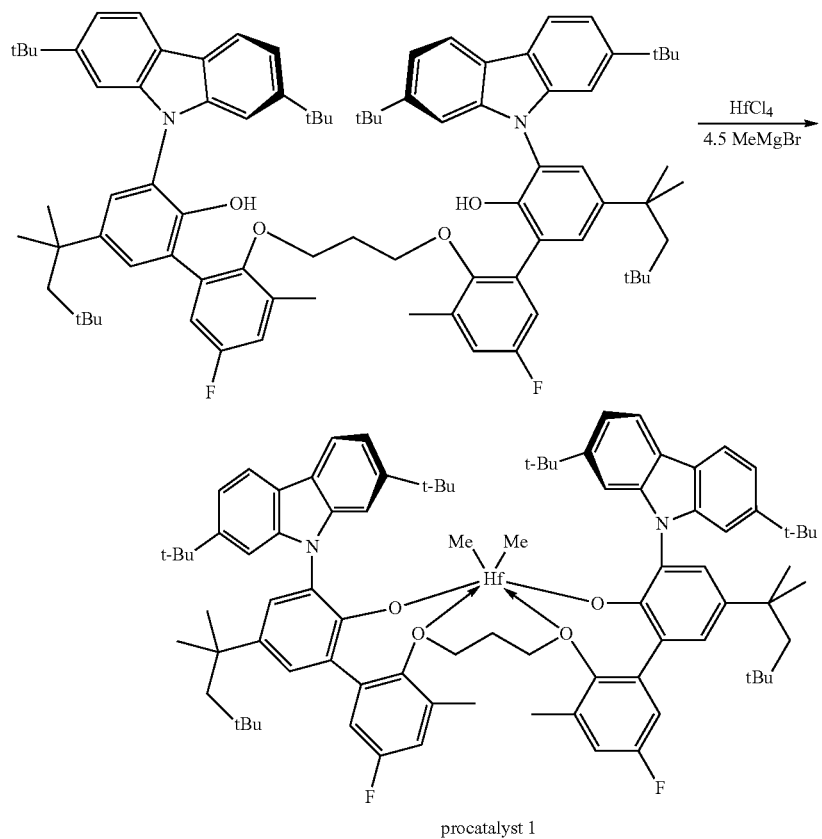

procatalyst 1

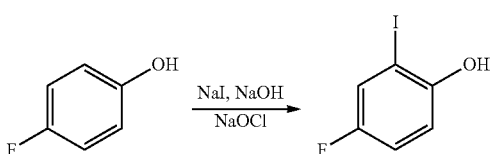

Preparation of 4-fluoro-2-iodophenol

To methanol (200 mL) at 0-10° C. was added 4-fluorophenol (8.00 g, 71.37 mmol), NaI (12.84 g, 85.64 mmol) and NaOH (3.43 g, 85.64 mmol). This solution was allowed to stir for ~15 minutes at 0-10° C. before adding dropwise NaOCl(133 mL of 5 wt. % solution from commercial bleach, 92.77 mmol) over the period of 1 hour then allowed to stir for an additional hour at 0-10° C. The reaction was quenched with 10% wt. aqueous sodium thiosulfate (50 mL) then the reaction mixture was then acidified with 10% HCl. The organic solution was extracted into methylene chloride (300 mL), washed with 500 mL each of 10% wt. sodium thiosulfate, water then brine, dried over anhydrous magnesium sulfate, filtered through a pad of silica gel then concentrated to give crude compound. This crude was purified by recrystallization from hexanes to afford 11.52 g (67.8%) of compound as white crystals.

$^1$H NMR (500 MHz, CDCl$_3$) δ 7.36 (dd, J=7.6, 2.9 Hz, 1H), 6.97 (ddd, J=8.9, 7.7, 2.9 Hz, 2H), 6.92 (dd, J=9.0, 4.9 Hz, 1H), 5.10 (s, 1H). $^{13}$C NMR (101 MHz, Chloroform-d) δ 156.42 (d, J=243.0 Hz), 151.45 (d, J=2.6 Hz), 124.34 (d, J=25.3 Hz), 116.83 (d, J=23.1 Hz), 115.08 (d, J=7.8 Hz), 84.23 (d, J=9.0 Hz). $^{19}$F NMR (376 MHz, CDCl$_3$) δ –122.52 (td, J=7.6, 4.9 Hz).

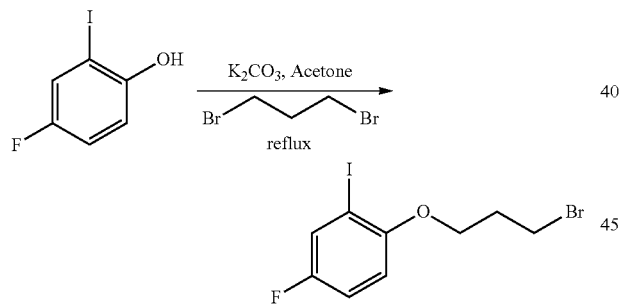

Preparation of 1-(3-bromopropoxy)-4-fluoro-2-iodobenzene)

A three-necked round bottom flask was equipped with a magnetic stir bar, septa, a condenser and a nitrogen gas inlet. The flask was charged with 4-fluoro-2-iodophenol (7.0020 g, 29.420 mmol), potassium carbonate (8.2954 g, 60.020 mmol), 1,3-dibromopropane (59.00 mL, 581.262 mmol), and acetone (200 mL). The mixture was stirred until complete dissolution and was refluxed overnight. The solution was sampled for GC/MS analysis (0.1 mL of sample diluted in acetone and filter) to determine reaction completion. After 16.5 hours, the reaction was allowed to cool to room temperature and filtered by vacuum filtration. The round bottom flask was washed with acetone (2×20 mL) and filtered as well. The filtrate was concentrated by rotary evaporation to remove acetone. The yellow solution that remained was distilled under vacuum (80-100° C. heating mantle temperature) to remove the remaining 1,3-dibromopropane. A crude brown oil was left which was analyzed by $^1$H NMR. The brown oil was dissolved in a small amount of hexanes and was purified by column chromatography on the Isco CombiFlash system using a 330 g Grace column and a gradient of 0-5% ethyl acetate in hexanes for 2 column volumes, then increasing to 5% ethyl acetate in hexanes until the product eluted. The fractions were analyzed by TLC and GC/MS. The pure fractions were combined and concentrated by rotary evaporation to afford the product as a yellow oil. The yellow oil was dried high under vacuum to afford 8.99 g (85.1%).

$^1$H-NMR (500 MHz, CDCl$_3$) δ 7.47 (dd, J=7.6, 3.0 Hz, 1H), 6.99 (ddd, J=9.0, 7.8, 3.0 Hz, 1H), 6.73 (dd, J=9.0, 4.6 Hz, 1H), 4.07 (t, J=5.7 Hz, 2H), 3.68 (t, J=6.4 Hz, 2H), 2.32 (p, J=6.2 Hz, 2H). $^{13}$C-NMR (126 MHz, CDCl$_3$) δ 156.64 (d, J=243.6 Hz), 153.60 (d, J=2.6 Hz), 125.81 (d, J=24.9 Hz), 115.49 (d, J=22.5 Hz), 112.22 (d, J=8.2 Hz), 67.02, 32.08, 30.15. $^{19}$F NMR (376 MHz, CDCl$_3$) δ –121.86–121.97 (m).

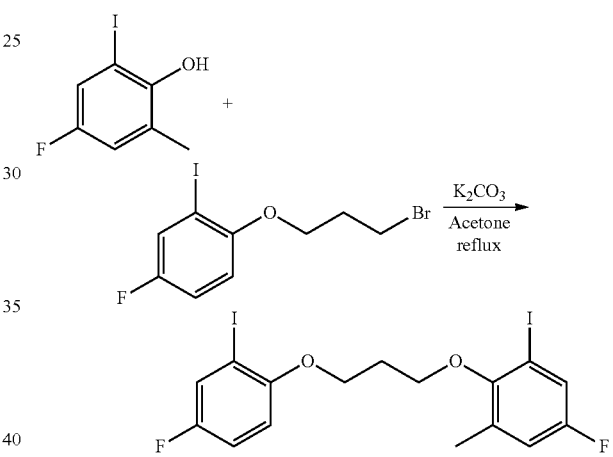

Preparation of 5-fluoro-2-(3-(4-fluoro-2-iodophenoxy)propoxy)-1-iodo-3-methylbenzene A three-necked round bottom flask was equipped with a magnetic stir bar, septa, a condenser and a nitrogen gas inlet. The flask was charged with 1-(3-bromopropoxy)-4-fluoro-2-iodobenzene (8.9856 g, 25.032 mmol), 4-fluoro-2-iodo-6-methylphenol (6.3096 g, 25.036 mmol), potassium carbonate (7.400 g, 53.542 mmol), and acetone (165 mL). The mixture was stirred until complete dissolution and was refluxed overnight. The solution was sampled for GC/MS analysis (0.1 mL of sample diluted in acetone and filter) to determine completion. After 16 hours, the reaction was allowed to cool to room temperature and filtered by vacuum filtration. The round bottom flask was washed with acetone (2×20 mL) and filtered as well. The filtrate was concentrated by rotary evaporation to afford the crude product as dark brown oil. The crude product was analyzed by $^1$H NMR. The dark brown oil was dissolved in a small amount of hexanes and was purified by column chromatography on the Isco CombiFlash system using a 330 g Grace column and a gradient of 0-5% ethyl acetate in hexanes for 2 column volumes, then increasing to 5% ethyl acetate in hexanes until the product eluted. The fractions were analyzed by TLC and GC/MS. The pure fractions were combined and concentrated by rotary evaporation to afford a pure product as a yellow solid. The yellow solid was dried under high vacuum to afford 11.55 g (87.1%).

$^1$H NMR (400 MHz, CDCl$_3$) δ 7.49 (dd, J=7.6, 3.0 Hz, 1H), 7.29 (ddd, J=7.5, 3.0, 0.7 Hz, 1H), 7.01 (ddd, J=9.0, 7.8, 3.0 Hz, 1H), 6.85 (ddd, J=8.6, 3.0, 0.8 Hz, 1H), 6.76 (dd, J=9.0, 4.6 Hz, 1H), 4.25 (t, J=5.9 Hz, 2H), 4.07 (t, J=6.0 Hz, 2H), 2.34 (p, J=5.9 Hz, 2H), 2.27 (d, J=0.7 Hz, 3H). $^{13}$C NMR (101 MHz, CDCl$_3$) δ 158.73 (d, J=181.2 Hz), 156.28 (d, J=178.1 Hz), 153.85 (d, J=2.1 Hz), 153.05 (d, J=3.1 Hz), 133.14 (d, J=8.2 Hz), 125.99 (d, J=25.1 Hz), 123.26 (d, J=24.8 Hz), 117.89 (d, J=22.2 Hz), 115.55 (d, J=22.4 Hz), 111.75 (d, J=8.1 Hz), 91.33 (d, J=9.3 Hz), 85.81 (d, J=8.2 Hz), 68.89 (d, J=1.3 Hz), 65.82, 29.86, 17.22 (d, J=1.3 Hz).$^{19}$F NMR (376 MHz, CDCl$_3$) δ −117.93 −−118.11 (m), −122.39−−122.55 (m).

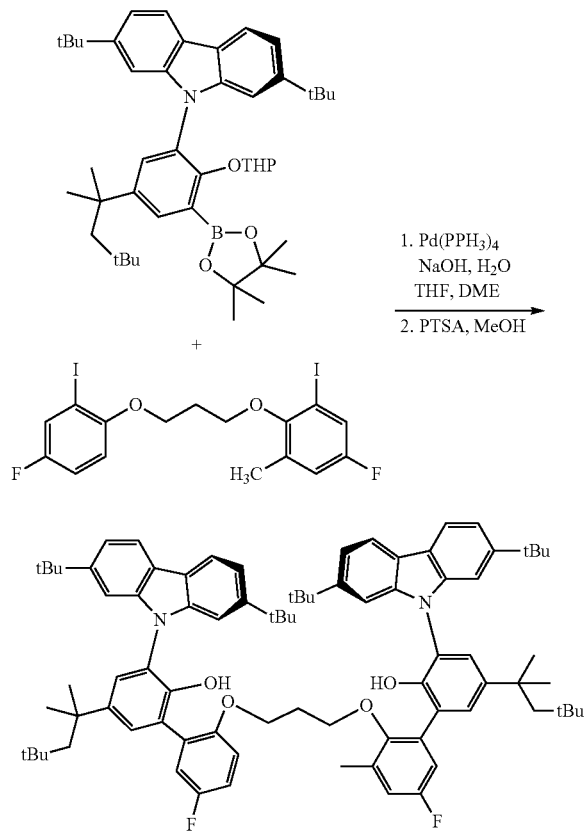

Preparation of 3-(2,7-di-tert-butyl-9H-carbazol-9-yl)-2'-(3-((3'-(2,7-di-tert-butyl-9H-carbazol-9-yl)-5-fluoro-2'-hydroxy-5'-(2,4,4-trimethylpentan-2-yl)-[1,1'-biphenyl]-2-yl)oxy)propoxy)-5'-fluoro-3'-methyl-5-(2,4,4-trimethylpentan-2-yl)-[1,1'-biphenyl]-2-ol A three-necked round bottom flask was equipped with a magnetic stir bar, septa, a condenser and a nitrogen gas inlet. The flask was charged with 2,7-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (9.4182 g, 13.575 mmol), 1,2-DME (170 mL), a solution of NaOH (1.8145 g, 45.438 mmol) in water (49 mL), THF (57 mL), and 5-fluoro-2-(3-(4-fluoro-2-iodophenoxy)propoxy)-1-iodo-3-methylbenzene (3.4233 g, 6.458 mmol). The solution was stirred and purged with nitrogen for approximately 15 minutes, then Pd(PPh$_3$)$_4$ (0.5432 g, 0.470 mmol) was added. The mixture was heated to reflux at 85° C. for 19 hours and was checked by TLC (5% ethyl acetate in hexanes) for completion. After 19 hours, the reaction was allowed to cool to room temperature. The mixture was transferred to a separatory funnel for a phase separation. The organic phase was dried over magnesium sulfate, filtered by vacuum filtration, and concentrated by rotary evaporation to afford a foamy golden orange solid (22.73 g) as a crude protected ligand. The crude ligand was analyzed by $^1$H NMR. The crude protected ligand was dissolved in a mixture of tetrahydrofuran (250 mL) and methanol (250 mL) then heated to 60° C. To the solution was added p-toluenesulfonic acid monohydrate (3.0380 g, 15.971 mmol) until the solution became acidic. The reaction was stirred at 60° C. overnight and was checked by TLC (5% ethyl acetate in hexanes) for completion. The reaction mixture was allowed to cool to room temperature and then concentrated by rotary evaporation to afford a brown sticky solid (15.13 g). The solid was analyzed by $^1$H NMR. The crude product was dissolved in chloroform and silica gel was added. The slurry was concentrated by rotary evaporation to afford a dry powdery mixture. The powdery mixture was loaded onto the Isco CombiFlash system and run using a 330 g Grace column and a gradient of 2-5% ethyl acetate in hexanes until the product eluded. The fractions were analyzed by TLC. The pure fractions were combined and concentrated by rotary evaporation to afford the product as a light yellow crystalline solid. To remove traces of ethyl acetate, the solid was dissolved in dichloromethane and concentrated by rotary evaporation to afford a light yellow crystalline solid (repeated twice). The solid was dried under high vacuum to afford 6.17 g (77.0%).

$^1$H NMR (400 MHz, CDCl$_3$) δ 8.12 (d, J=8.3 Hz, 2H), 8.08 (d, J=8.2 Hz, 2H), 7.55 (d, J=2.4 Hz, 1H), 7.51 (d, J=2.2 Hz, 1H), 7.43 (q, J=2.4 Hz, 2H), 7.40 (t, J=1.9 Hz, 2H), 7.38 (t, J=1.9 Hz, 2H), 7.19 (dd, J=8.9, 3.2 Hz, 1H), 7.17 (dd, J=1.6, 0.7 Hz, 2H), 7.15 (d, J=1.0 Hz, 2H), 7.09 (dd, J=8.8, 3.4 Hz, 1H), 6.88 (ddd, J=8.6, 3.1, 0.9 Hz, 1H), 6.79 (ddd, J=8.9, 7.8, 3.1 Hz, 1H), 6.63 (s, 1H), 6.48 (dd, J=9.1, 4.5 Hz, 1H), 5.71 (s,1H), 3.96 (t, J=6.7 Hz, 2H), 3.69 (t, J=5.5 Hz, 2H), 2.01 (s, 3H), 1.88 (p, J=6.0 Hz, 2H), 1.83 (s, 2H), 1.79 (s, 2H), 1.49 (s, 6H), 1.44 (s, 6H), 1.37 (s, 18H), 1.36 (s, 18H), 0.89 (s, 9H), 0.87 (s, 9H).$^{19}$F NMR (376 MHz, CDCl$_3$) δ −118.16 (t, J=8.7 Hz), −122.85−−122.93 (m).

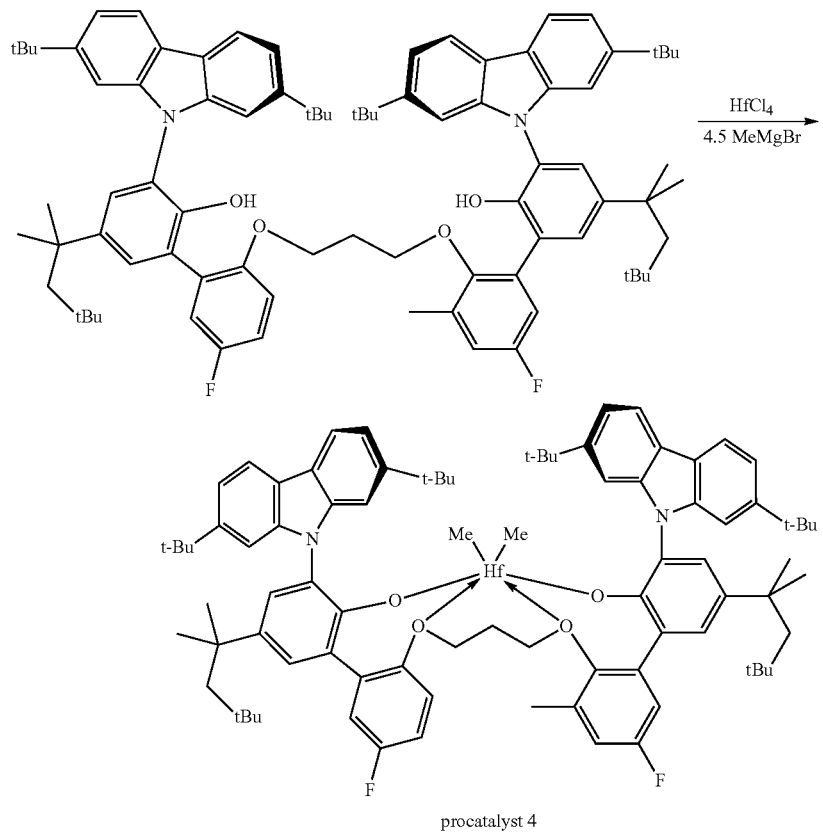

procatalyst 4

Preparation of Procatalyst 4

Reaction was set up in a glove box under nitrogen atmosphere. A jar was charged with $HfCl_4$ (0.1033 g, 0.3225 mmol) and toluene (20 mL). The slurry was cooled to −25° C. in the glove box freezer for 30 minutes. To the stirring cold slurry was added 3.0 M methylmagnesium bromide in diethyl ether (0.45 mL, 1.35 mmol). The mixture was stirred strongly for 2 minutes. The solid went in solution but the reaction solution was cloudy and yellowish. To the mixture was added the ligand (0.4000 g, 0.3221 mmol) as a solid. The vial containing the solid was rinsed with toluene (2.0 mL). The rinse solvent was added to the reaction mixture. Reaction was followed up by NMR. After stirring for 1.5 hour, the reaction mixture was filtered (fritted medium funnel). The cake was washed with two 10-mL portions of toluene. To the colorless filtrate solution was added hexanes (5 mL) and concentrated under vacuum to afford a white solid. To the solid was added toluene (30 mL) and stirred until almost all the solid went in solution. Then hexanes (25 mL) was added. The cloudy yellowish solution was filtered (syringe filter) and concentrated under high vacuum to afford 0.4317 g (92.5%) of the Hf-complex as a tan color solid.

Analytical sample for X-Ray was obtained by recrystallization from benzene-$d_6$.

$^1$H NMR (400 MHz, $C_6D_6$) δ 8.20 (dd, J=8.2, 0.5 Hz, 1H), 8.15 (dt, J=8.3, 0.6 Hz, 2H), 8.04 (dd, J=8.3, 0.6 Hz, 1H), 7.92 (d, J=1.3 Hz, 1H), 7.81 (d, J=2.5 Hz, 1H), 7.73 (ddd, J=13.7, 1.7, 0.6 Hz, 2H), 7.68 (d, J=2.3 Hz, 2H), 7.46 (dd, J=8.2, 1.7 Hz, 1H), 7.41 (dd, J=3.2, 1.6 Hz, 1H), 7.39 (dd, J=3.2, 1.9 Hz, 2H), 7.35 (dd, J=8.3, 1.7 Hz, 1H), 7.24 (d, J=2.5 Hz, 1H), 6.94 (dt, J=9.1, 3.2 Hz, 2H), 6.26 (ddd, J=8.9, 7.4, 3.2 Hz, 1H), 6.13 (dd, J=8.7, 3.1 Hz, 1H), 5.69 (dd, J=8.9, 5.0 Hz, 1H), 3.79 (dt, J=10.0, 5.2 Hz, 1H), 3.66 (dt, J=10.2, 4.9 Hz, 1H), 3.52 (dt, J=9.7, 5.6 Hz, 1H), 3.16 (dt, J=10.5, 5.2 Hz, 1H), 1.64-1.56 (m, 2H), 1.49 (s, 9H), 1.44 (s, 9H), 1.37-1.29 (m, 2H), 1.26 (s, 10H), 1.25 (s, 6H), 1.20-1.17 (m, 6H), 0.89 (s, 9H), 0.80 (s, 9H), −0.69 (s, 2H), −1.10 (s, 2H). $^{19}$F NMR (376 MHz, $C_6D_6$) δ −113.82 (ddd, J=9.0, 7.3, 5.0 Hz), −115.71 (t, J=8.4 Hz).

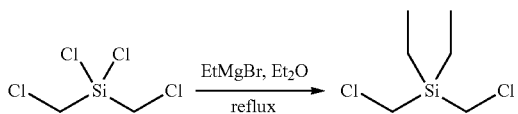

Preparation of bis(chloromethyl)diethylsilane

A three-necked round-bottomed flask was equipped with a magnetic stir bar, two septa, a condenser and a nitrogen gas inlet. The flask was placed under nitrogen atmosphere and charged with ethylmagnesium bromide (40 mL, 120 mmol) and diethyl ether (60 mL). To the solution was added bis(chloromethyldichlorosilane) (9.5002 g, 47.993 mmol) via syringe. The mixture was heated to reflux. After a few minutes the cloudy white mixture turned transparent and a white precipitate was observed. The reaction was refluxed for 5 hours and then allowed to stand overnight at room temperature. The mixture was filtered and the cake was washed with two 30-mL portions of diethyl ether. The filtrate was stirred slowly, cooled to 0° C. (ice water bath), and 0.1 M aqueous HCl (29 mL) was added slowly via addition funnel. While adding the 0.1M HCl, solids began to form. The mixture was transferred to a separatory funnel and white solids were left behind. The phases were separated and the white murky aqueous phase was extracted with two 15-mL portions of diethyl ether. The organic phases were combined, dried over magnesium sulfate, filtered by vacuum filtration, and concentrated by rotary evaporation to afford a light yellow oil as a crude product. The crude oil was dried under high vacuum for 1 hour to afford 7.6709 g (86.3%) of the product.

$^1$H NMR (500 MHz, CDCl$_3$) δ 2.94 (d, J=0.4 Hz, 4H), 1.03 (t, J=7.8 Hz, 4H), 0.80 (q, J=7.8 Hz, 3H). Reference: Anderson, W. K.; Kasliwal, R.; Houston, D. M.; Wamg, Y.; Narayanan, V. L.; Haugwitz, R. D.; Plowman, J. J. *Med. Chem.* 1995, 38, 3789-3797.

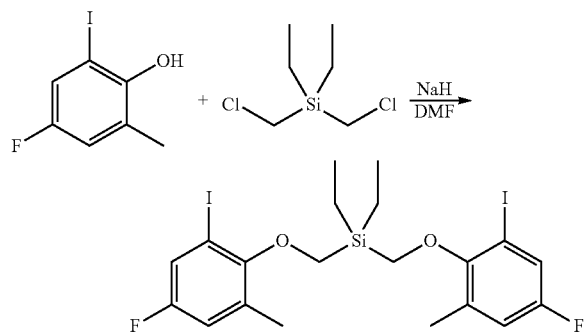

Preparation of diethylbis((4-fluoro-2-iodo-6-methylphenoxy)methyl)silane

A three necked round bottom flask was equipped with a condenser, two septa, a magnetic stir bar, and a nitrogen gas inlet. The flask was placed under nitrogen atmosphere and was charged with sodium hydride (95%, 0.4137 g, 16.376 mmol) and anhydrous N,N-dimethylformamide (8.5 mL). The slurry was cooled to 0° C. and a solution of 4-fluoro-2-iodo-6-methylphenol (4.2466 g, 16.850 mmol) in anhydrous N,N-dimethylformamide (8.5 mL) was added slowly via syringe at a rate to maintain control of the reaction (hydrogen evolution). The ice bath was removed and the resulting reddish mixture was stirred for 30 minutes. Then a solution of bis(chloromethyl)diethylsilane (1.3002 g, 7.022 mmol) in anhydrous N,N-dimethylformamide (4.5 mL) was added via syringe. The reaction mixture was heated to 60° C. for 17 hours. The reaction was allowed to cool to room temperature and then was cooled to 0° C. (ice-water bath). To the cooled solution was slowly added water (21.5 mL). A thick slim was left at the bottom of the flask when transferring the mixture to a separatory funnel. The flask was washed with some ethyl acetate to dissolve the slim and the solution was placed in the separatory funnel. The phases were separated and the aqueous phase was extracted with three 25-mL portions of ethyl acetate. The organic phases were combined and washed with 1M sodium hydroxide (35 mL), then brine (21.5 mL). The organic phase was dried over anhydrous magnesium sulfate, filtered by vacuum filtration, and concentrated by rotary evaporation to afford the crude product as a reddish-brown oil. The oil was dissolved in a small amount of hexanes and purified by column chromatography using a 330 g Grace column and a gradient of 0-5% dichloromethane in hexanes over 2 column volumes, the remaining at 5% dichloromethane in hexanes until the product eluded. The pure fractions were combined and concentrated by rotary evaporation to afford the product as a colorless oil. To remove traces of hexanes, the oil was dissolved in dichloromethane and concentrated by rotary evaporation to afford a colorless oil (repeated twice). The oil was dried under high vacuum to afford 3.1112 g (71.9%) of the product as a hazy white solid.

$^1$H NMR (400 MHz, CDCl$_3$) δ 7.29 (ddd, J=7.7, 3.1, 0.8 Hz, 2H), 6.85 (ddd, J=8.8, 3.1, 0.9 Hz, 2H), 3.86 (s, 4H), 2.32 (s, 6H), 1.21 (t, J=7.9 Hz, 6H), 1.10 -0.99 (m, 4H). $^{19}$F NMR (376 MHz, CDCl$_3$) δ −118.50 (t, J=8.1 Hz).

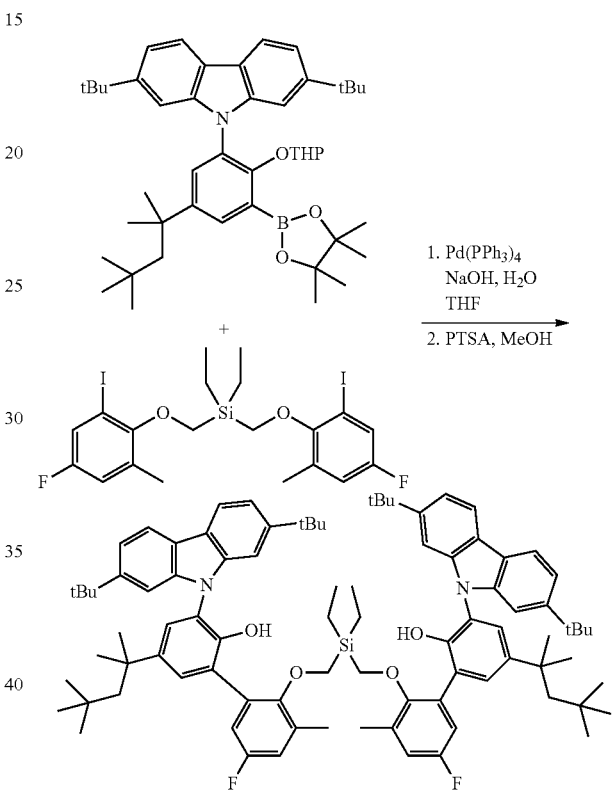

Preparation of 2',2'''-(((diethylsilanediyl)bis(methylene))bis(oxy))bis(3-(2,7-di-tert-butyl-9H-carbazol-9-yl)-5'-fluoro-3'-methyl-5-(2,4,4-trimethylpentan-2-yl)-[1,1'-biphenyl]-2-ol)

A three-necked round bottom flask was equipped with a magnetic stir bar, two septa, a condenser and a nitrogen gas inlet. The flask was charged with 2,7-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (7.4057 g, 10.674 mmol), a solution of sodium hydroxide (1.3599 g, 33.998 mmol) in water (33 mL), tetrahydrofuran (165 mL), and diethylbis((4-fluoro-2-iodo-6-methylphenoxy)methyl)silane (2.9865 g, 4.846 mmol). The solution was stirred and purged with nitrogen for approximately 45 minutes, then tetrakis(triphenylphosphine)palladium(0) (0.4079 g, 0.3529 mmol) was added. The mixture was heated to reflux at 60° C. for 23 hours and analyzed by HPLC for completion. After 24 hours, the reaction was allowed to cool to room temperature. The organic phase was separated, dried over magnesium sulfate and filtered by vacuum filtration. The solids were rinsed with dichloromethane. The filtrate was concentrated by rotary evaporation to afford a sticky golden orange solid as a crude protected ligand (10.9973 g). The ligand was dissolved in chloroform and silica gel was added. The slurry was concentrated by rotary evaporation to afford a dry powdery mixture of silica gel and ligand. The powdery mixture was loaded onto the Isco CombiFlash system and run using a 330 g Grace column and a gradient of 30% chloroform in hexanes for 6 column volumes (CV), increasing to 50% chloroform in hexanes over 3 CV, then remaining at 50% chloroform in hexanes until the product eluded. The pure fractions were combined and concentrated by rotary evaporation to afford a white crystalline solid (6.4445 g). The solid was dissolved in a mixture of tetrahydrofuran (33 mL) and methanol (33 mL) then heated to 60° C. To the solution was added para-toluenesulfonic acid monohydrate (0.1858 g, 0.9767 mmol). The reaction was stirred at 60° C. overnight and it was allowed to cool to room temperature. The mixture was concentrated by rotary evaporation to afford a crude light yellow crystalline solid (5.9845 g). The solid was dissolved in chloroform and silica gel was added. The slurry was concentrated by rotary evaporation to afford a dry powdery mixture of silica gel and ligand. The powdery mixture was loaded onto the Isco CombiFlash system and run using a 330 g Grace column and a gradient of 2% ethyl acetate in heptane until the product eluded. The pure fractions were combined and concentrated by rotary evaporation to afford a yellow crystalline solid. To remove traces of heptane, the solid was dissolved in dichloromethane and concentrated by rotary evaporation to afford a yellow crystalline solid (repeated twice). The solid was dried under high vacuum to afford 3.9614 g (61.6%) of a yellow crystalline solid.

$^1$H NMR (500 MHz, CDCl$_3$) δ 7.99 (d, J=8.2 Hz, 4H), 7.47 (d, J=2.4 Hz, 2H), 7.39 (d, J=2.4 Hz, 2H), 7.30 (dd, J=8.2, 1.6 Hz, 4H), 7.15 (broad s, 4H), 6.94 (dd, J=8.9, 3.1 Hz, 2H), 6.87 (dd, J=8.6, 3.2 Hz, 2H), 6.48 (broad s, 2H), 3.45 (s, 4H), 2.08 (s, 6H), 1.73 (s, 4H), 1.39 (s, 12H), 1.29 (s, 36H), 0.79 (s, 18H), 0.35 (broad s, 10H).

$^{19}$F NMR (376 MHz, CDCl$_3$) δ −118.32−−119.14 (broad s).

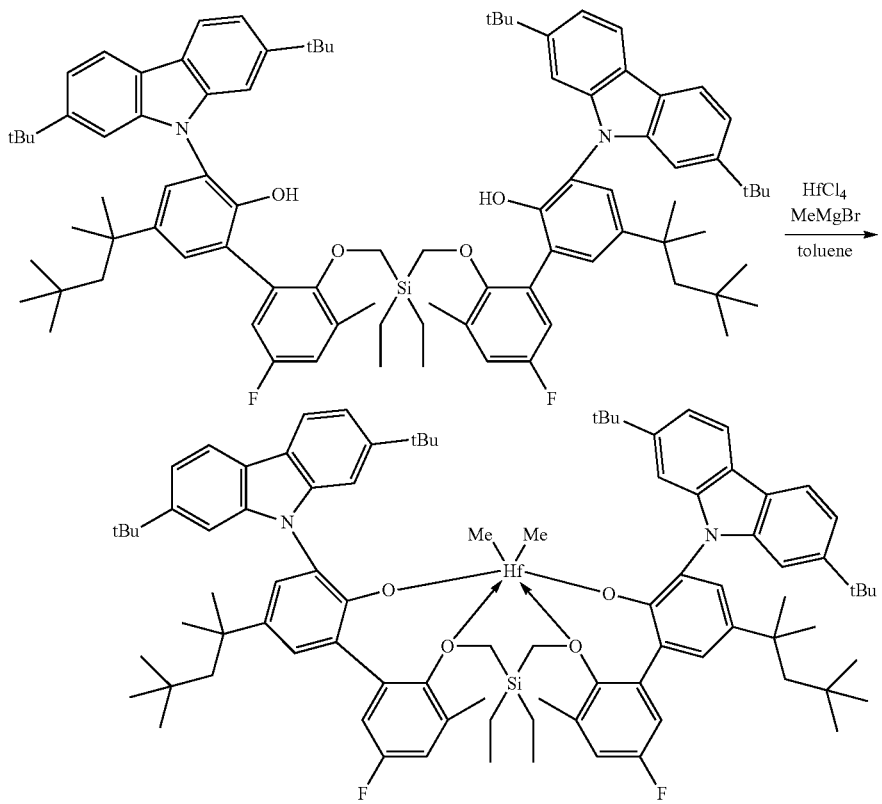

Preparation of procatalyst 5

Reaction was set up in a glove box under nitrogen atmosphere. A jar was charged with HfCl$_4$ (0.1258 g, 0.3928 mmol) and toluene (24 mL). The slurry was cooled to -25° C. in the glove box freezer for 30 minutes. To the stirring cold slurry was added 3.0 M methylmagnesium bromide in diethyl ether (0.55 mL, 1.65 mmol). The mixture was stirred strongly for 2 minutes. The solid went in solution but the reaction solution was cloudy and yellowish. To the mixture was added the ligand (0.5023 g, 0.3783 mmol) as a solid. The flask containing the solid was rinsed with toluene (3.0 mL). The rinse solvent was added to the reaction mixture. The reaction mixture was stirred at room temperature for 5.5 hours. To the yellow mixture was added hexanes (12 mL) and suspension was filtered. The transparent yellow solution was concentrated under vacuum overnight to afford 0.412 g (71.0%) of the product as a yellow solid.

$^1$H NMR (400 MHz, C$_6$D$_6$) δ 8.19 (d, J=8.2 Hz, 2H), 8.10 (d, J=8.3 Hz, 2H), 7.83 (d, J=1.6 Hz, 2H), 7.76 (d, J=2.5 Hz, 2H), 7.74 (d, J=1.6 Hz, 2H), 7.49 (dd, J=8.2, 1.6 Hz, 2H), 7.41-7.33 (m, 4H), 6.93 (dd, J=8.9, 3.2 Hz, 2H), 6.14 (dd, J=8.2, 3.3 Hz, 2H), 3.91 (d, J=14.1 Hz, 2H), 3.47 (d, J=14.1

Hz, 2H), 1.62 (d, J=14.6 Hz, 2H), 1.57 (d, J=14.4 Hz, 2H), 1.53 (s, 18H), 1.26 (d, J=2.5 Hz, 30H), 1.13 (s, 6H), 0.82 (s, 18H), 0.56 (t, J=8.0 Hz, 6H), 0.26-0.06 (m, 4H), −0.72 (s, 6H).

$^{19}$F NMR (376 MHz, C$_6$D$_6$) δ −116.35 (t, J=8.3 Hz).

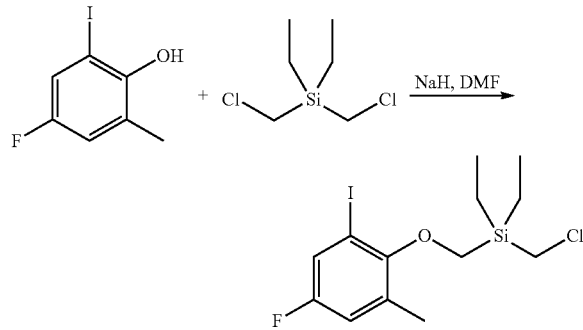

Preparation of (chloromethyl)diethyl((4-fluoro-2-iodo-6-methylphenoxy)methyl)silane A three-necked round-bottomed flask was equipped with two septa and a nitrogen gas inlet. The flask was placed under nitrogen atmosphere and was charged with sodium hydride (95%, 0.2496 g, 10.400 mmol) and anhydrous N,N-dimethylformamide (10.0 mL) was added via syringe. The slurry was cooled to 0° C. via ice water bath. To the slurry was added a solution of 4-fluoro-2-iodo-6-methylphenol (2.4753 g, 9.822 mmol) in anhydrous N,N-dimethylformamide (10.0 mL) via syringe at a rate to maintain control of the reaction (hydrogen evolution). The ice water bath was removed and the resulting brown solution was stirred for 30 minutes at room temperature. Another three-necked round-bottomed flask was equipped with a magnetic stir bar, two septa, an addition funnel, and a nitrogen gas inlet. The flask was placed under nitrogen atmosphere and charged with a solution of bis(chloromethyl)diethylsilane (5.4571 g, 29.471 mmol) in anhydrous N,N-dimethylformamide (12.5 mL) was added via syringe. The previous phenoxide solution from the reaction of 4-fluoro-2-iodo-6-methylphenol and sodium hydride in anhydrous N,N-dimethylformamide was added to the addition funnel via syringe. The solution was added drop-wise to the solution of bis(chloromethyl)diethylsilane in anhydrous N,N-dimethylformamide at room temperature. After 1 hour, the reaction was determined to be complete. The solids at the bottom of the flask were filtered by vacuum filtration and washed with two 5-mL portions of ethyl acetate. The filtrate was transferred to a round bottom flask and was cooled to 0° C. (ice water bath). To the cooled solution was slowly added 1M aqueous HCl (16.5 mL) via addition funnel (at a rate to maintain control of reaction). The reaction was concentrated by rotary evaporation (bath temperature=60-75° C.) to remove as much N,N-dimethylformamide as possible. The remaining solution was taken up in water (33 mL), transferred to a separatory funnel, and then ethyl acetate (33 mL) was added. The phases were separated. The aqueous phase was extracted with ethyl acetate (4×33 mL). The combined organic phases were washed with water (33 mL). A small emulsion formed between the two phases. A squirt of water was added and the funnel was swirled (repeated until the emulsion was gone). The phases were separated and the organic phase was dried over anhydrous magnesium sulfate, filtered by vacuum filtration, and concentrated by rotary evaporation to afford a crude reddish-brown oil. The oil was purified by column chromatography using a 330 g Grace column and a gradient of 100% hexanes until the product eluded. The pure fractions were combined and concentrated by rotary evaporation to afford the product as a pale yellow oil. To remove traces of ethyl acetate and hexanes, the oil was dissolved in dichloromethane and concentrated by rotary evaporation to afford a pale yellow oil (repeated twice). The oil was dried under high vacuum to afford 2.0211 g (51.4%) of the product as a pale yellow oil.

$^1$H NMR (400 MHz, CDCl$_3$) δ 7.29 (ddq, J=7.5, 3.1, 0.6 Hz, 1H), 6.85 (ddq, J=8.7, 3.1, 0.7 Hz, 1H), 3.74 (s, 2H), 3.09 (s, 2H), 2.31 (t, J=0.6 Hz, 3H), 1.14-1.08 (m, 6H), 0.94-0.86 (m, 4H).

$^{19}$F NMR (376 MHz, CDCl$_3$) δ −118.34 (t, J=8.0 Hz).

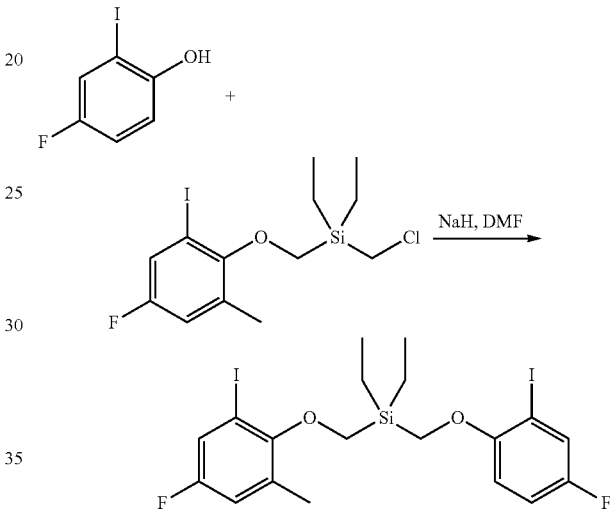

Preparation of diethyl((4-fluoro-2-iodo-6-methylphenoxy)methyl)((4-fluoro-2-iodophenoxy)methyl)silane A three-necked round-bottomed flask was equipped with a magnetic stir bar, two septa, a condenser, and a nitrogen gas inlet. The flask was placed under nitrogen atmosphere and charged with sodium hydride (0.2750 g, 11.458 mmol) and anhydrous N,N-dimethylformamide (10 mL). The solution was cooled to 0° C. (ice water bath). A solution of 4-fluoro-2-iodophenol (2.4893 g, 10.459 mmol) in anhydrous N,N-dimethylformamide (10 mL) was added slowly via syringe to maintain control of the reaction (hydrogen evolution). The resulting mixture was stirred for 30 minutes at room temperature. A solution of (chloromethyl)diethyl ((4-fluoro-2-iodo-6-methylphenoxy)methyl)silane (3.4893 g, 8.707 mmol) in anhydrous N,N-dimethylformamide (4.5 mL) was added slowly via syringe at room temperature. The resulting brown solution stirred at 60° C. After 18.5 hours, the reaction was allowed to cool down to room temperature. The reaction was further cooled to 0° C. (ice water bath) and water (25 mL) was slowly added (at a rate to maintain control of reaction). Solids formed during the addition and remained after the addition. The mixture was transferred to a 1-necked round bottom flask. The solids were dissolved in dichloromethane and transferred to the flask. The mixture was concentrated by rotary evaporation (bath temperature=60-75° C.) to remove as much N,N-dimethylformamide as possible. The remaining solution was taken up in water (30 mL), and transferred to a separatory funnel and then ethyl acetate (30 mL) was added. The phases were separated. The aqueous phase was extracted with four 30-mL portions of ethyl acetate. The combined organic phases were washed with two 21-mL portions of 1M aqueous NaOH. The organic phase was washed with brine (25 mL), dried over anhydrous magnesium sulfate, filtered by vacuum filtration, and concentrated by rotary evaporation to afford a crude orange oil (4.7914 g). The crude oil was purified by column chromatography using a 330 g Grace column and a gradient of 100% hexanes for 1 column volume (CV), increasing to 5% ethyl acetate in hexanes over 1 CV, the remaining at 5% ethyl acetate in hexanes until the product eluded. The pure fractions were combined and concentrated by rotary evaporation to afford the product as a yellow oil. To remove traces of ethyl acetate and hexanes, the oil was dissolved in dichloromethane and concentrated by rotary evaporation to afford a yellow oil (repeated twice). The oil was dried under high vacuum to afford 3.7015 g (70.6%) of the product as a yellow oil.

$^1$H NMR (400 MHz, CDCl$_3$) δ 7.48 (dd, J=7.6, 3.0 Hz, 1H), 7.29 (ddd, J=7.6, 3.0, 0.7 Hz, 1H), 7.03 (ddd, J=9.1, 7.8, 3.0 Hz, 1H), 6.88 (dd, J=9.1, 4.6 Hz, 1H), 6.83 (ddd, J=8.7, 3.1, 0.8 Hz, 1H) 3.91 (s, 2H), 3.88 (s, 2H), 2.27 (t, J=0.7 Hz, 3H), 1.21-1.14 (m, 6H), 1.03-0.95 (m, 4H).

$^{19}$F NMR (376 MHz, CDCl$_3$) δ −118.35 (dd, J=8.4, 7.7 Hz), −123.07 (td, J=7.7, 4.6 Hz).

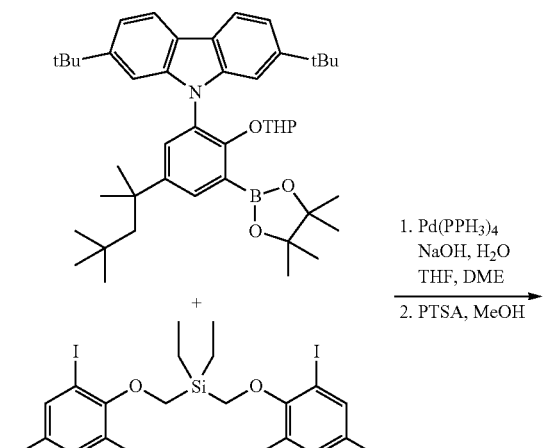

Preparation of 3-(2,7-di-tert-butyl-9H-carbazol-9-yl)-2'-(((((3'-(2,7-di-tert-butyl-9H-carbazol-9-yl)-5-fluoro-2'-hydroxy-5'-(2,4,4-trimethylpentan-2-yl)-[1,1'-biphenyl]-2-yl)oxy)methyl)diethylsilyl)methoxy)-5'-fluoro-3'-methyl-5-(2,4,4-trimethylpentan-2-yl)-[1,1'-biphenyl]-2-ol A three-necked round-bottomed flask was equipped with a magnetic stir bar, two septa, a condenser and a nitrogen gas inlet. The flask was placed under nitrogen atmosphere and charged with 2,7-di-tert-butyl-9-(2-((tetrahydro-2H-pyran-2-yl)oxy)-3-(4,4,5,5-tetramethyl-1,3,2-dioxaborolan-2-yl)-5-(2,4,4-trimethylpentan-2-yl)phenyl)-9H-carbazole (5.2419 g, 7.555 mmol), 1,2-dimethoxyethane (85 mL) a solution of sodium hydroxide (0.9106 g, 22.765 mmol) in water (25 mL), tetrahydrofuran (30 mL), and diethyl((4-fluoro-2-iodo-6-methylphenoxy)methyl)((4-fluoro-2-iodophenoxy)methyl)silane (1.9770 g, 3.283 mmol). The solution was stirred and purged with nitrogen for approximately 15 minutes, then tetrakis(triphenylphosphine)palladium(0) (0.2755 g, 0.2384 mmol) was added. The mixture was heated to reflux at 85° C. After 20 hours, the reaction was allowed to cool to room temperature. The mixture was transferred to a separatory funnel for a phase separation. The organic phase was dried over magnesium sulfate and filtered by vacuum filtration. The solids were rinsed with dichloromethane (2×20 mL). The filtrate was concentrated by rotary evaporation to afford a sticky golden orange solid as a crude protected ligand (15.6875 g). The crude protected ligand was dissolved in a mixture of tetrahydrofuran (65 mL) and methanol (65 mL) then heated to 60° C. Para-toluenesulfonicacid monohydrate (0.2492 g, 1.310 mmol) was added to the solution. The reaction was stirred at 60° C. overnight and was checked by TLC for completion. The ligand was concentrated down to a sticky golden orange solid (15.3856 g). The ligand was dissolved in chloroform and silica gel was added. The slurry was concentrated by rotary evaporation to afford a dry powdery mixture of silica gel and ligand. The powdery mixture was split for two separate columns. Both columns were loaded onto the Isco CombiFlash system and run using a 330 g Grace column. The first column was run using a gradient of 30% dichloromethane in hexanes until the product eluded. The fractions were analyzed by TLC and all fractions containing just the product were concentrated by rotary evaporation to afford an off white crystalline solid. The solid was dried under high vacuum to afford 1.4 g. The second column was run using a gradient of 30% dichloromethane in hexanes for 2 column volumes, then increasing to 35% dichloromethane in hexanes until the product eluded. The fractions were analyzed by TLC which showed a combination of the ligand with other impurities. All fractions containing the majority of the product were concentrated by rotary evaporation to afford 2.1863 g of an off white crystalline solid. The solid was dissolved in chloroform and silica gel was added. The slurry was concentrated by rotary evaporation to afford a dry powdery mixture of silica gel and ligand. The powdery mixture was loaded onto the Isco CombiFlash system and run using a 330 g Grace column and a gradient of 30% dichloromethane in hexanes and then increasing to 35% dichloromethane in hexanes until the product eluded. The fractions containing the ligand were concentrated by rotary evaporation to afford an off white crystalline solid. The solid was dried under high vacuum to afford 0.4672 g of an off white crystalline solid. The overall yield was 1.8672 g (23.1%) of the product as an off white crystalline solid.

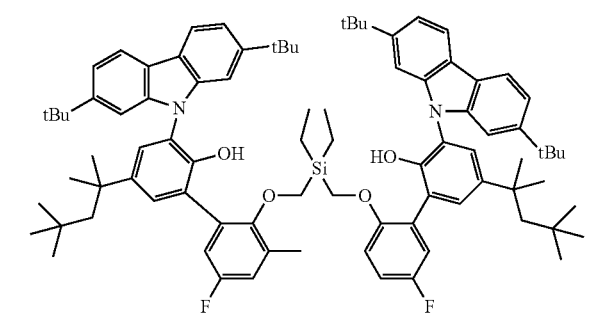

¹H NMR (400 MHz, CDCl₃) δ 8.05 (dd, J=8.2, 0.6 Hz, 2H), 7.99 (dd, J=8.3, 0.7 Hz, 2H), 7.48 (d, J=2.4 Hz, 1H), 7.40 (d, J=2.4 Hz, 1H), 7.35 (d, J=2.4 Hz, 1H), 7.32-7.28 (m, 4H), 7.24 (d, J=2.4 Hz, 1H), 7.09 (d, J=1.6 Hz, 2H), 7.00 (dd, J=8.9, 3.2 Hz, 1H), 6.95 (dd, J=9.0, 3.2 Hz, 1H), 6.82 (dd, J=8.7, 3.0 Hz, 1H), 6.75 (s, 1H), 6.65 (ddd, J=8.9, 7.8, 3.1 Hz, 1H), 6.18 (dd, J=9.1, 4.5 Hz, 1H), 5.64 (s, 1H), 3.60-3.47 (broad m, 2H), 3.38 (s, 2H), 1.90 (s, 3H), 1.74 (broad s, 2H), 1.69 (s, 2H), 1.40 (s, 6H), 1.35-1.33 (m, 6H), 1.30 (s, 18H), 1.28 (s, 18H), 0.79 (s, 9H), 0.77 (s, 9H), 0.43 (t, J=7.7 Hz, 6H), 0.36 -0.31 (broad m, 4H).¹⁹F NMR (376 MHz, CDCl₃) δ 6 −118.46 (t, J=8.9 Hz), −123.65 (m).

¹H NMR (400 MHz, C₆D₆) δ 8.19 (dd, J=8.2, 0.5 fHz, 1H), 8.18-8.15 (m, 2H), 8.04 (dd, J=8.3, 0.6 Hz, 1H), 7.82 (ddd, J=2.4, 1.7, 0.6 Hz, 2H), 7.76 (d, J=2.5 Hz, 1H), 7.72 (dd, J=1.7, 0.6 Hz, 1H), 7.66 (dd, J=1.8, 0.6 Hz, 1H), 7.63 (d, J=2.6 Hz, 1H), 7.47-7.44 (two m, 2H), 7.41 (ddd, J=8.3, 6.7, 1.7 Hz, 2H), 7.35 (dd, J=8.3, 1.7 Hz, 1H), 7.21 (d, J=2.6 Hz, 1H), 6.99-6.95 (two m, 2H), 6.55 (ddd, J=9.1, 7.3, 3.2 Hz, 1H), 6.11 (ddd, J=8.4, 3.2, 0.7 Hz, 1H), 5.44 (dd, J=9.1, 4.8 Hz, 1H), 4.51 (d, J=13.7 Hz, 1H), 4.37 (d, J=14.5 Hz, 1H), 3.41 (d, J=13.7 Hz, 1H), 3.28 (d, J=14.5 Hz, 1H), 1.60 (s, 2H), 1.54 (s, 2H), 1.45 (s, 8H), 1.41 (s, 8H), 1.33 (d, J=1.1 Hz, 4H), 1.28 (d, J=0.4 Hz, 17H), 1.23 (s, 3H), 1.19 (s, 3H),

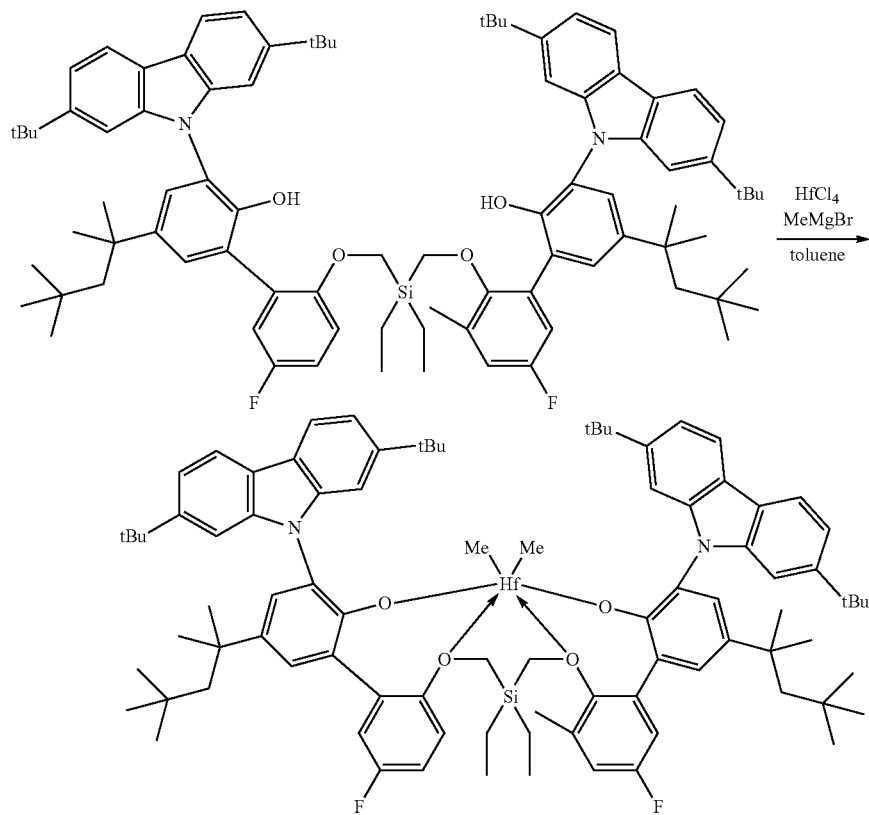

Preparation of procatalyst 6

Reaction was set up in a glove box under nitrogen atmosphere. A jar was charged with HfCl₄ (0.0489 g, 0.1522 mmol) and toluene (12 mL). The slurry was cooled to −25° C. in the glove box freezer for 30 minutes at −25° C. To the stirring cold slurry was added cold 3.0 M methylmagnesium bromide in diethyl ether (0.20 mL, 0.60 mmol). The mixture was stirred strongly for 2 minutes. The solid went in solution. The reaction solution was cloudy and pale yellow. To the mixture was added the ligand (0.2000 g, 0.1522 mmol) as a solid at a rate to maintain control of the reaction. The flask containing the solid was rinsed with toluene (about 2 mL). The rinse solvent was added to the reaction mixture. The reaction mixture was stirred at room temperature for 3 hours. To the brown mixture was added hexanes (12 mL). The mixture was filtered. The filtered was concentrated under high vacuum to afford 0.2341 g (101.1%) of the desired product. Excess mass was attributed to residual toluene trap in the solid.

0.92 (s, OH), 0.83 (s, 9H), 0.82 (s, 8H), 0.54 (td, J=7.9, 2.7 Hz, 6H), 0.25-0.09 (m, 3H), 0.10--0.06 (m, 1H), −0.58 (d, J=0.5 Hz, 3H), −1.07 (d, J=0.5 Hz, 3H).
¹⁹F NMR (376 MHz, C₆D₆) δ −116.21(m), -116.30 (t, J=8.8 Hz).

Preparation of Ethylene Based Polymers in a Single Reactor

All raw materials (ethylene, 1-octene) and the process solvent (a narrow boiling range high-purity isoparaffinic solvent trademarked Isopar E commercially available from ExxonMobil Corporation) are purified with molecular sieves before introduction into the reaction environment. Hydrogen is supplied in pressurized cylinders as a high purity grade and is not further purified. The reactor monomer feed (ethylene) stream is pressurized via mechanical compressor to above reaction pressure at 525 psig. The solvent and comonomer (1-octene) feed is pressurized via mechanical positive displacement pump to above reaction pressure at 525 psig. The individual catalyst components are manually batch diluted to specified component concentrations with purified solvent (Isopar E) and pressured to above reaction pressure at 525 psig. All reaction feed flows are measured with mass flow meters and independently controlled with computer automated valve control systems.

The continuous solution polymerization reactor consists of a liquid full, non-adiabatic, isothermal, circulating, and independently controlled loop. The reactor has independent control of all fresh solvent, monomer, comonomer, hydrogen, and catalyst component feeds. The combined solvent, monomer, comonomer and hydrogen feed to the reactor is temperature controlled to anywhere between 5° C. to 50° C. and typically 25° C. by passing the feed stream through a heat exchanger. The fresh comonomer feed to the polymerization reactor is fed in with the solvent feed. The total fresh feed to each polymerization reactor is injected into the reactor at two locations with roughly equal reactor volumes between each injection location. The fresh feed is controlled typically with each injector receiving half of the total fresh feed mass flow. The catalyst components are injected into the polymerization reactor through specially designed injection stingers and are each separately injected into the same relative location in the reactor with no contact time prior to the reactor. The primary catalyst component feed is computer controlled to maintain the reactor monomer concentration at a specified target. The cocatalyst components are fed based on calculated specified molar ratios to the primary catalyst component. Immediately following each fresh injection location (either feed or catalyst), the feed streams are mixed with the circulating polymerization reactor contents with Kenics static mixing elements. The contents of each reactor are continuously circulated through heat exchangers responsible for removing much of the heat of reaction and with the temperature of the coolant side responsible for maintaining isothermal reaction environment at the specified temperature. Circulation around each reactor loop is provided by a screw pump.

The effluent from the first polymerization reactor (containing solvent, monomer, comonomer, hydrogen, catalyst components, and molten polymer) exits the first reactor loop and passes through a control valve (responsible for maintaining the pressure of the first reactor at a specified target). As the stream exits the reactor it is contacted with water to stop the reaction. In addition, various additives such as anti-oxidants, can be added at this point. The stream then goes through another set of Kenics static mixing elements to evenly disperse the catalyst kill and additives.

Following additive addition, the effluent (containing solvent, monomer, comonomer, hydrogen, catalyst components, and molten polymer) passes through a heat exchanger to raise the stream temperature in preparation for separation of the polymer from the other lower boiling reaction components. The stream then enters a two stage separation and devolatization system where the polymer is removed from the solvent, hydrogen, and unreacted monomer and comonomer. The recycled stream is purified before entering the reactor again. The separated and devolatized polymer melt is pumped through a die specially designed for underwater pelletization, cut into uniform solid pellets, dried, and transferred into a hopper. After validation of initial polymer properties the solid polymer pellets are manually dumped into a box for storage. Each box typically holds ~1200 pounds of polymer pellets.

The non-polymer portions removed in the devolatilization step pass through various process steps which separate most of the ethylene which is removed from the system to a vent destruction unit (it is recycled in manufacturing units). Most of the solvent is recycled back to the reactor after passing through purification beds. This solvent can still have unreacted co-monomer in it that is fortified with fresh co-monomer prior to re-entry to the reactor. This fortification of the co-monomer is an essential part of the product density control method. This recycle solvent can still have some hydrogen which is then fortified with fresh hydrogen to achieve the polymer molecular weight target. A very small amount of solvent leaves the system as a co-product due to solvent carrier in the catalyst streams and a small amount of solvent that is part of commercial grade co-monomers.

Polymerization conditions in a single reactor, as described above, for Comparative PE-A, Comparative PE-B, Comparative PE-C, Comparative PE-D, Inventive PE-1, Inventive PE-2, and Inventive PE-3 are reported in Table 1. Properties for Comparative PE-A, Comparative PE-B, Comparative PE-C, Comparative PE-D, Inventive PE-1, Inventive PE-2, and Inventive PE-3 were tested, and reported in Table 1.

TABLE I

| | Units | Comparative PE-A | Comparative PE-B | Comparative PE-C | Comparative PE-D | Inventive PE-1 | Inventive PE-2 | Inventive PE-3 |
|---|---|---|---|---|---|---|---|---|
| Procatalyst | n/a | 2 | 3 | 3 | 2 | 1 | 1 | 1 |
| Activator | n/a | RIBS-2 | RIBS-2 | RIBS-2 | RIBS-2 | RIBS-2 | RIBS-2 | RIBS-2 |
| Scavenager | n/a | MMAO | MMAO | MMAO | MMAO | MMAO | MMAO | MMAO |
| Reactor Temperature | ° C. | 190 | 180 | 180 | 190 | 180 | 180 | 190 |
| C2 conversion | % | 91.7 | 92.0 | 91.0 | 91.6 | 92.0 | 90.2 | 91.3 |
| H2 concentration | mol % | 0.17 | 0.06 | 0.33 | 0.19 | 0.5 | 0.49 | 0.01 |
| C8/C2 molar ratio | unitless | 0.0974 | 0.0974 | 0.0759 | 0.0549 | 0.0974 | 0.1560 | 0.3607 |
| C2 feed | (g/L) | 7.1 | 6.0 | 9.3 | 6.9 | 6.1 | 10.0 | 7.0 |
| Al/catalyst | unitless | 13.7 | 24.8 | 22.4 | 15.1 | 25.0 | 24.0 | 25.1 |
| Efficiency[a] | $10^6$ lbs polymer/ lb M | 0.59 | 2.79 | 3.59 | 0.80 | 2.56 | 3.38 | 2.22 |
| $r_{I2}$ | unitless | 25.6 | 98.1 | 87.8 | 24.9 | 208.8 | 207.6 | 290.0 |
| Density | g/cm$^3$ | 0.9109 | 0.9290 | 0.9326 | 0.9219 | 0.9370 | 0.9375 | 0.9219 |
| $I_2$ | g/10 min | 0.94 | 0.94 | 0.93 | 0.52 | 0.98 | 1.03 | 0.51 |
| $I_{10}/I_2$ | g/10 min | 8.89 | 8.36 | 8.08 | 10.72 | 5.39 | 5.37 | 6.10 |
| $M_W$ | g/mol | 88838 | 95531 | 95814 | 93879 | 115016 | 113785 | 126312 |

TABLE I-continued

| | Units | Comparative PE-A | Comparative PE-B | Comparative PE-C | Comparative PE-D | Inventive PE-1 | Inventive PE-2 | Inventive PE-3 |
|---|---|---|---|---|---|---|---|---|
| $M_N$ | g/mol | 45553 | 39990 | 38992 | 45450 | 58285 | 60016 | 62996 |
| PDI ($M_W/M_N$) | unitless | 2.04 | 2.39 | 2.46 | 2.07 | 1.97 | 1.90 | 2.01 |
| $T_M$ (DSC) | °C. | 105.4 | 121.1 | 124.0 | 117.3 | 128.0 | 125.8 | 117.9 |
| $T_C$ (DSC) | °C. | 93.3 | 108.7 | 110.6 | 103.1 | 114.9 | 113.3 | 104.8 |
| long chain branches (LCB) | LCB/ 10000 C | not measured | not measured | 0.331 | 0.177 | 0.132 | 0.154 | not measured |
| Zr amount in resin | ppm(w) | 1.6 ± 0.1 | n.d. | n.d. | 1.2 ± 0.1 | n.d. | n.d. | n.d. |
| Hf amount in resin | ppm(w) | n.d. | 0.29 ± 0.01 | 0.16 ± 0.01 | n.d. | 0.27 ± 0.01 | 0.24 ± 0.01 | 0.28 ± 0.01 |
| Al amount in resin | ppm(w) | 7.8 ± 0.4 | 1.7 ± 0.1 | 2.7 ± 0.2 | 5.8 ± 0.3 | 1.9 ± 0.1 | 1.4 ± 0.1 | 2.1 ± 0.2 | a. For the efficiency units, M represents the active metal in the catalyst.

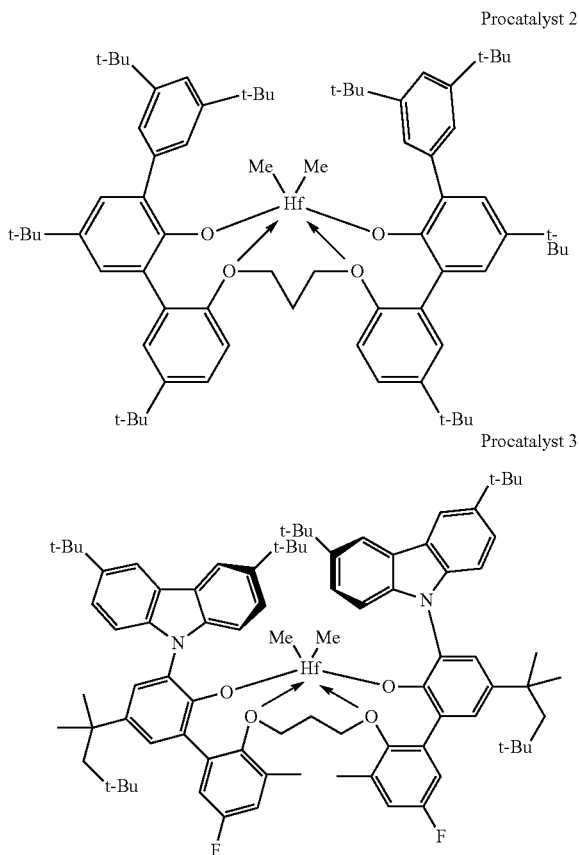

Preparation of Ethylene Based Polymers in a Dual Reactor

All raw materials (ethylene, 1-octene) and the process solvent (a narrow boiling range high-purity isoparaffinic solvent commercially available under the tradename Isopar E from ExxonMobil Corporation) are purified with molecular sieves before introduction into the reaction environment. Hydrogen is supplied in pressurized cylinders as a high purity grade and is not further purified. The reactor monomer feed (ethylene) stream is pressurized via mechanical compressor to a pressure that is above the reaction pressure, approximate to 750 psig. The solvent and comonomer (1-octene) feed is pressurized via mechanical positive displacement pump to a pressure that is above the reaction pressure, approximately 750 psig. The individual catalyst components are manually batch diluted to specified component concentrations with purified solvent (Isopar E) and pressurized to a pressure that is above the reaction pressure, approximately 750 psig. All reaction feed flows are measured with mass flow meters, independently controlled with computer automated valve control systems.

The continuous solution polymerization reactor system according to the present invention consist of two liquid full, non-adiabatic, isothermal, circulating, and independently controlled loops operating in a series configuration. Each reactor has independent control of all fresh solvent, monomer, comonomer, hydrogen, and catalyst component feeds. The combined solvent, monomer, comonomer and hydrogen feed to each reactor is independently temperature controlled to anywhere between 5° C. to 50° C. and typically 40° C. by passing the feed stream through a heat exchanger. The fresh comonomer feed to the polymerization reactors can be manually aligned to add comonomer to one of three choices: the first reactor, the second reactor, or the common solvent and then split between both reactors proportionate to the solvent feed split. The total fresh feed to each polymerization reactor is injected into the reactor at two locations per reactor roughly with equal reactor volumes between each injection location. The fresh feed is controlled typically with each injector receiving half of the total fresh feed mass flow. The catalyst components are injected into the polymerization reactor through specially designed injection stingers and are each separately injected into the same relative location in the reactor with no contact time prior to the reactor. The primary catalyst component feed is computer controlled to maintain the reactor monomer concentration at a specified target. The cocatalyst components are fed based on calculated specified molar ratios to the primary catalyst component. Immediately following each fresh injection location (either feed or catalyst), the feed streams are mixed with the circulating polymerization reactor contents with Kenics static mixing elements. The contents of each reactor are continuously circulated through heat exchangers responsible for removing much of the heat of reaction and with the temperature of the coolant side responsible for maintaining isothermal reaction environment at the specified temperature. Circulation around each reactor loop is provided by a screw pump. The effluent from the first polymerization reactor (containing solvent, monomer, comonomer, hydrogen, catalyst components, and molten polymer) exits the first reactor loop and passes through a control valve (responsible for maintaining the pressure of the first reactor at a specified target) and is injected into the second polymerization reactor of similar design. As the stream exits the reactor, it is contacted with water to stop the reaction. In addition, various additives such as anti-oxidants, can be added at this point. The stream then goes through another set of Kenics static mixing elements to evenly disperse the catalyst kill and additives.

Following additive addition, the effluent (containing solvent, monomer, comonomer, hydrogen, catalyst components, and molten polymer) passes through a heat exchanger to raise the stream temperature in preparation for separation of the polymer from the other lower boiling reaction components. The stream then enters a two stage separation and devolatilization system where the polymer is removed from the solvent, hydrogen, and unreacted monomer and comonomer. The recycled stream is purified before entering the reactor again. The separated and devolatized polymer melt is pumped through a die specially designed for underwater pelletization, cut into uniform solid pellets, dried, and transferred into a hopper. The polymer properties are then validated.

The non-polymer portions removed in the devolatilization step pass through various pieces of equipment, which separate most of the ethylene that is removed from the system to a vent destruction unit (it is, however, recycled in manufacturing units). Most of the solvent is recycled back to the reactor after passing through purification beds. This solvent can still have unreacted co-monomer in it that is fortified with fresh co-monomer prior to re-entry to the reactor. This fortification of the co-monomer is an essential part of the product density control method. This recycle solvent can still have some hydrogen which is then fortified with fresh hydrogen to achieve the polymer molecular weight target. A very small amount of solvent leaves the system as a co-product due to solvent carrier in the catalyst streams and a small amount of solvent that is part of commercial grade co-monomers.

Polymerization conditions in a dual reactor system, as described above, for Comparative PE-E, Comparative PE-F, Inventive PE-4, and Inventive PE-5 are reported in Tables 2 and 3. Properties for Comparative PE-E, Comparative PE-F, Inventive PE-4, and Inventive PE-5 were tested, and reported in Table 2 and 3.

TABLE 2

| Measurement | Units | Comparative PE-E | | | Inventive PE-4 | | |
| --- | --- | --- | --- | --- | --- | --- | --- |
| | | Reactor 1 | Reactor 2 | Overall | Reactor 1 | Reactor 2 | Overall |
| Procatalysts | n/a | 2 | 3 | n/a | 2 | 1 | n/a |
| Activator | n/a | RIBS-2 | RIBS-2 | n/a | RIBS-2 | RIBS-2 | n/a |
| Scavenager | n/a | MMAO | MMAO | n/a | MMAO | MMAO | n/a |
| Reactor Temperature | °C. | 150 | 180 | n/a | 150 | 180 | n/a |
| $C_2$ conversion | % | 92.5 | 87.5 | n/a | 92.5 | 87.3 | n/a |
| $H_2$ concentration | mol % | 0.170 | 0.262 | n/a | 0.170 | 0.668 | n/a |
| $C_8/C_2$ molar ratio | unitless | 0.2145 | 0.0728 | n/a | 0.2145 | 0.2630 | n/a |
| $C_2$ feed | (g/L) | 5.00 | 9.60 | n/a | 4.94 | 9.20 | n/a |
| Al/catalyst | unitless | 25.3 | 25.7 | n/a | 25.3 | 26.0 | n/a |
| Efficiency | $10^6$ lbs polymer/lb Ti | 1.52 | 2.50 | n/a | 1.52 | 2.60 | n/a |
| Density | g/cm³ | n/a | n/a | 0.9121 | n/a | n/a | 0.9115 |
| $I_2$ | g/10 min | n/a | n/a | 1.05 | n/a | n/a | 1.06 |
| $I_{10}/I_2$ | g/10 min | n/a | n/a | 7.7 | n/a | n/a | 6.9 |
| $M_W$ | g/mol | n/a | n/a | 101,278 | n/a | n/a | 107,611 |
| $M_N$ | g/mol | n/a | n/a | 40,427 | n/a | n/a | 48,139 |
| PDI ($M_W/M_N$) | unitless | n/a | n/a | 2.51 | n/a | n/a | 2.24 |
| $T_M$ (DSC) | °C. | n/a | n/a | 83, 122 | n/a | n/a | 85, 122 |
| $T_C$ (DSC) | °C. | n/a | n/a | 70, 108 | n/a | n/a | 74, 108 |
| long chain branches (LCB) | LCB/10000 C | n/a | n/a | 0.261 | n/a | n/a | 0.153 |
| Zr amount in resin | ppm(w) | n/a | n/a | n.d | n/a | n/a | n.d |
| Hf amount in resin | ppm(w) | n/a | n/a | 0.17 ± 0.01 | n/a | n/a | 0.14 ± 0.01 |
| Al amount in resin | ppm(w) | n/a | n/a | 3.8 ± 0.2 | n/a | n/a | 3.5 ± 0.2 |

TABLE 3

| Measurement | Units | Comparative PE-F | | | Inventive PE-5 | | |
| --- | --- | --- | --- | --- | --- | --- | --- |
| | | Reactor 1 | Reactor 2 | Overall | Reactor 1 | Reactor 2 | Overall |
| Procatalysts | n/a | 2 | 3 | n/a | 2 | 1 | n/a |
| Activator | n/a | RIBS-2 | RIBS-2 | n/a | RIBS-2 | RIBS-2 | n/a |
| Scavenager | n/a | MMAO | MMAO | n/a | MMAO | MMAO | n/a |
| Reactor Temperature | °C. | 150 | 180 | n/a | 150 | 180 | n/a |
| C2 conversion | % | 92.7 | 87.6 | n/a | 92.5 | 87.8 | n/a |
| H2 concentration | mol % | 0.134 | 0.524 | n/a | 0.134 | 0.996 | n/a |
| C8/C2 molar ratio | unitless | 0.2068 | 0.1740 | n/a | 0.2068 | 0.3034 | n/a |
| C2 feed | (g/L) | 4.85 | 9.70 | n/a | 5.10 | 9.80 | n/a |
| Al/catalyst | unitless | 25.1 | 25.1 | n/a | 25.0 | 24.8 | n/a |
| Efficiency | $10^6$ lbs polymer/lb Ti | 1.96 | 3.90 | n/a | 1.85 | 6.10 | n/a |

TABLE 3-continued

|  |  | Comparative PE-F | | | Inventive PE-5 | | |
| --- | --- | --- | --- | --- | --- | --- | --- |
| Measurement | Units | Reactor 1 | Reactor 2 | Overall | Reactor 1 | Reactor 2 | Overall |
| Density | g/cm$^3$ | n/a | n/a | 0.9133 | n/a | n/a | 0.9122 |
| $I_2$ | g/10 min | n/a | n/a | 0.92 | n/a | n/a | 0.95 |
| $I_{10}/I_2$ | g/10 min | n/a | n/a | 8.3 | n/a | n/a | 6.9 |
| $M_W$ | g/mol | n/a | n/a | 100,393 | n/a | n/a | 105,851 |
| $M_N$ | g/mol | n/a | n/a | 34,882 | n/a | n/a | 46,986 |
| PDI ($M_W/M_N$) | unitless | n/a | n/a | 2.88 | n/a | n/a | 2.25 |
| $T_M$ (DSC) | ° C. | n/a | n/a | 90, 121 | n/a | n/a | 87, 121 |
| $T_C$ (DSC) | ° C. | n/a | n/a | 79, 105 | n/a | n/a | 76, 107 |
| long chain branches (LCB) | LCB/ 10000 C | n/a | n/a | 0.314 | n/a | n/a | 0.168 |
| Zr amount in resin | ppm(w) | n/a | n/a | n.d | n/a | n/a | n.d |
| Hf amount in resin | ppm(w) | n/a | n/a | 0.09 ± 0.01 | n/a | n/a | 0.05 ± 0.01 |
| Al amount in resin | ppm(w) | n/a | n/a | 2.8 ± 0.2 | n/a | n/a | 2.7 ± 0.2 |

Preparation of Ethylene Based Polymers in a 2L Batch Reactor

Polymerization reactions were run at 140° C., and 190° C. A 2-liter Parr reactor was used in the polymerizations. All feeds were passed through columns of alumina and Q-5™ catalyst (available from Engelhard Chemicals Inc.) prior to introduction into the reactor. Procatalyst and activator solutions were handled in the glove box. At 140° C., a stirred 2-liter reactor was charged with about 605 g of mixed alkanes solvent and 300 g of 1-octene comonomer. While the reactor was attaining polymerization temperature, 10 μmol of MMAO were added to the reactor as a scavenger for trace $O_2$ and water. Once at temperature, the reactor was saturated with ethylene at 288 psig. At 190° C., a 2-liter reactor was charged with about 520 g of mixed alkanes solvent and 300 g of 1-octene comonomer. While the reactor was attaining polymerization temperature, 10 μmol of MMAO were added to the reactor as a scavenger for trace $O_2$ and water. Once at temperature, the reactor was saturated with ethylene at 400 psig. Procatalysts and activator, as dilute solutions in toluene, were mixed and transferred to a catalyst addition tank and injected into the reactor. The polymerization conditions were maintained for 10 minutes with ethylene added on demand. Heat was continuously removed from the reaction vessel through an internal cooling coil. The resulting solution was removed from the reactor and stabilized by addition of 10 mL of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation). Between polymerization runs, a wash cycle was conducted in which 850 g of mixed alkanes were added to the reactor and the reactor was heated to 160° C. The reactor was then emptied of the heated solvent immediately before beginning a new polymerization run. Polymers were recovered by drying for about 12 h in a temperature-ramped vacuum oven with a final set point of 140° C.

Batch Reactor Examples 1-12 (BRE 1-12) were prepared according to the above process according to the conditions reported in Tables 4 and 5, and BRE 1-12 were tested for their properties, and those properties are listed in Tables 4 and 5.

TABLE 4

| | | | | | | Ethylene | | | | | | | |
| --- | --- | --- | --- | --- | --- | --- | --- | --- | --- | --- | --- | --- | --- |
| Example No. | Temp (° C.) | IsoparE (g) | Octene (g) | Press (psi) | Catalyst Name | (g) Initial | (g) Added | Yield (g) | Efficiency (gpoly/gMetal) | Tm (° C.) | Mw | Mw/Mn | Octene mol % |
| BRE-1 | 140 | 605 | 300 | 288 | 1 | 44.3 | 12.1 | 29.8 | 8,347,807 | 121.4 | 711,453 | 3.22 | 1.0 |
| BRE-2 | 140 | 605 | 300 | 288 | 5 | 44.5 | 2.6 | 9.2 | 2,577,175 | 121.6 | 1,154,476 | 2.69 | 1.1 |
| BRE-3 | 140 | 605 | 300 | 288 | 5 | 44.2 | 3.4 | 12 | 2,689,226 | 120.5 | 1,386,068 | 2.35 | 0.7 |
| BRE-4 | 190 | 520 | 300 | 400 | 5 | 43.9 | 7.6 | 9.7 | 2,173,791 | 121.2 | 213,791 | 2.14 | 0.9 |
| BRE-5 | 190 | 520 | 300 | 400 | 5 | 44.5 | 10.2 | 11.6 | 649,896 | 116.0 | 448,585 | 2.90 | 1.2 |

Activator: RIBS-2;
Scavenger: MMAO;
Run time = 10 min

TABLE 5

| | | | | | | Ethylene | | | | | | | |
| --- | --- | --- | --- | --- | --- | --- | --- | --- | --- | --- | --- | --- | --- |
| Example No. | Temp (° C.) | IsoparE (g) | Octene (g) | Press (psi) | Procatalyst Name | (g) Initial | (g) Added | Yield (g) | Efficiency (gpoly/gMetal) | Tm (° C.) | Mw | Mw/Mn | Octene mol % |
| BRE-6 | 140 | 605 | 300 | 288 | 4 | 43.2 | 8.2 | 19.8 | 5,546,529 | 101.9 | 574,966 | 2.40 | 3.5 |
| BRE-7 | 140 | 605 | 300 | 288 | 6 | 43.4 | 4.1 | 21.8 | 1,526,696 | 101.5 | 786,264 | 2.44 | 2.5 |
| BRE-8 | 140 | 605 | 300 | 288 | 6 | 44.3 | 12 | 26.5 | 1,855,846 | 102.7 | 938,948 | 3.12 | 2.3 |
| BRE-9 | 140 | 605 | 300 | 288 | 6 | 43.7 | 4 | 22.3 | 1,561,712 | 103.6 | 937,825 | 2.73 | 2.8 |
| BRE-10 | 190 | 520 | 300 | 400 | 6 | 44.2 | 14.1 | 17.9 | 1,253,572 | 103.5 | 309,950 | 2.90 | 3.1 |

TABLE 5-continued

| | | | | | | Ethylene | | | | | | |
|---|---|---|---|---|---|---|---|---|---|---|---|---|
| Example No. | Temp (° C.) | IsoparE (g) | Octene (g) | Press (psi) | Procatalyst Name | (g) Initial | (g) Added | Yield (g) | Efficiency (gpoly/gMetal) | Tm (° C.) | Mw | Mw/Mn | Octene mol % |
| BRE-11 | 190 | 520 | 300 | 400 | 6 | 44.1 | 13.1 | 18.5 | 1,295,591 | 106.8 | 323,298 | 2.87 | 3.1 |
| BRE-12 | 190 | 520 | 300 | 400 | 4 | 43.4 | 7.7 | 11.6 | 3,249,482 | 99.4 | 262,854 | 2.23 | 3.8 |

Activator: RIBS-2;
Scavenger: MMAO;
Run time = 10 min

Test Methods

Test methods include the following:
Density

Samples that are measured for density are prepared according to ASTM D-1928. Measurements are made within one hour of sample pressing using ASTM D-792, Method B.
Melt Index Melt index ($I_2$) is measured in accordance with ASTM-D 1238, Condition 190° C./2.16 kg, and is reported in grams eluted per 10 minutes. Melt flow rate ($I_{10}$) is measured in accordance with ASTM-D 1238, Condition 190° C./10 kg, and is reported in grams eluted per 10 minutes.
DSC Crystallinity Differential Scanning calorimetry (DSC) can be used to measure the melting and crystallization behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (~25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 150° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are peak melting temperature ($T_m$), peak crystallization temperature ($T_c$), heat of fusion ($H_f$) (in Joules per gram), and the calculated % crystallinity for samples using appropriate equation, for example for the ethylene/alpha-olefin interpolymer using Equation 1, as shown in FIG. 1.

The heat of fusion ($H_f$) and the peak melting temperature are reported from the second heat curve. Peak crystallization temperature is determined from the cooling curve.
Dynamic Mechanical Spectroscopy (DMS) Frequency Sweep Melt rheology, constant temperature frequency sweeps, were performed using a TA Instruments Advanced Rheometric Expansion System (ARES) rheometer equipped with 25 mm parallel plates under a nitrogen purge. Frequency sweeps were performed at 190° C. for all samples at a gap of 2.0 mm and at a constant strain of 10%. The frequency interval was from 0.1 to 100 radians/second. The stress response was analyzed in terms of amplitude and phase, from which the storage modulus (G'), loss modulus (G"), and dynamic melt viscosity ($\eta^*$) were calculated.
Gel Permeation Chromatography (GPC)

The ethylene/alpha-olefin interpolymers were tested for their properties via GPC, according to the following procedure. The GPC system consists of a Waters (Milford, Mass.) 150° C. high temperature chromatograph (other suitable high temperatures GPC instruments include Polymer Laboratories (Shropshire, UK) Model 210 and Model 220) equipped with an on-board differential refractometer (RI). Additional detectors can include an IR4 infra-red detector from Polymer ChAR (Valencia, Spain), Precision Detectors (Amherst, Mass.) 2-angle laser light scattering detector Model 2040, and a Viscotek (Houston, Tex.) 150R 4-capillary solution viscometer. A GPC with the last two independent detectors and at least one of the first detectors is sometimes referred to as "3D-GPC", while the term "GPC" alone generally refers to conventional GPC. Depending on the sample, either the 15-degree angle or the 90-degree angle of the light scattering detector is used for calculation purposes. Data collection is performed using Viscotek TriSEC software, Version 3, and a 4-channel Viscotek Data Manager DM400. The system is also equipped with an on-line solvent degassing device from Polymer Laboratories (Shropshire, UK). Suitable high temperature GPC columns can be used such as four 30 cm long Shodex HT803 13 micron columns or four 30 cm Polymer Labs columns of 20-micron mixed-pore-size packing (MixA LS, Polymer Labs). The sample carousel compartment is operated at 140° C. and the column compartment is operated at 150° C. The samples are prepared at a concentration of 0.1 grams of polymer in 50 milliliters of solvent. The chromatographic solvent and the sample preparation solvent contain 200 ppm of butylated hydroxytoluene (BHT). Both solvents are sparged with nitrogen. The polyethylene samples are gently stirred at 160° C. for four hours. The injection volume is 200 microliters. The flow rate through the GPC is set at 1 ml/minute.

The GPC column set is calibrated before running the Examples by running twenty-one narrow molecular weight distribution polystyrene standards. The molecular weight (MW) of the standards ranges from 580 to 8,400,000 grams per mole, and the standards are contained in 6 "cocktail" mixtures. Each standard mixture has at least a decade of separation between individual molecular weights. The standard mixtures are purchased from Polymer Laboratories (Shropshire, UK). The polystyrene standards are prepared at 0.025 g in 50 mL of solvent for molecular weights equal to or greater than 1,000,000 grams per mole and 0.05 g in 50 ml of solvent for molecular weights less than 1,000,000 grams per mole. The polystyrene standards were dissolved at 80° C. with gentle agitation for 30 minutes. The narrow standards mixtures are run first and in order of decreasing highest molecular weight component to minimize degradation. The polystyrene standard peak molecular weights are converted to polyethylene $M_w$ using the Mark-Houwink K and a (sometimes referred to as α) values mentioned later for polystyrene and polyethylene. See the Examples section for a demonstration of this procedure.

With 3D-GPC, absolute weight average molecular weight ("$M_{w,\ Abs}$") and intrinsic viscosity are also obtained independently from suitable narrow polyethylene standards using the same conditions mentioned previously. These narrow linear polyethylene standards may be obtained from Polymer Laboratories (Shropshire, UK; Part No.'s PL2650-0101 and PL2650-0102).

The systematic approach for the determination of multi-detector offsets is performed in a manner consistent with that published by Balke, Mourey, et al. (Mourey and Balke, *Chromatography Polym.*, Chapter 12, (1992)) (Balke, Thitiratsakul, Lew, Cheung, Mourey, *Chromatography Polym.*, Chapter 13, (1992)), optimizing triple detector log ($M_w$ and intrinsic viscosity) results from Dow 1683 broad polystyrene (American Polymer Standards Corp.; Mentor, Ohio) or its equivalent to the narrow standard column calibration results from the narrow polystyrene standards calibration curve. The molecular weight data, accounting for detector volume off-set determination, are obtained in a manner consistent with that published by Zimm (Zimm, B. H., *J. Chem. Phys.*, 16, 1099 (1948)) and Kratochvil (Kratochvil, P., *Classical Light Scattering from Polymer Solutions*, Elsevier, Oxford, N.Y. (1987)). The overall injected concentration used in the determination of the molecular weight is obtained from the mass detector area and the mass detector constant derived from a suitable linear polyethylene homopolymer, or one of the polyethylene standards. The calculated molecular weights are obtained using a light scattering constant derived from one or more of the polyethylene standards mentioned and a refractive index concentration coefficient, dn/dc, of 0.104. Generally, the mass detector response and the light scattering constant should be determined from a linear standard with a molecular weight in excess of about 50,000 daltons. The viscometer calibration can be accomplished using the methods described by the manufacturer or alternatively by using the published values of suitable linear standards such as Standard Reference Materials (SRM) 1475a, 1482a, 1483, or 1484a. The chromatographic concentrations are assumed low enough to eliminate addressing $2^{nd}$ viral coefficient effects (concentration effects on molecular weight).

g' by 3D-GPC

The index (g') for the sample polymer is determined by first calibrating the light scattering, viscosity, and concentration detectors described in the Gel Permeation Chromatography method supra with SRM 1475a homopolymer polyethylene (or an equivalent reference). The light scattering and viscometer detector offsets are determined relative to the concentration detector as described in the calibration. Baselines are subtracted from the light scattering, viscometer, and concentration chromatograms and integration windows are then set making certain to integrate all of the low molecular weight retention volume range in the light scattering and viscometer chromatograms that indicate the presence of detectable polymer from the refractive index chromatogram. A linear homopolymer polyethylene is used to establish a Mark-Houwink (MH) linear reference line by injecting a broad molecular weight polyethylene reference such as SRM1475a standard, calculating the data file, and recording the intrinsic viscosity (IV) and molecular weight ($M_w$), each derived from the light scattering and viscosity detectors respectively and the concentration as determined from the RI detector mass constant for each chromatographic slice. For the analysis of samples the procedure for each chromatographic slice is repeated to obtain a sample Mark-Houwink line. Note that for some samples the lower molecular weights, the intrinsic viscosity and the molecular weight data may need to be extrapolated such that the measured molecular weight and intrinsic viscosity asymptotically approach a linear homopolymer GPC calibration curve. To this end, many highly-branched ethylene-based polymer samples require that the linear reference line be shifted slightly to account for the contribution of short chain branching before proceeding with the long chain branching index (g') calculation.

A g-prime ($g_i'$) is calculated for each branched sample chromatographic slice (i) and measuring molecular weight ($M_i$) according to Equation 2, as shown in FIG. 2, where the calculation utilizes the $IV_{linear\ reference,j}$ at equivalent molecular weight, in the linear reference sample. In other words, the sample IV slice (i) and reference IV slice (j) have the same molecular weight ($M_i=M_j$). For simplicity, the $IV_{linear\ reference,j}$ slices are calculated from a fifth-order polynomial fit of the reference Mark-Houwink Plot. The IV ratio, or $g_i'$, is only obtained at molecular weights greater than 3,500 because of signal-to-noise limitations in the light scattering data. The number of branches along the sample polymer ($B_n$) at each data slice (i) can be determined by using Equation 3, as shown in FIG. 3, assuming a viscosity shielding epsilon factor of 0.75.

Finally, the average LCBf quantity per 1000 carbons in the polymer across all of the slices (i) can be determined using Equation 4, as shown in FIG. 4.

gpcBR Branching Index by 3D-GPC

In the 3D-GPC configuration the polyethylene and polystyrene standards can be used to measure the Mark-Houwink constants, K and α, independently for each of the two polymer types, polystyrene and polyethylene. These can be used to refine the Williams and Ward polyethylene equivalent molecular weights in application of the following methods.

The gpcBR branching index is determined by first calibrating the light scattering, viscosity, and concentration detectors as described previously. Baselines are then subtracted from the light scattering, viscometer, and concentration chromatograms. Integration windows are then set to ensure integration of all of the low molecular weight retention volume range in the light scattering and viscometer chromatograms that indicate the presence of detectable polymer from the refractive index chromatogram. Linear polyethylene standards are then used to establish polyethylene and polystyrene Mark-Houwink constants as described previously. Upon obtaining the constants, the two values are used to construct two linear reference conventional calibrations ("cc") for polyethylene molecular weight and polyethylene intrinsic viscosity as a function of elution volume, as shown in Equations 5 and 6, FIGS. 5 and 6, respectively.

The gpcBR branching index is a robust method for the characterization of long chain branching. See Yau, Wallace W., "Examples of Using 3D-GPC-TREF for Polyolefin Characterization", *Macromol. Symp.*, 2007, 257, 29-45. The index avoids the slice-by-slice 3D-GPC calculations traditionally used in the determination of g' values and branching frequency calculations in favor of whole polymer detector areas and area dot products. From 3D-GPC data, one can obtain the sample bulk $M_w$ by the light scattering (LS) detector using the peak area method. The method avoids the slice-by-slice ratio of light scattering detector signal over the concentration detector signal as required in the g' determination.

The area calculation in Equation 7, shown in FIG. 7, offers more precision because as an overall sample area it is much less sensitive to variation caused by detector noise and GPC settings on baseline and integration limits. More importantly, the peak area calculation is not affected by the detector volume offsets. Similarly, the high-precision sample intrinsic viscosity (IV) is obtained by the area method shown in Equation 8, as shown in FIG. 8, where $DP_i$ stands for the differential pressure signal monitored directly from the online viscometer.

To determine the gpcBR branching index, the light scattering elution area for the sample polymer is used to determine the molecular weight of the sample. The viscosity detector elution area for the sample polymer is used to determine the intrinsic viscosity (IV or [η]) of the sample.

Initially, the molecular weight and intrinsic viscosity for a linear polyethylene standard sample, such as SRM1475a or an equivalent, are determined using the conventional calibrations for both molecular weight and intrinsic viscosity as a function of elution volume, per Equations 9 and 10, as shown in FIGS. 9 and 10, respectively.

Equation 11, as shown in FIG. 11, is used to determine the gpcBR branching index, where [η] is the measured intrinsic viscosity, $[\eta]_{cc}$ is the intrinsic viscosity from the conventional calibration, $M_w$ is the measured weight average molecular weight, and $M_{w,cc}$ is the weight average molecular weight of the conventional calibration. The Mw by light scattering (LS) using Equation 7, as shown in FIG. 7, is commonly referred to as the absolute Mw; while the Mw,cc from Equation 9, as shown in FIG. 9, using the conventional GPC molecular weight calibration curve is often referred to as polymer chain Mw. All statistical values with the "cc" subscript are determined using their respective elution volumes, the corresponding conventional calibration as previously described, and the concentration ($C_i$) derived from the mass detector response. The non-subscripted values are measured values based on the mass detector, LALLS, and viscometer areas. The value of $K_{PE}$ is adjusted iteratively until the linear reference sample has a gpcBR measured value of zero. For example, the final values for a and Log K for the determination of gpcBR in this particular case are 0.725 and −3.355, respectively, for polyethylene, and 0.722 and −3.993 for polystyrene, respectively.

Once the K and α values have been determined, the procedure is repeated using the branched samples. The branched samples are analyzed using the final Mark-Houwink constants as the best "cc" calibration values and applying Equations 7-11, as shown in FIG. 7-11, respectively.

The interpretation of gpcBR is straight forward. For linear polymers, gpcBR calculated from Equation 11, as shown in FIG. 11, will be close to zero since the values measured by LS and viscometry will be close to the conventional calibration standard. For branched polymers, gpcBR will be higher than zero, especially with high levels of LCB, because the measured polymer $M_w$ will be higher than the calculated $M_{w,cc}$, and the calculated $IV_{cc}$ will be higher than the measured polymer Intrinsic Viscosity (IV). In fact, the gpcBR value represents the fractional IV change due to the molecular size contraction effect as the result of polymer branching. A gpcBR value of 0.5 or 2.0 would mean a molecular size contraction effect of IV at the level of 50% and 200%, respectively, versus a linear polymer molecule of equivalent weight.

For these particular Examples, the advantage of using gpcBR in comparison to the g' index and branching frequency calculations is due to the higher precision of gpcBR. All of the parameters used in the gpcBR index determination are obtained with good precision and are not detrimentally affected by the low 3D-GPC detector response at high molecular weight from the concentration detector. Errors in detector volume alignment also do not affect the precision of the gpcBR index determination. In other particular cases, other methods for determining $M_w$ moments may be preferable to the aforementioned technique.

CEF Method

Comonomer distribution analysis is performed with Crystallization Elution Fractionation (CEF) (PolymerChar in Spain) (B Monrabal et al, Macromol. Symp. 257, 71-79 (2007)). Ortho-dichlorobenzene (ODCB) with 600 ppm antioxidant butylated hydroxytoluene (BHT) is used as solvent. Sample preparation is done with autosampler at 160° C. for 2 hours under shaking at 4 mg/ml (unless otherwise specified). The injection volume is 300 μl. The temperature profile of CEF is: crystallization at 3° C./min from 110° C. to 30° C., the thermal equilibrium at 30° C. for 5 minutes, elution at 3° C./min from 30° C. to 140° C. The flow rate during crystallization is at 0.052 ml/min. The flow rate during elution is at 0.50 ml/min. The data is collected at one data point/second.

CEF column is packed by the Dow Chemical Company with glass beads at 125 μm±6% (MO-SCI Specialty Products) with ⅛ inch stainless tubing. Glass beads are acid washed by MO-SCI Specialty with the request from the Dow Chemical Company. Column volume is 2.06 ml. Column temperature calibration is performed by using a mixture of NIST Standard Reference Material Linear polyethylene 1475a (1.0 mg/ml) and Eicosane (2 mg/ml) in ODCB. Temperature is calibrated by adjusting elution heating rate so that NIST linear polyethylene 1475a has a peak temperature at 101.0° C., and Eicosane has a peak temperature of 30.0° C. The CEF column resolution is calculated with a mixture of NIST linear polyethylene 1475a (1.0 mg/ml) and hexacontane (Fluka, purum, ≥97.0%, 1 mg/ml). A baseline separation of hexacontane and NIST polyethylene 1475a is achieved. The area of hexacontane (from 35.0 to 67.0° C.) to the area of NIST 1475a from 67.0 to 110.0° C. is 50 to 50, the amount of soluble fraction below 35.0° C. is <1.8 wt %. The CEF column resolution is defined in equation 12, as shown in FIG. 12, where the column resolution is 6.0.

CDC Method

Comonomer distribution constant (CDC) is calculated from comonomer distribution profile by CEF. CDC is defined as Comonomer Distribution Index divided by Comonomer Distribution Shape Factor multiplying by 100 as shown in Equation 13, FIG. 13.

Comonomer distribution index stands for the total weight fraction of polymer chains with the comonomer content ranging from 0.5 of median comonomer content ($C_{median}$) and 1.5 of $C_{median}$ from 35.0 to 119.0° C. Comonomer Distribution Shape Factor is defined as a ratio of the half width of comonomer distribution profile divided by the standard deviation of comonomer distribution profile from the peak temperature ($T_p$).

CDC is calculated from comonomer distribution profile by CEF, and CDC is defined as Comonomer Distribution Index divided by Comonomer Distribution Shape Factor multiplying by 100 as shown in Equation 13, FIG. 13, and wherein Comonomer distribution index stands for the total weight fraction of polymer chains with the comonomer content ranging from 0.5 of median comonomer content ($C_{median}$) and 1.5 of $C_{median}$ from 35.0 to 119.0° C., and wherein Comonomer Distribution Shape Factor is defined as a ratio of the half width of comonomer distribution profile divided by the standard deviation of comonomer distribution profile from the peak temperature (Tp).

CDC is calculated according to the following steps:

(A) Obtain a weight fraction at each temperature (T) ($w_T$(T)) from 35.0° C. to 119.0° C. with a temperature step increase of 0.200° C. from CEF according to Equation 14, as shown in FIG. 14;

(B) Calculate the median temperature ($T_{median}$ at cumulative weight fraction of 0.500, according to Equation 15, as shown in FIG. 15;

(C) Calculate the corresponding median comonomer content in mole % ($C_{median}$) at the median temperature ($T_{median}$) by using comonomer content calibration curve according to Equation 16, as shown in FIG. 16;

(D) Construct a comonomer content calibration curve by using a series of reference materials with known amount of comonomer content, i.e., eleven reference materials with narrow comonomer distribution (mono-modal comonomer distribution in CEF from 35.0 to 119.0° C.) with weight average Mw of 35,000 to 115,000 (measured via conventional GPC) at a comonomer content ranging from 0.0 mole % to 7.0 mole % are analyzed with CEF at the same experimental conditions specified in CEF experimental sections;

(E) Calculate comonomer content calibration by using the peak temperature ($T_p$) of each reference material and its comonomer content; The calibration is calculated from each reference material as shown in Formula 16, FIG. 16, wherein: $R^2$ is the correlation constant;

(F) Calculate Comonomer Distribution Index from the total weight fraction with a comonomer content ranging from $0.5*C_{median}$ to $1.5*C_{median}$, and if $T_{median}$ is higher than 98.0° C., Comonomer Distribution Index is defined as 0.95;

(G) Obtain Maximum peak height from CEF comonomer distribution profile by searching each data point for the highest peak from 35.0° C. to 119.0° C. (if the two peaks are identical, then the lower temperature peak is selected); half width is defined as the temperature difference between the front temperature and the rear temperature at the half of the maximum peak height, the front temperature at the half of the maximum peak is searched forward from 35.0° C., while the rear temperature at the half of the maximum peak is searched backward from 119.0° C., in the case of a well defined bimodal distribution where the difference in the peak temperatures is equal to or greater than the 1.1 times of the sum of half width of each peak, the half width of the inventive ethylene-based polymer composition is calculated as the arithmetic average of the half width of each peak; and (H) Calculate the standard deviation of temperature (Stdev) according Equation 17, as shown in FIG. 17.

Creep Zero Shear Viscosity Method

Zero-shear viscosities are obtained via creep tests that are conducted on an AR-G2 stress controlled rheometer (TA Instruments; New Castle, Del.) using 25-mm-diameter parallel plates at 190° C. The rheometer oven is set to test temperature for at least 30 minutes prior to zeroing fixtures. At the testing temperature a compression molded sample disk is inserted between the plates and allowed to come to equilibrium for 5 minutes. The upper plate is then lowered down to 50 μm above the desired testing gap (1.5 mm). Any superfluous material is trimmed off and the upper plate is lowered to the desired gap. Measurements are done under nitrogen purging at a flow rate of 5 L/min. Default creep time is set for 2 hours.

A constant low shear stress of 20 Pa is applied for all of the samples to ensure that the steady state shear rate is low enough to be in the Newtonian region. The resulting steady state shear rates are in the order of $10^{-3}$ $s^{-1}$ for the samples in this study. Steady state is determined by taking a linear regression for all the data in the last 10% time window of the plot of log(J(t)) vs. log(t), where J(t) is creep compliance and t is creep time. If the slope of the linear regression is greater than 0.97, steady state is considered to be reached, then the creep test is stopped. In all cases in this study the slope meets the criterion within 30 minutes. The steady state shear rate is determined from the slope of the linear regression of all of the data points in the last 10% time window of the plot of □□ vs. t, where ε is strain. The zero-shear viscosity is determined from the ratio of the applied stress to the steady state shear rate.

In order to determine if the sample is degraded during the creep test, a small amplitude oscillatory shear test is conducted before and after the creep test on the same specimen from 0.1 to 100 rad/s. The complex viscosity values of the two tests are compared. If the difference of the viscosity values at 0.1 rad/s is greater than 5%, the sample is considered to have degraded during the creep test, and the result is discarded.

Zero-Shear Viscosity Ratio

Zero-shear viscosity ratio (ZSVR) is defined as the ratio of the zero-shear viscosity (ZSV) of the inventive polymer to the ZSV of a linear polyethylene material at the equivalent weight average molecular weight ($M_{w-gpc}$) as shown in the Equation 18, as shown in FIG. 18.

The $\eta_0$ value (in Pa.s) is obtained from creep test at 190° C. via the method described above. It is known that ZSV of linear polyethylene $\eta_{0L}$ has a power law dependence on its $M_w$ when the $M_w$ is above the critical molecular weight $M_c$. An example of such a relationship is described in Karjala et al. (Annual Technical Conference—Society of Plastics Engineers (2008), 66$^{th}$, 887-891) as shown in the Equation 19, as shown in FIG. 19, to calculate the ZSVR values. Referring to Equation 19, as showing in FIG. 19, $M_{w-gpc}$ value (g/mol) is determined by using the GPC method as defined immediately hereinbelow.

$M_{w-gpc}$ Determination

To obtain $M_{w-gpc}$ values, the chromatographic system consist of either a Polymer Laboratories Model PL-210 or a Polymer Laboratories Model PL-220. The column and carousel compartments are operated at 140° C. Three Polymer Laboratories 10-μm Mixed-B columns are used with a solvent of 1,2,4-trichlorobenzene. The samples are prepared at a concentration of 0.1 g of polymer in 50 mL of solvent. The solvent used to prepare the samples contain 200 ppm of the antioxidant butylated hydroxytoluene (BHT). Samples were prepared by agitating lightly for 4 hours at 160° C. The injection volume used is 100 microliters and the flow rate is 1.0 mL/min. Calibration of the GPC column set is performed with twenty one narrow molecular weight distribution polystyrene standards purchased from Polymer Laboratories. The polystyrene standard peak molecular weights are converted to polyethylene molecular weights using Equation 20, as shown in FIG. 20.

Referring to Equation 20, as shown in FIG. 20, M is the molecular weight, A has a value of 0.4316 and B is equal to 1.0. A third order polynomial is determined to build the logarithmic molecular weight calibration as a function of elution volume. Polyethylene equivalent molecular weight calculations are performed using Viscotek TriSEC software Version 3.0. The precision of the weight-average molecular weight □$M_w$ is excellent at <2.6%.

Polymer Characterization. Melting ($T_m$) and glass transition ($T_g$) temperatures of polymers were measured by differential scanning calorimetry (Q2000 DSC, TA Instruments, Inc.). Samples were first heated from room temperature to 200° C. using the 'Jump To' feature. After being held at this temperature for 4 min, the samples were cooled to −90° C. at 10° C./min, held for 4 min, and were then heated again to 200° C. Molecular weight distribution (Mw, Mn) information was determined by analysis on a custom Dow-built Robotic-Assisted Dilution High-Temperature Gel Permeation Chromatographer (RAD-GPC). Polymer samples were dissolved for 90 minutes at 160° C. at a concentration of 5-7 mg/mL in 1,2,4-trichlorobenzene (TCB) stabilized by 300 ppm of BHT in capped vials while stirring. They were then diluted to 1 mg/mL immediately before a 400 µL aliquot of the sample was injected. The GPC utilized two (2) Polymer Labs PL gel 10 µm MIXED-B columns (300 mm×10 mm) at a flow rate of 2.0 mL/minute at 150° C. Sample detection was performed using a Poly-Char IR4 detector in concentration mode. A conventional calibration of narrow Polystyrene (PS) standards was utilized, with apparent units adjusted to homo-polyethylene (PE) using known Mark-Houwink coefficients for PS and PE in TCB at this temperature. To determine 1-octene incorporation, polymer samples were dissolved at a concentration of 30 mg/mL in 1,2,4-Trichlorobenzene at 160° C. for 1 hr while shaking. A 100 µL aliquot of each polymer/TCB solution was deposited into individual cells on a custom silicon wafer at 160° C. under nitrogen inerting. The wafer was held at 160° C. for 45 minutes, and then pulled from heat and allowed to cool to room temperature. The wafer was then analyzed using a Nicolet Nexus 670 FT-IR ESP infrared spectrometer. Mol % 1-octene within each sample was determined by taking a ratio of the $CH_3$ area (1382.7-1373.5 wavenumbers) to the $CH_2$ area (1525-1400 wavenumbers) and normalizing to a standard curve generated through NMR analysis of ethylene-co-1-octene polymer standards.

The present invention may be embodied in other forms without departing from the spirit and the essential attributes thereof, and, accordingly, reference should be made to the appended claims, rather than to the foregoing specification, as indicating the scope of the invention.

We claim:

1. A procatalyst comprising a metal-ligand complex of formula (I):

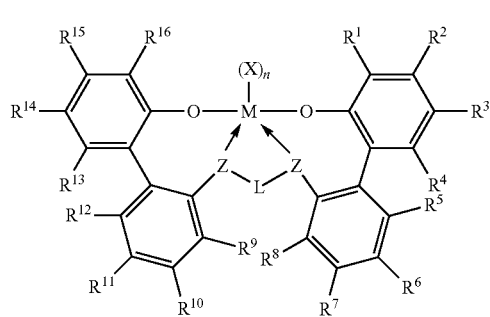

where:
M is titanium, zirconium, or hafnium, each independently being in a formal oxidation state of +2, +3, or +4; and n is an integer from 0 to 3, and wherein when n is 0, X is absent;

each X independently is a monodentate ligand that is neutral, monoanionic, or dianionic; or two Xs are taken together to form a bidentate ligand that is neutral, monoanionic, or dianionic; and X and n are chosen in such a way that the metal-ligand complex of formula (I) is, overall, neutral;

each Z is O;

L is $(C_3\text{-}C_{40})$hydrocarbylene or $(C_3\text{-}C_{40})$heterohydrocarbylene, wherein the $(C_3\text{-}C_{40})$hydrocarbylene has a portion that comprises a 3-carbon atom to 10-carbon atom linker backbone linking the Z atoms in formula (I) and the $(C_3\text{-}C_{40})$heterohydrocarbylene has a portion that comprises a 3-atom to 10-atom linker backbone linking the Z atoms in formula (I), wherein each of the 3 to 10 atoms of the 3-atom to 10-atom linker backbone of the $(C_3\text{-}C_{40})$heterohydrocarbylene independently is a carbon atom or heteroatom, wherein each heteroatom independently is O, S, S(O), S(O)$_2$, Si(R$^C$)$_2$, Ge(R$^C$)$_2$, P(R$^P$), —N═, or N(R″), wherein independently each R$^C$ is $(C_1\text{-}C_{30})$hydrocarbyl, each R$^P$ is $(C_1\text{-}C_{30})$hydrocarbyl; and each R$^N$ is $(C_1\text{-}C_{30})$hydrocarbyl;

R$^2$, R$^3$, R$^4$, R$^5$, R$^6$, R$^7$, R$^8$, R$^9$, R$^{10}$, R$^{11}$, R$^{12}$, R$^{13}$, R$^{14}$ and R$^{15}$ are independently selected from the group consisting of a $(C_1\text{-}C_{40})$hydrocarbyl, $(C_1\text{-}C_{40})$heterohydrocarbyl, Si(R$^C$)$_3$, Ge(R$^C$)$_3$, P(R$^P$)$_2$, N(R$^N$)$_2$, OR$^C$, SR$^C$, NO$_2$, CN, CF$_3$, R$^C$S(O)—, R$^C$S(O)$_2$-, (R$^C$)$_2$C═N—, R$^C$C(O)O—, R$^C$OC(O)—, R$^C$C(O)N(R)—, (R$^C$)$_2$NC(O)—, halogen atom, and hydrogen atom when R$^8$ is H, R$^9$ is a $(C_1\text{-}C_{40})$hydrocarbyl; $(C_1\text{-}C_{40})$heterohydrocarbyl; Si(R$^C$)$_3$, Ge(R$^C$)$_3$, P(R$^P$)$_2$, N(R$^N$)$_2$, OR$^C$, SR$^C$, NO$_2$, CN, CF$_3$, R$^C$S(O)—, R$^C$S(O)$_2$-, (R$^C$)$_2$C═N—, R$^C$C(O)O—, R$^C$OC(O)—, R$^C$C(O)N(R)—, (R$^C$)$_2$NC(O)—or halogen atom; or when R$^9$ is H, R$^8$ is a $(C_1\text{-}C_{40})$hydrocarbyl; $(C_1\text{-}C_{40})$heterohydrocarbyl; Si(R$^C$)$_3$, Ge(R$^C$)$_3$, P(R$^P$)$_2$, N(R$^N$)$_2$, OR$^C$, SR$^C$, NO$_2$, CN, CF$_3$, R$^C$S(O)—, R$^C$S(O)$_2$-, (R$^C$)$_2$C═N—, R$^C$C(O)O—, R$^C$OC(O)—, R$^C$C(O)N(R)—, (R$^C$)$_2$ NC(O)—or halogen atom; and R$^1$ and R$^{16}$ are independently selected from radicals having formula (II)

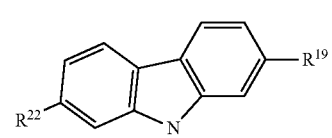

where each R$^{22}$ and R$^{19}$ is independently chosen from $(C_1\text{-}C_{20})$alkyl, $(C_3\text{-}C_{40})$cycloalkyl, $(C_{6\text{-}C40})$aryl, $(C_1\text{-}C_{40})$heterohydrocarbyl, -Si(R$^C$)$_3$, -Ge(R$^C$)$_3$, -N(R$^N$)$_2$, -N═R$^C$, -OR$^C$;

optionally two or more of R$^2$, R$^3$, and R$^4$, or two or more of R$^5$, R$^6$, R$^7$, and R$^8$, or two or more of R$^9$, R$^{10}$, R$^{11}$, and R$^{12}$, or two or more of R$^{13}$, R$^{14}$ and R$^{15}$ can be covalently connect in ring structures, with such ring structures having from 3 to 50 atoms in the ring excluding any hydrogen atoms;

each of the aryl, heteroaryl, hydrocarbyl, heterohydrocarbyl, Si(R$^C$)$_3$, Ge(R$^C$)$_3$, P(R$^P$)$_2$, N(R$^N$)$_2$, OR$^C$, SR$^C$, R$^C$S(O)—, R$^C$S(O)$_2$-, (R$^C$)$_2$C═N—, R$^C$C(O)O—, R$^C$OC(O)—, R$^C$C(O)N(R)—, (R$^C$)$_2$NC(O)—, hydrocarbylene, and heterohydrocarbylene groups independently is unsubstituted or substituted with one or more $R^s$ substituents; and each $R^s$ independently is a halogen atom, unsubstituted $(C_1-C_{18})$alkyl, $F_3C-$, $FCH_2O-$, $F_2HCO-$, $F_3CO-$, $R_3Si-$, $R_3Ge-$, $RO-$, $RS-$, $RS(O)-$, $RS(O)_2-$, $R_2P-$, $R_2N-$, $R_2C=N-$, $NC-$, $RC(O)O-$, $ROC(O)-$, $RC(O)N(R)-$, or $R_2NC(O)-$, or two of the $R^s$ are taken together to form an unsubstituted $(C_1-C_{18})$alkylene, wherein each R independently is an unsubstituted $(C_1-C_{18})$alkyl.

2. The polymerization process according to claim 1, wherein $R^3$ and $R^{14}$ are independently chosen from tert-octyl or tent-butyl.

3. The polymerization process according to claim 1, wherein $R^8$ and $R^9$ are independently chosen from methyl, ethyl, 2-propyl, chloro, fluoro, or $-NMe_2$.

4. The polymerization process according to claim 1, wherein $R^6$ and $R^{11}$ are independently chosen from methyl, chloro, or fluoro.

5. The polymerization process according to claim 1, wherein each $R^{19}$ and each $R^{22}$ is independently chosen tent-butyl, n-propyl, 2-propyl, cyclohexyl, $-SiMe_3$, $-Si(Me)_2(tBu)$, $-CH_2Si(Me)_3$, 3,5-di-tert-butylphenyl, 3,5-dimethylphenyl, or phenyl.

6. The polymerization process according to claim 1, wherein each $R^{19}$ and each $R^{22}$ are tert-butyl.

7. The polymerization process according to claim 1, wherein each $R^{19}$ and each $R^{22}$ are tert-butyl; $R^3$ and $R^{14}$ are tert-octyl; $R^6$ and $R^{11}$ are fluoro; $R^8$ is hydrogen; and $R^9$ is methyl.

8. The polymerization process according to claim 1, wherein each $R^{19}$ and each $R^{22}$ are tert-butyl; $R^3$ and $R^{14}$ are tert-octyl; $R^6$ and $R^{11}$ are fluoro; and $R^8$ and $R^9$ are methyl.

9. The polymerization process according to claim 1, wherein each $R^{19}$ and each $R^{22}$ are tert-butyl; $R^3$ and $R^{14}$ are tert-octyl; $R^6$ and $R^{11}$ are fluoro; $R^8$ and $R^9$ are methyl; and L is $-CH_2Si(Et)_2CH-$.

10. The polymerization process according to claim 1, wherein each $R^{19}$ and each $R^{22}$ are tert-butyl; $R^3$ and $R^{14}$ are tert-octyl; $R^6$ and $R^{11}$ are fluoro; $R^8$ is hydrogen; $R^9$ is methyl; and L is $-CH_2Si(Et)_2CH-$.

11. A catalyst system comprising the reaction product of:
one or more procatalysts of claim 1; and
one or more cocatalysts; wherein the ratio of total number of moles of the one or more metal-ligand complexes of formula (I) to total number of moles of the one or more cocatalysts is from 1:10,000 to 100:1.

12. A polymerization process comprising:
polymerizing ethylene one or more a-olefins in the presence of one or more catalyst systems of claim 1 under olefin polymerizing conditions; and thereby forming an olefin based polymer.

* * * * *

UNITED STATES PATENT AND TRADEMARK OFFICE
CERTIFICATE OF CORRECTION

PATENT NO. : 10,214,622 B2  
APPLICATION NO. : 15/652606  
DATED : February 26, 2019  
INVENTOR(S) : Jerzy Klosin et al.

Page 1 of 1

It is certified that error appears in the above-identified patent and that said Letters Patent is hereby corrected as shown below:

In the Claims

Column 110, Line 22, Claim 1:
"independently is O, S, S(O), S(O)$_2$, Si(R$^c$)$_2$, Ge(R$^c$)$_2$,"
Should read:
--independently is O, S, S(O), S(O)$_2$, Si(R$^c$)$_2$, Ge(R$^c$)$_2$,--

Column 110, Line 23, Claim 1:
"P(R$^P$), –N==, or N(R$^n$), wherein independently each"
Should read:
--P(R$^P$), –N==, or N(R$^N$), wherein independently each--

Column 110, Line 55, Claim 1:
"(C$_1$-C$_{20}$)alkyl, (C$_3$-C$_{40}$)cycloalkyl, (C$_{6\text{-}C40}$)aryl, (C$_1$-"
Should read:
--(C$_1$-C$_{20}$)alkyl, (C$_3$-C$_{40}$)cycloalkyl, (C$_6$-C$_{40}$)aryl, (C$_1$- --

Column 111, Line 23, Claim 5:
"tent-butyl, n-propyl, 2-propyl, cyclohexyl, –SiMe$_3$, –Si"
Should read:
--tert-butyl, n-propyl, 2-propyl, cyclohexyl, –SiMe$_3$, –S– --

Column 112, Line 23, Claim 12:
"polymerizing ethylene one or more a-olefins in a pres-"
Should read:
--polymerizing ethylene one or more α-olefins in a pres- --

Signed and Sealed this  
Third Day of November, 2020

Andrei Iancu  
*Director of the United States Patent and Trademark Office*